(12) United States Patent
Krueger

(10) Patent No.: US 10,716,469 B2
(45) Date of Patent: *Jul. 21, 2020

(54) OCULAR-PERFORMANCE-BASED HEAD IMPACT MEASUREMENT APPLIED TO ROTATIONALLY-CENTERED IMPACT MITIGATION SYSTEMS AND METHODS

(71) Applicant: Wesley W. O. Krueger, San Antonio, TX (US)

(72) Inventor: Wesley W. O. Krueger, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/264,242

(22) Filed: Jan. 31, 2019

(65) Prior Publication Data
US 2019/0167095 A1 Jun. 6, 2019

Related U.S. Application Data

(63) Continuation-in-part of application No. 15/713,418, filed on Sep. 22, 2017, now Pat. No. 10,231,614, (Continued)

(51) Int. Cl.
*A61B 3/14* (2006.01)
*A61B 3/113* (2006.01)
(Continued)

(52) U.S. Cl.
CPC .............. *A61B 3/113* (2013.01); *A61B 3/112* (2013.01); *A61B 3/145* (2013.01); *A61B 3/0041* (2013.01);
(Continued)

(58) Field of Classification Search
CPC ......... A61B 3/113; A61B 3/0025; A61B 3/14; G06K 9/00604; G06F 3/013
(Continued)

(56) References Cited

U.S. PATENT DOCUMENTS 3,616,463 A 11/1971 Theodore et al.
4,817,633 A 4/1989 McStravick et al.
(Continued)

FOREIGN PATENT DOCUMENTS

WO 2013-117727 5/2013

OTHER PUBLICATIONS

Allison, et al. "Combined Head and Eye Tracking System for Dynamic Testing of the Vestibular System" IEEE Transactions on Biomedical Engineering, vol. 43, No. 11, Nov. 1996, all pages.
(Continued)

*Primary Examiner* — Mohammed A Hasan
(74) *Attorney, Agent, or Firm* — Kilpatrick Townsend & Stockton LLP

(57) ABSTRACT

A system or method for measuring human ocular performance can be implemented using an eye sensor, a head orientation sensor, and an electronic circuit. The device is configured for measuring vestibulo-ocular reflex, pupillometry, saccades, visual pursuit tracking, vergence, eyelid closure, dynamic visual acuity, retinal image stability, foveal fixation stability, focused position of the eyes or visual fixation of the eyes at any given moment and nystagmus. The eye sensor comprises a video camera that senses vertical movement and horizontal movement of at least one eye. The head orientation sensor senses pitch and yaw in the range of frequencies between 0.01 Hertz and 15 Hertz. The system is implemented as part of an impact reduction helmet that comprises an inner frame having interior pads configured to rest against a person's head and one or more shock absorption elements attached between the inner frame and the spherical shell that couple the spherical shell to the inner frame. The spherical shell has a circular geometry, that when viewed horizontally at its horizontal midplane, includes a center point that is the rotational center of the spherical shell.
(Continued)

The one or more shock absorption elements are sized to provide greater spacing between the inner frame and the spherical shell at the sides and rear of the spherical shell than at the front of the spherical shell. The one or more shock absorption elements are sized to configure the alignment of the rotational center of the spherical shell with the proximate rotational center of the wearer's head.

20 Claims, 25 Drawing Sheets

Related U.S. Application Data which is a continuation-in-part of application No. 15/162,300, filed on May 23, 2016, now Pat. No. 9,788,714, which is a continuation-in-part of application No. 14/326,335, filed on Jul. 8, 2014, now Pat. No. 9,370,302, and a continuation-in-part of application No. 13/749,873, filed on Jan. 25, 2013, now abandoned.

(51) Int. Cl.
A61B 3/11 (2006.01)
A61B 5/00 (2006.01)
A61B 5/11 (2006.01)
A61B 3/00 (2006.01)
A61B 3/032 (2006.01)
A61B 3/15 (2006.01)

(52) U.S. Cl.
CPC ............ A61B 3/032 (2013.01); A61B 3/158 (2013.01); A61B 5/1103 (2013.01); A61B 5/4863 (2013.01); A61B 5/6814 (2013.01)

(58) Field of Classification Search
USPC ....................................................... 351/209
See application file for complete search history.

(56) References Cited

U.S. PATENT DOCUMENTS

| | | |
|---|---|---|
| 5,180,907 A | 1/1993 | Udden et al. |
| 5,204,998 A | 4/1993 | Liu |
| 5,550,601 A | 8/1996 | Donaldson |
| 5,555,895 A | 9/1996 | Ulmer et al. |
| 5,621,922 A | 4/1997 | Rush, III |
| 5,838,420 A | 11/1998 | MacGregor Donaldson |
| 5,919,149 A | 7/1999 | Allum |
| 5,942,954 A | 8/1999 | Galiana et al. |
| 5,953,102 A | 9/1999 | Berry |
| 5,978,972 A | 11/1999 | Stewart et al. |
| 6,301,718 B1 | 10/2001 | Rigal |
| 6,796,947 B2 | 9/2004 | Watt et al. |
| 6,826,509 B2 | 11/2004 | Crisco et al. |
| 6,931,671 B2 | 8/2005 | Skiba |
| 7,276,458 B2 | 10/2007 | Wen |
| 7,380,938 B2 | 6/2008 | Chmielewski et al. |
| 7,386,401 B2 | 6/2008 | Vock et al. |
| 7,401,920 B1 | 7/2008 | Kranz et al. |
| 7,448,751 B2 | 11/2008 | Kiderman et al. |
| 7,500,752 B2 | 3/2009 | Nashner |
| 7,509,835 B2 | 3/2009 | Beck |
| 7,526,389 B2 | 4/2009 | Greenwald et al. |
| 7,651,224 B2 | 1/2010 | Wood et al. |
| 7,682,024 B2 | 3/2010 | Plant et al. |
| 7,727,162 B2 | 6/2010 | Peterka |
| 7,731,360 B2 | 6/2010 | MacDougall et al. |
| 7,753,523 B2 | 7/2010 | Kiderman et al. |
| 7,849,524 B1 | 12/2010 | Williamson et al. |
| 7,866,818 B2 | 1/2011 | Schroeder et al. |
| 7,931,370 B2 | 4/2011 | Bartomeu |
| 7,988,287 B1 | 8/2011 | Butler et al. |
| 8,232,881 B2 | 7/2012 | Hertz |
| 8,253,814 B2 | 8/2012 | Zhang et al. |
| 8,285,416 B2 | 10/2012 | Cho et al. |
| 8,510,166 B2 | 8/2013 | Neven |
| 8,529,463 B2 | 9/2013 | Della Santina et al. |
| 8,578,520 B2 | 11/2013 | Haldin |
| 8,696,126 B2 | 4/2014 | Yoo et al. |
| 8,764,193 B2 | 7/2014 | Kiderman et al. |
| 9,370,302 B2 | 6/2016 | Krueger |
| 9,788,714 B2 | 10/2017 | Krueger |
| 10,231,614 B2 * | 3/2019 | Krueger ................ G16H 50/20 |
| 2002/0118339 A1 | 8/2002 | Lowe |
| 2006/0059606 A1 | 3/2006 | Ferrara |
| 2006/0098087 A1 | 5/2006 | Brandt et al. |
| 2006/0206175 A1 | 9/2006 | Tournier et al. |
| 2006/0270945 A1 | 11/2006 | Ghajar |
| 2008/0022441 A1 | 1/2008 | Oranchak et al. |
| 2009/0021695 A1 | 1/2009 | Scarpino |
| 2010/0036289 A1 | 2/2010 | White et al. |
| 2010/0092049 A1 | 4/2010 | Schroeder et al. |
| 2010/0101005 A1 | 4/2010 | Cripton et al. |
| 2010/0198104 A1 | 8/2010 | Schubert et al. |
| 2010/0280372 A1 | 11/2010 | Poolman et al. |
| 2011/0176106 A1 | 7/2011 | Lewkowski |
| 2011/0209272 A1 | 9/2011 | Drake |
| 2012/0133892 A1 | 5/2012 | Furman et al. |
| 2012/0143526 A1 | 6/2012 | Benzel et al. |
| 2012/0198604 A1 | 8/2012 | Weber et al. |
| 2012/0204327 A1 | 8/2012 | Faden et al. |
| 2012/0297526 A1 | 11/2012 | Leon |
| 2013/0232668 A1 | 9/2013 | Suddaby |
| 2013/0278899 A1 | 10/2013 | Waldorf et al. |
| 2014/0111771 A1 | 4/2014 | Liu |
| 2014/0192326 A1 | 7/2014 | Kiderman et al. |
| 2014/0327880 A1 | 11/2014 | Kiderman et al. |
| 2015/0038803 A1 | 2/2015 | Uhlig et al. |
| 2015/0212576 A1 | 7/2015 | Ambrus et al. |
| 2015/0223683 A1 | 8/2015 | Davidovics et al. |
| 2015/0243099 A1 | 8/2015 | Schowengerdt |
| 2015/0245766 A1 | 9/2015 | Rennaker et al. |
| 2015/0335239 A1 | 11/2015 | Macfougall |
| 2016/0033750 A1 | 2/2016 | Nunnink et al. |
| 2016/0062459 A1 | 3/2016 | Publicover et al. |
| 2016/0081546 A1 | 3/2016 | MacDougall |
| 2016/0085302 A1 | 3/2016 | Publicover et al. |
| 2016/0106315 A1 | 4/2016 | Kempinski |
| 2016/0110920 A1 | 4/2016 | Schowengerdt |
| 2016/0132726 A1 | 5/2016 | Kempinski et al. |
| 2016/0242642 A1 | 8/2016 | Migliaccio et al. |

OTHER PUBLICATIONS

Foster, "New Football Helmet Could Save the Sport", published by Popular Science, https://www.popsci.com/science/article/2013-08/helmet-wars-and-new-helmet-could-protect-us-all, Dec. 18, 2012, all pages.

* cited by examiner

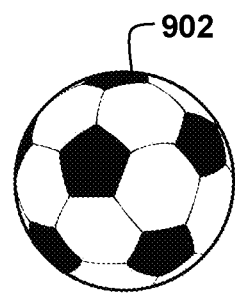
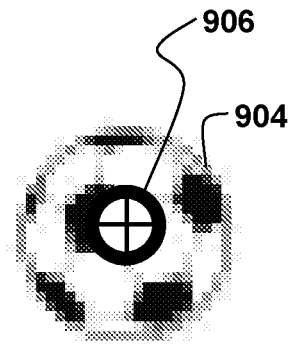
FIG. 19A                    FIG. 19B
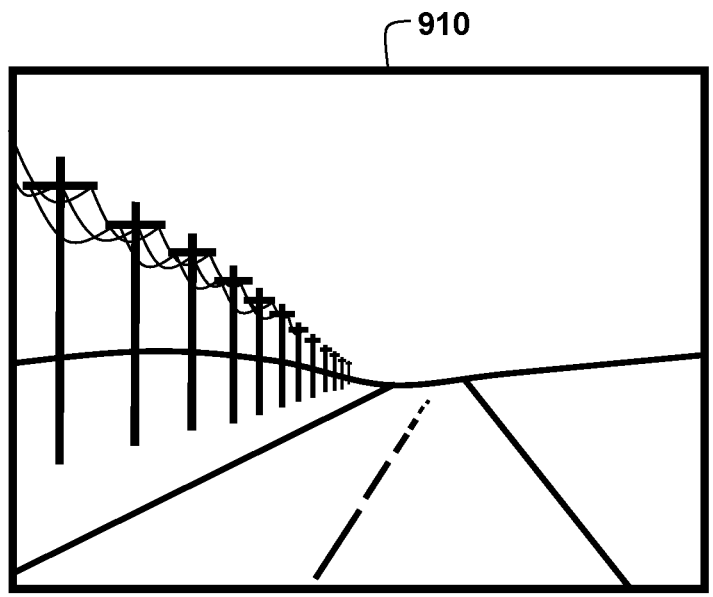
FIG. 20

OCULAR-PERFORMANCE-BASED HEAD IMPACT MEASUREMENT APPLIED TO ROTATIONALLY-CENTERED IMPACT MITIGATION SYSTEMS AND METHODS

CROSS REFERENCE TO RELATED APPLICATIONS

This application is a Continuation-In-Part of U.S. patent application Ser. No. 15/713,418, filed 22 Sep. 2017, which application is a Continuation-In-Part of U.S. patent application Ser. No. 15/162,300, filed 23 May 2016, now U.S. Pat. No. 9,788,714, issued 17 Oct. 2017, which application is a Continuation-In-Part of U.S. patent application Ser. No. 14/326,335, filed 8 Jul. 2014, now U.S. Pat. No. 9,370,302, issued 21 Jun. 2016. This application is also a Continuation-in-Part of U.S. patent application Ser. No. 13/749,873, filed 25 Jan. 2013. The entire disclosures of all of the aforementioned patents and applications are incorporated by reference herein for all purposes.

FIELD OF INVENTION

Embodiments of the invention(s) disclosed herein relate to systems and methods that use human ocular performance measurement in combination with head impact mitigation devices. Human ocular performance can be measured using vestibulo-ocular reflex, ocular saccades, pupillometry, visual pursuit tracking, vergence, eye-lid closure, focused position of the eyes, dynamic visual acuity, kinetic visual acuity, virtual retinal stability, retinal image stability, foveal fixation stability and nystagmus. Head impact mitigation devices can include impact pads, faceguards, face shields, visors, goggles, and helmets. Such head impact mitigation devices can be rotationally centered by configuring the head impact mitigation device or devices to be spherical, to be circular in one or more cross section, and/or to align concentrically with the rotational center of upper spinal cord/brainstem.

BACKGROUND

Concussions are a type of traumatic brain injury (TBI) that is sometimes called a mild traumatic brain injury or a moderate traumatic brain injury and abbreviated as an MTBI. Concussions and the resultant chronic traumatic encephalopathy (CTE) have reached epidemic proportions in the US. The CDC estimates that as many as 3.8 million sports-related concussions occur in the U.S. each year including professional athletes, amateurs of all levels, and children. There are over 250,000 emergency room visits of young people annually for head injuries from sports and recreation activities. Over 50 million Americans participate in team sports and all of them are at some level of risk of experiencing a concussion. Concussions from multiple head blows and the resulting CTE have caused several professional football players to commit suicides. The US National Football League (NFL) and the scientific community recognize that concussions are a major concern for both players and the sport itself. Concussions also occur in college and high school football, in other sports such as ice hockey and cycling, and in military operations.

Concussions happen in the brain's white matter when forces transmitted from a big blow strain nerve cells and their connections, the axons, resulting in changes to the brain such as pruning, synaptic pruning, and myelination. Linear blunt trauma can happen when falling to the ground and hitting the back of the head. The falling motion propels the brain in a straight line downward. Rotational blunt trauma can occur when a player is spun, rolled or turned with the head hitting the object. The base of the skull is rough with many internal protuberances. These ridges can cause trauma to the temporal lobes during rapid deceleration. There is a predicted intracranial pressure wave after a concussive blow with the positive pressure (coup) to negative pressure (contre-coup) occurring across the brain. A high sheer stress occurs in the central core of the brain (e.g., brainstem). Axonal injury occurs with degeneration/disintegration in discrete regions of the brain. Axon retraction and areas of hemorrhage are noted.

Diffuse axonal injury (DAI) occurs from rotational forces. The injury to tissue is greatest in areas where the density difference is greatest. For this reason, almost ⅔ of DAI lesions occur at the gray-white matter junction. Location of injury depends on plane of rotation. The magnitude of injury depends on the distance from the center of rotation, arc of rotation, duration and intensity of the force. There are widespread metabolic changes (reduced N-Acetylaspartate (NAA)/Creatine (Cr), increased Choline (Cho)/Cr, and reduced NAA/Cho ratios). Early and late clinical symptoms, including impairments of memory and attention, headache, and alteration of mental status, are the result of neuronal dysfunction. The mechanical insult initiates a complex cascade of metabolic events. Starting from neurotoxicity, energetic metabolism disturbance caused by the initial mitochondrial dysfunction seems to be the main biochemical explanation for most post-concussive signs and symptoms. Furthermore, concussed cells enter a peculiar state of vulnerability, and if a second concussion is sustained while they are in this state, they may be irreversibly damaged by the occurrence of swelling. This condition of concussion-induced brain vulnerability is the basic pathophysiology of the second impact syndrome.

Prior Art Non-Ocular Concussion Assessment Methods and Systems

Current methods concussion assessment methods and systems are inadequate. The techniques used include: (a) questioning the athlete or person about the incident; (b) a sideline test with brief neurologic exam and follow up with a clinician; and (c) transferring the patient to medical facility to perform an emergency CT or MRI scan of the head.

Following a witnessed or reported traumatic force to the head, athletes are typically evaluated on the sideline or locker room with interrogation regarding relevant symptoms. More common symptoms include headache, dizziness, difficulty with concentration, confusion and visual disturbance or photosensitivity. Many also experience nausea, drowsiness, amnesia, irritability or feeling dazed. However, none of these symptoms either alone or in combination, are specific for concussion, and frequently concussions can be undetectable by symptom screening alone. Such a sideline evaluation is suboptimal. More specific testing is not readily available for most individuals and a delayed evaluation is the norm. For those seen later by clinicians, the neurologic exam is often normal. While CT scans are effective in detecting acute brain trauma such as hematoma or edema, they are limited in detecting concussions and other concussion-related symptoms because concussions affect brain function rather than structure. Thus, functional tools, such as functional MRIs (fMRIs) need to be used.

A fMRI is a concussion diagnostic tool used by medical professionals to measure the difference between the magnetic states of oxygen-rich and oxygen-poor blood through the use of blood-oxygen-level-dependent (BOLD) contrast techniques. These scans may not be readily available at most hospitals and the use is limited.

Further, specific clinical laboratory tests with professional specialists to interpret the data are not immediately available or even accessible to some players. There are presently some tests available for concussion assessment. Both balance and gait can also be affected in the setting of concussion, and numerous sideline assessments are intended to evaluate these sensorimotor functions.

The Standardized Assessment of Concussion (SAC) is a brief cognitive test that specifically evaluates orientation, concentration, and memory. While the test is easy to administer as a sideline screening tool, it suffers from inadequate sensitivity to justify its use as a stand-alone test. Furthermore, as with symptom checklists, determined athletes can manipulate the outcome, either by memorizing certain portions of the evaluation or by intentionally underperforming in the preseason baseline assessment to which subsequent tests will be compared. It lacks validity and reliability of the data obtained.

The Balance Error Scoring System (BESS) is a static balance assessment that requires an individual to perform 3 stances on 2 different surfaces for a total of 6 trials. Each trial is 20 seconds in duration, and the score is equal to the cumulative number of balance errors. While balance itself is a relatively objective measure of sensorimotor function, significant variability in scoring is reflected by poor interrater and even intrarater reliability. An individual's score on the BESS can also fluctuate during the course of an athletic season independent of concussion status, and the BESS score can be further confounded by lower-extremity injuries and/or fatigue.

The timed tandem gait test (TGT) is a dynamic assessment of sensorimotor function in which a participant is timed while walking heel-to-toe along a 38-mm-wide piece of tape that is 3 m in length. Each assessment consists of 4 identical trials, and the best time among the 4 trials is recorded as the official score. Timed TGT performance can be affected by exercise and lacks specificity for concussions and reliability.

The Sport Concussion Assessment Tool, 3rd Edition (SCAT-3) consists of a carefully selected series of tests, including a focused physical exam, a 22-symptom checklist, the GCS, and cognitive and sensorimotor assessments. The SCAT-3 benefits from its ability to assess a range of neurological functions, including orientation, cognition, memory, balance, and gait. However, the duration of the test battery is approximately 15-20 minutes, which is not optimal in the setting of time-limited athletic competition. Furthermore, the SCAT-3 is designed to be administered by medical practitioners, which limits its utility in youth and high-school sports, in which medical professionals are not necessarily available for sideline concussion screening. Similar to many of the other concussion screening tools, the SCAT-3 also requires baseline testing for comparison, which carries additional logistical challenges. Finally, SCAT-3 is not 100% sensitive for identifying athletes with concussion and is more of a complementary test rather than the primary stand-alone tool for concussion detection. The checklist's sensitivity has been shown to have a significant degree of variability. A revised SCAT-5 incorporates cognitive and balance testing with 6 pages of forms to complete and takes more than 10 minutes to complete. This test also cannot be used as stand-alone method to diagnose concussion.

The King-Devick Test (KDT) is a rapid mobile application of visual performance measure. It takes about two minutes to complete and compares pre-test results. This is a rapid number-naming task requiring the athlete to read aloud 3 cards of irregularly spaced single-digit numbers as quickly as possible. Scoring is based on both speed and accuracy. This test does not measure eye movements such as vergence or other oculomotor parameters, such as VOR or visual pursuit. This test also cannot measure fine ocular movements such as saccades. At its core, the KDT is an assessment of visual function, but it also assesses the integrity of attention. The KDT requires a baseline assessment for comparison. In the setting of sideline concussion screening, the KDT is ideal in that it takes less than 1-2 minutes to complete but is 80%-86% sensitive for detecting concussion and thus should not be used as a stand-alone test and has testing reliability variability due to large learning effect.

Brain Scope uses commercial smartphone hardware, using an Android operating system and a custom sensor to record and analyze a patient's electroencephalogram (EEG) after head, injury. The test is based on a technique called quantitative electroencephalography, or QEEG. QEEG relies on computerized analysis of a set of changes that are distinctive of a traumatic brain injury. It requires a baseline measurement because without a baseline measurement it can't be known for sure whether someone's EEG signal is in fact abnormal. The difference could be other things besides concussion, like a medication, a previous head injury, or something else entirely. It also requires trained personnel for interpretation and is not completely portable. It has not been well accepted, is more difficult to interpret and is more time consuming.

A blood test, called the Brain Trauma Indicator (BTI), helps determine whether a CT scan is needed in people with suspected concussion. The test measures two brain-specific proteins, ubiquitin C-terminal hydrolase (UCH-L1) and glial fibrillary acidic protein (GFAP), that are rapidly released by the brain into the blood within 12 hours of serious brain injury. Test results can be available within three to four hours (or approximately 16 hours after the serious injury). Low blood levels of these proteins indicate that, if the person has damage, it is likely too small to be seen on a CT scan. Obviously, this cannot be done acutely, but has to be done in a medical facility, which may not be readily available for remote injuries. Failure to provide information immediately, may also fail to prevent second events, as the athlete or military personnel may have returned to play or previous activities.

ImPACT (Immediate Post-Concussion Assessment and Cognitive Testing) is a neurocognitive assessment administered online in a controlled environment. ImPACT has two components: baseline testing and post-injury testing, which are used in conjunction to determine if a patient can safely return to an activity. ImPACT testing is a 25 to 30-minute online test. ImPACT is designed for ages 12-59. Only licensed healthcare providers can administer and interpret post-injury test and this is not available in most cities. It therefore cannot test the individual acutely and reliability is poor.

Helmet Instrumented Telemetry (HITS), that measures the magnitude and direction of an impact to a helmet is now used in some helmets, but do not appear to be reliable predictor of concussion or concussion severity.

Prior Art Ocular Concussion Assessment Methods

The ability to track objects in the environment is an important feature for humans to interact with their surroundings. In particular, the ability to recognize the presence of an environmental hazard is directly linked to our ability to fix our gaze on a visualized target of interest, recognize the threat, and implement a plan of action. Therefore, the central nervous system (CNS) is imposed with a series of tasks and time constraints that require a harmonic integration of several neural centers located in multiple regions and linked through an efficient transmission of information. There are central nervous system (CNS) impairments in individuals with mTBIs long after the last traumatic episode. Even a mild TBI (mTBI), also known as a concussion, will result in oculomotor abnormalities and can cause visual problems, including, but not limited to dysfunction with visual fixation on a visual element or visual object of interest and vergence. In addition to glare and photophobia, individuals commonly report problems including blurred vision; squinting; double vision/diplopia; difficulty reading; watching television; using computers; loss of visual acuity; color discrimination; brightness detection; contrast sensitivity; visual field defects; visuospatial attention deficits; slower response to visual cues; visual midline shift syndrome, affecting balance and posture; impaired accommodation and convergence; nystagmus; visual pursuit disorders; deficits in the saccadic system; extraocular motility problems resulting in strabismus; reduction in stereopsis; reading problems, including losing one's place, skipping lines, and slow reading speed.

During periods of fixation, our eyes are never perfectly stable but display small involuntary physiological eye movements. These take the form of disconjugate slow drifts (1-3'/~0.05°), small conjugate microsaccades (5-10'/~0.17°, 1-2 per second) and disconjugate tremors (15"/0.004°; 30-80 Hz) superimposed on the slow drifts. A further class of involuntary physiological eye movement is called saccadic intrusions (SI). They are conjugate, horizontal saccadic movements which tend to be 3-4 times larger than the physiological microsaccades and take the form of an initial fast eye movement away from the desired eye position, followed, after a variable duration, by either a return saccade or a drift Saccadic intrusions are involuntary, conjugate movements which take the form of an initial fast movement away from the desired eye position and followed after a short duration, by either a return secondary saccade or a drift.

When analyzing eye movement accuracy, abnormal saccadic eye movements while performing smooth pursuit, diminished accuracy of primary saccadic eye movement, and a widespread slower reaction to visual stimuli can all be seen. More commonly the most relevant saccadic parameters measured are peak velocity, latency, and accuracy. Visually guided saccadic tasks showed longer latencies and reduced accuracy irrespective of the severity of TBI. There is also increased eye position error, variability, widespread delays in reaction times and significant adaptations to normal patterns of eye tracking movements. Saccadic intrusions (irregular episodic occurrences of fast eye movements) are classified according to whether or not the intrusive saccades are separated by a brief interval in which the eyes are stationary. Although saccadic reaction times appear delayed in mild TBI, they can be seen to resume to normal levels one to three weeks after injury.

Saccadic intrusions, and saccadic oscillations are fixation instabilities which impair vision, and usually are involuntary and rhythmic. Saccadic oscillations are caused by abnormalities in the saccadic eye movement system. Abnormal saccades move the eyes away from the intended direction of gaze, and corrective saccades carry the eyes back. In saccadic intrusions, such as square-wave jerks and macrosquare-wave jerks, brief pauses occur, or intersaccadic intervals, between the opposing saccades. In ocular flutter and opsoclonus, no intersaccadic intervals occur. Three of four types of SI monophasic square wave intrusions (MSWI), biphasic square wave intrusions (BSWI) and double saccadic pulses (DSP) have been noted to be exclusively saccadic, while the fourth type, the single saccadic pulses (SSP), exhibits a slow secondary component. Following mTBI the impaired ability to generate predictive (or anticipatory saccades) can also be seen. The majority of individuals have vergence system abnormalities (convergence insufficiency), which typically results in oculomotor symptoms related to reading.

Thus, the measurement of ocular performance can greatly enhance the ability to determine whether a traumatic brain injury has occurred. However, the currently available ocular performance technology is not optimized for concussion evaluation.

The EYE-SYNC System quantifies the predictive timing of dynamic visuo-motor synchronization (DVS) between gaze and target during predictive circular visual tracking. Eye-Sync utilizes a head worn goggles which measures smooth pursuit, while the head remains motionless. The test takes 1 minute, while the user visualizes a dot moving in a circle. Eye trackers measures spatial and timing variability and has 80% test reliability for detecting concussions. However, visual pursuit testing cannot test the vestibular system, which is also intimately related to concussions. It therefore lacks more sophisticated testing, such as seen with vestibular ocular reflex testing. It is also not a stand-alone device, but requires an accessory computer attached.

The Eye-Guide Focus system features an eye-tracking headset and a portable chin mount. Its software runs on an iPad facing the user and the user has to follow a small white circle moving across the screen with their eyes in order to set the baseline of how their eyes normally function. This system lacks complete portability and uses similar technology to Eye-Sync.

Neuro Kinetics I-PAS System is a battery of tests using goggles and measures ocular motor, eye motor and reaction times to test whether certain neural pathways have been altered or are behaving abnormally. I-Pass test subjects wear a pair of goggles linked to a laptop and allows the tester to measure infinitesimally small changes in the subject's eye muscles while the test is taking place. The data generated from the test, coupled with the clinical exam, allows the doctor to make a final diagnosis. (a non-portable device). This testing is performed in a clinical environment, lacks portability and multiple pieces of equipment, with medical personnel required to interpret the data obtained.

Oculogica's EyeBOX uses ocular motility to detect cranial nerve function and provides a BOX Score indicative of the presence and severity of brain injury. The EyeBOX requires no pre-test calibration which can omit critical information if the subject being evaluated has indeed suffered a TBI or concussion. This test requires the user to rest their chin and forehead comfortably on the device and watch a video for less than four minutes. This requires laboratory testing and also lacks portability.

The evidence shows that more sophisticated testing is needed which is highly specific for concussion detection, portable and can be used on the field of play, in a military operative environment or in any other environment where a concussion is likely to occur. Specifically, oculomotor parameter measurement as described with this invention using ocular and head sensing elements and transducers have shown high sensitivity and accuracy in identifying athletes who experienced a sport-related concussion. When comparing all these tests, the VOR has the highest percentage for identifying the individual with concussions.

Background Regarding Concussion Mitigation

There are different types of forces, linear and rotational acceleration which act on the brain in any physical trauma. Linear accelerations are straight-line forces that begins at the point of impact. Rotational acceleration is less intuitive. It occurs most acutely during angular impacts, or those in which force is not directed at the brain's center of gravity. With violent blows to the head there is often a combination of linear and rotational forces. Most of the blows to the head will occur off-center and therefore most of the accelerations in the head are going to be rotational. These rotational forces strain nerve cells and axons more than linear forces resulting in greater neuronal injury.

Current methods for mitigating traumatic brain injuries are limited in their effectiveness. Although helmets typically provide decent protection against linear impacts, their protection against rotational impacts is deficient. This is clearly problematic given the severity of head injuries caused by rotational impacts. There is no pharmacologic treatment for any of these injuries. For these and other reasons, new technology and concepts must be implemented to improve helmet construction for impact protection, detecting and managing concussions and protecting the brain.

Studies of head impacts in football show that concussions occur when a person receives one or more hits that induce linear head accelerations of greater than about 80 g or rotational head accelerations of greater than about 5000 rad/see. An analysis of the speed at impact shows that a world-class sprinter can run about 10 m/sec (23 miles/hour). A 4-minute mile is equivalent to 6.7 m/sec, which is about ⅔ of the speed of a world-class sprinter. Football helmet test standards use 12 mile/hour impacts, which equals approximately 5 m/sec or half of the speed of a world-class sprinter. The padding on a typical football helmet is less than 1 inch thick. From physics:

$$x = (0.5) a\ t^2$$

$v = a\ t$ (if acceleration is constant)

where: x is displacement, v=velocity, a=acceleration, and t=time

If one solves the above equations for constant deceleration from 5 m/sec to 0 m/sec in 1 inch (¹⁄₄₀th of a meter or 25 millimeters), the result is 500 m/sec² or approximately 50 g (the acceleration of gravity is approximately 10 m/sec²). This means that padding that perfectly decelerates from 5 m/sec to 0 in 25 mm (1 inch) could theoretically provide a constant deceleration rate of 50 g. However, the padding on a helmet is far from this optimum in that (a) it doesn't provide a full inch of travel in actual use and (b) it doesn't provide the constant resistive force needed for perfect linear deceleration. Furthermore, athletes may sprint at speeds that create an impact having an initial velocity of greater than 12 miles per hour. A calculation of rotational accelerations based on typical current football helmet configurations shows that a one inch of rotation of the outer shell of a 12-inch helmet to stop an initial radial velocity of 12 miles/hour (5 m/sec) at a radius of 6 inches generates an angular acceleration of about 5000 rad/sec² which is the concussion threshold as the threshold for linear acceleration (or deceleration) of the head. These theoretical calculations are consistent with the medical data that shows that concussions occur frequently in high school, collegiate, and professional football. Helmet manufacturers and the test labs understand the inability for current helmet designs to prevent concussions and place the following warning message on all football helmets sold in the USA: "No helmet can prevent all head and neck injuries a player might receive while participating in football". Many warning labels on football helmets, such as those made by Riddell, go further in their warning label and also state that: " . . . Contact in football may result in CONCUSSION-BRAIN INJURY which no helmet can prevent . . . ."

CONCLUDING SUMMARY

It is desired to provide a head impact measurement and mitigation system and/or method that is fundamentally superior to the prior art in determining whether a concussion has occurred and in reducing the chance of one or more concussions that can lead to chronic traumatic encephalopathy.

BRIEF DESCRIPTION OF THE DRAWINGS

The present invention will be better understood on reading the following detailed description of non-limiting embodiments thereof, and on examining the accompanying drawings, in which:

FIG. 19A shows an unaltered visual element;

FIG. 19B shows the visual element of FIG. 11A that has been altered by defocusing the visual element and superimposing a target;

FIG. 20 shows a scene that can be used for optokinetic testing;

Figure 1A:
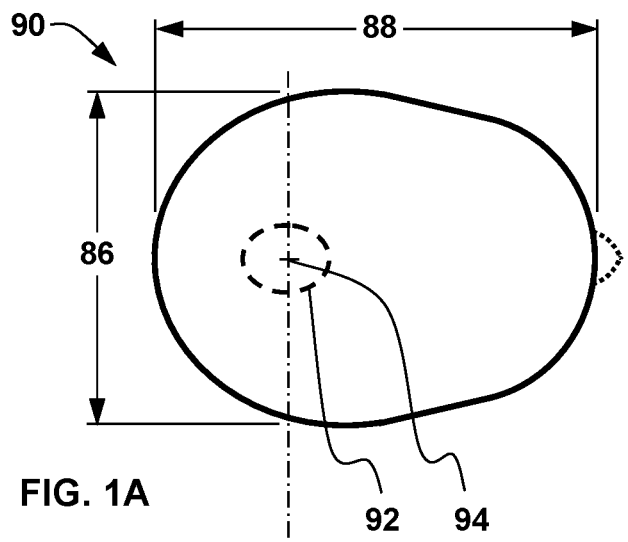
FIG. 1A shows a top view of a typical human skull.

It should be understood that the drawings are not necessarily to scale. In certain instances, details that are not necessary for an understanding of the invention or that render other details difficult to perceive may have been omitted. It should be understood that the invention is not necessarily limited to the particular embodiments illustrated herein.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It should be understood that various changes could be made in the function and arrangement of elements without departing from the spirit and scope as set forth in the appended claims.

Specific details are given in the following description to provide a thorough understanding of the embodiments. However, it will be understood by one of ordinary skill in the art that the embodiments may be practiced without these specific details.

In one embodiment, the present invention comprises head tracking and ocular-based sensors integrated into a helmet. The helmet has been configured to prevent or reduce concussions and/or traumatic brain injury. More specifically, the helmet has a spherical shape when viewing a horizontal cross-sectional plane of the helmet from above. The center of this spherical shape is aligned to be proximate to the wearers spinal cord (center of rotation of the head) when this cross-sectional horizontal plane is looked at from above. The spherical shell of the helmet is coupled to the head of the wearer with impact absorption elements that are configured to minimize the effects of tangential and axial impacts to the helmet shell on the wearer's brain. The ocular-based sensors comprise at least one camera that views at least one eye of the helmet wearer. The information from this eye camera can be combined with sensors that measure head rotation to determine whether human performance has been degraded by a blow to the head. Vestibular ocular reflex after an impact is an example of one ocular performance measurement that could be made using this system to determine if the wearer has suffered a concussion or similar injury. Other ocular performance measurements can include pupillometry, ocular saccades, visual pursuit tracking, nystagmus, vergence, convergence, divergence, eye-lid closure, dynamic visual acuity, kinetic visual acuity, retinal image stability, foveal fixation stability, and focused position of the eyes or visual fixation at any given moment. The system can include other sensors to monitor the physiologic, chemical, and/or biochemical heath of the user in real time during activity.

Embodiments of the invention could also be ocular sensor-based modules that are attached to a helmet of any configuration. Such ocular sensor-based modules could be part of a face guard, or they could be part of a face shield. Such ocular-sensor-based modules could also be attached to a head without using a helmet.

Definitions

The definitions that follow apply to the terminology used in describing the content and embodiments in this disclosure and the related claims.

A concussion is defined as an immediate and transient loss of consciousness accompanied by a brief period of amnesia after a blow to the head.

A sphere is a 3-dimensional version of a circle and has the same properties as a circle regarding (a) the distance between the center point and any point on the sphere, (b) having a constant radius of curvature, and (c) that all lines normal to a point on the sphere will go through the center of the sphere. Viewed horizontally, there is only 1 central point in a sphere. Every cross section of a sphere, whether it goes through the center or not, will be a circle. A sphere is perfectly symmetrical around its center and has the smallest surface area of any shape, given a fixed volume.

An Ellipsoid is the three-dimensional equivalent of an ellipse. A curved line forming a closed loop, where the sum of the distances from two points (foci) to every point on the line is constant. An ellipsoid has a center that is defined by the point of intersection of three pairwise perpendicular axes of symmetry. Some of these may be circles since a circle is also an ellipse. It can be defined as an elliptically shaped object having a center of rotation that is not at the same location as the center point of the elliptically-shaped object when viewed in a horizontal plane. An ellipse is always an oval, but not all ovals are ellipses. This is because an ellipse is a flat circle just like an oval, but ellipses are standard definite geometrical figures, having symmetry on two perpendicular axes.

The smart sensing process can be defined as the input energy or signal which is detected by the sensing element, where the data is measured, and the transducer and associated circuitry transfers the data as output energy or signal to other sensing elements or devices.

Linear velocity is defined as the speed and direction of a physical object that is moving in a straight line. It is the rate of change of the object's position with respect to time.

Angular velocity is defined as speed of a physical object that is moving along a circular path. The angular velocity of an object is the object's angular displacement with respect to time. Angular velocity is the rate of change of the position angle of an object with respect to time, so w=theta/t, where w=angular velocity, theta=position angle, and t=time. Angular velocity, also called rotational velocity, is a quantitative expression of the amount of rotation that a spinning object undergoes per unit time. It is a vector quantity, consisting of an angular speed component and either of two defined directions or senses. Rotation is the movement of a geometric figure about a certain point. It is a transformation in which a plane figure turns around a fixed center point. In other words, one point on the plane, the center of rotation, is fixed and everything else on the plane rotates about that point by a given angle.

The definition of inertia is that objects remain in motion or at rest unless acted on by an outside force. A body at rest would stay at rest and a body moving through space would continue moving through space unless an external force (like friction or gravity) caused it to slow down or stop.

A saccade is a fast movement of an eye, head or other part of the body or of a device. It can also be a fast shift in frequency of an emitted signal or other quick change. Saccades are quick, simultaneous movements of both eyes in the same direction. Humans do not look at a scene in fixed steadiness, the eyes move around, locating interesting parts of the scene and building up a mental, three-dimensional 'map' corresponding to the scene. When scanning the scene in front of you or reading these words right now, your eyes make jerky saccadic movements and your eyes stop several times, moving very quickly between each stop. We cannot consciously control the speed of movement during each saccade; the eyes move as fast as they can. One reason for the saccadic movement of the human eye is that the central part of the retina (known as the fovea) plays a critical role in resolving objects. By moving the eye so that small parts of a scene can be sensed with greater resolution, body resources can be used more efficiently. The saccade that occurs at the end of a head turn with someone who has an abnormal VOR is usually a very clear saccade, and it is referred to as an overt saccade. An overt saccade is indicative of abnormal semicircular canal function on the side to which the head was rotated. For example, an overt saccade after a leftwards head rotation means the left semicircular canal has a deficit. Covert saccades are small corrective saccades that occur during the head movement of a person with abnormal inner ear function. Covert saccades reduce the need for overt saccades that the end of the head movement and are more difficult to identify than overt saccades. Covert saccades are very fast. This makes them almost impossible to detect by the naked eye, and therefore sensitive eye tracking measurements are typically required to detect covert saccades. There is a rapid deceleration phase as the direction of sight lands on the new target location. Following a very short delay, large saccades are frequently accompanied by at least one smaller corrective saccade to further approach a target location. Corrective saccades can occur even if the target has been made to disappear, further supporting the projected, ballistic nature of saccadic movements. However, corrective saccades are more frequent if the target remains visible.

Saccade accuracy, amplitude, latency and velocity can be measured with oculomotor eye movements, most commonly with saccades, vergence, smooth pursuit, and vestibulo-ocular movements. Saccades can be elicited voluntarily, but occur reflexively whenever the eyes are open, even when fixated on a target. They serve as a mechanism for fixation, rapid eye movement, and the fast phase of optokinetic nystagmus. The rapid eye movements that occur during an important phase of sleep are also saccades. After the onset of a target appearance for a saccade, it takes about 200 milliseconds for eye movement to begin. During this delay, the position of the target with respect to the fovea is computed (that is, how far the eye has to move), and the difference between the initial and intended position, or "motor error" is converted into a motor command that activates the extraocular muscles to move the eyes the correct distance in the appropriate direction. The latency, amplitude, accuracy and velocity of each respective corrective saccade and latency totals and accuracy can be calculated.

Saccade accuracy refers to the eye's ability to quickly move and accurately shift from one target fixation to another. Saccade adaptation is a process for maintaining saccade accuracy based on evaluating the accuracy of past saccades and appropriately correcting the motor commands for subsequent saccades. An adaptive process is required to maintain saccade accuracy because saccades have too short a duration relative to the long delays in the visual pathways to be corrected while in flight.

Saccade amplitude refers to the size of the eye movement response, usually measured in degrees or minutes of arc. The amplitude determines the saccade accuracy. This is sometimes denoted using "gain". It is also described as the angular distance the eye travels during the movement. For amplitudes up to 15 or 20°, the velocity of a saccade linearly depends on the amplitude (the so-called saccadic main sequence). Saccade duration depends on saccade amplitude. In saccades larger than 60 degrees, the peak velocity remains constant at the maximum velocity attainable by the eye. In addition to the kind of saccades described above, the human eye is in a constant state of vibration, oscillating back and forth at a rate of about 60 Hz.

Saccade velocity is the speed measurement during the eye movement. High peak velocities and the main sequence relationship can also be used to distinguish micro-/saccades from other eye movements like (ocular tremor, ocular drift and smooth pursuit).

Saccade latency is the time taken from the appearance of a target to the beginning of an eye movement in response to that target. Disorders of latency (timing) can be seen with saccades, VOR and visual pursuit.

Saccadic Inhibition. Studies of eye movements in continuous tasks, such as reading, have shown that a task-irrelevant visual transient (for example a flash of a portion of the computer display) can interfere with the production of scanning saccades. There is an absence or near-absence of saccades initiated around 80-120 ms following the transient. This inhibitory effect (termed saccadic inhibition SI) is also observed in simple saccade experiments using small visual targets and it has been suggested that SI may be like, or underlie, the remote distractor effect.

Visual pursuit means the movement of the eyes in response to visual signals. Smooth pursuit eye movements allow the eyes to closely follow a moving object. It is one of two ways that humans and other visual animals can voluntarily shift gaze, the other being saccadic eye movements. Pursuit differs from the VOR, which only occurs during movements of the head and serves to stabilize gaze on a stationary object. Most people are unable to initiate pursuit without a moving visual signal. The pursuit of targets moving with velocities of greater than 30°/s tend to require catch-up saccades. Most humans and primates tend to be better at horizontal than vertical smooth pursuit, as defined by their ability to pursue smoothly without making catch-up saccades. Most humans are also better at downward than upward pursuit. Pursuit is modified by ongoing visual feedback. Smooth pursuit is traditionally tested by having the person follow an object moved across their full range of horizontal and vertical eye movements.

Visual pursuit tracking can be defined as measuring a person's eye movement ability to match a visual element or visual target of interest movement. Visual pursuit eye movements utilize some of the vestibulo-ocular reflex pathways and require a visual input to the occipital cortex to permit locking of the eyes onto a visual element, visual object or target of interest. Pursuit movements are described to be voluntary, smooth, continuous, conjugate eye movements with velocity and trajectory determined by the moving visual target. By tracking the movement of the visual target, the eyes maintain a focused image of the target on the fovea. A visual stimulus (the moving visual target) is required to initiate this eye movement. Pursuit gain, which is the ratio of eye velocity to target velocity, is affected by target velocity, acceleration and frequency. Visual pursuit tracking may be related to factors that are difficult to quantify, such as the degree of alertness present in persons, visual acuity or the visibility of the pursuit target.

Visual pursuit tracking can be decayed with alcohol, centrally acting medications such as anticonvulsants, minor tranquilizers, preparations used for sleep. It is also clear that visual pursuit performance declines with age and can be adversely affected by vestibular dysfunction, central nervous system disorders and trauma, such as concussions and traumatic brain injury (TBI).

Visual pursuit accuracy is defined by the ability of the eyes to closely follow a moving object. The pursuit of targets moving with velocities of greater than 30°/s tends to require catch-up saccades. Smooth pursuit accuracy represents how closely the percentage of time the smooth pursuit velocity value remains within the target velocity value.

Visual pursuit movements are much slower tracking movements of the eyes designed to keep the moving stimulus on the fovea. Such movements are under voluntary control in the sense that the observer can choose whether to track a moving stimulus. Although it may appear that our eyes are not moving when we fixate an object, in fact they are in continual small-scale motion, showing irregular drift and tremor, interspersed by miniature saccadic movements (less than 0.5 degrees). These fixational eye movements are essential to prevent our visual percept from fading. Pursuit consists of two phases—initiation and maintenance. Measures of initiation parameters can reveal information about the visual motion processing that is necessary for pursuit.

Visual pursuit acceleration—this is the rate of change of the eye velocity. The first approximately 20 milliseconds of pursuit tends to be the same regardless of target parameters. However, for the next 80 milliseconds or so, target speed and position have a large effect on acceleration.

Visual pursuit velocity—After pursuit initiation, speed of the eye movement (velocity) usually rises to a peak and then either declines slightly or oscillates around the target velocity. This peak velocity can be used to derive a value for gain (peak velocity/target velocity). It is usually near the velocity of the target. Instead of using peak velocity, it is also sometimes of interest to use measures of velocity at times relative to either target appearance or pursuit initiation. Eye velocity up to 100 milliseconds after target appearance can be used as a measure of prediction or anticipation. Velocity measured 100 milliseconds after pursuit begins reveals something about the ability of pursuit system in the absence of visual feedback.

Visual pursuit latency is defined by the time from target appearance to the beginning of pursuit. The difficulty here is defining when pursuit begins. Usually it is measured from traces of eye velocity. It is often calculated by finding the intersection between two regression functions one fitted to velocity about the time of target appearance, and the second fitted over the initial part of the pursuit response.

Pupillometry refers to an objective way of measuring pupil size, and more specifically, the diameter of the pupil. Often pupil parameters are measured including: maximum, minimum and final pupil diameter, latency, amplitude and peak and average constriction and dilation velocities under numerous stimulus conditions including: dim pulse, dim step, bright pulse, bright step, bright red step and bright blue step. It has been observed that concussions and mild traumatic brain injury adversely affects the pupillary light reflex suggesting an impairment of the autonomic nervous system. Quantitative pupillary dynamics can also serve as an objective mild traumatic brain injury biomarker and these pupillary measurements can be reliably replicated. Quantitative pupillometry can be a measure of concussion analysis and associated with intracranial pressure.

Nystagmus is a description of abnormal involuntary or uncontrollable eye movement, characterized by jumping (or back and forth) movement of the eyes, which results in reduced or limited vision. It is often called "dancing eyes". Nystagmus can occur in three directions: (1) side-to-side movements (horizontal nystagmus), (2) up and down movements (vertical nystagmus), or (3) rotation of the eyes as seen when observing the front of the face (rotary or torsional nystagmus).

Vergence is the simultaneous movement of both eyes in opposite directions to rapidly obtain or maintain single binocular vision or ocular fusion, or singleness, of the object of interest. It is often referred to as convergence or divergence of the eyes, to focus on objects that are closer or further away from the individual. The maintain binocular vision, the eyes must rotate around a vertical axis so that the projection of the image is in the center of the retina in both eyes. Vergence measurements can easily be performed. Normally, changing the focus of the eyes to look at an object at a different distance will automatically cause vergence and accommodation, known as accommodation-convergence reflex. Convergence is the simultaneous inward movement of both eyes toward each other, usually to maintain single binocular vision when viewing an object. Vergence tracking occurs in the horizontal, vertical, and/or cyclorotary dimensions. Vergence requires that the occipital lobes be intact, and the pathway involves the rostral midbrain reticular formation (adjacent to the oculomotor nuclei) where there are neurons that are active during vergence activities. It comprises a complex and finely tuned interactive oculomotor response to a range of sensory and perceptual stimuli. There is an important interaction between the vergence system and vestibular (inner ear balance) system. To keep the eyes focused on a visual element or object of interest, while the head is moving, the vestibular system senses head rotation and linear acceleration, and activates the eyes to counterrotate to keep gaze constant even though the head is moving. As an example, this is what enables us to see a tennis ball while moving our head. The problem becomes more difficult at near vision, because the eyes are not located at the center of rotation of the head, but rather are about 10 cm anterior to the axis of rotation. Therefore, when a person is focused on a near target (such as 10 cm away), the amount of eye movement needed to keep the target fixated is much greater than the amount needed to view a similar object 100 cm away. This additional eye movement is supplied by the otoliths (linear acceleration sensing element) that produce eye movement that are roughly inversely proportional to the distance of the target from the center of the eye. Persons with disorders of their otoliths, might reasonably have a selective problem with stabilizing their vision while the head is moving, at near vision. Vergence can be also be adversely affected by other factors including aging, visual abnormalities, concussion and traumatic brain injury (TBI).

Vergence eye movements are used to track objects that move in depth in one's binocular visual field to attain and maintain a fused and single percept. When we shift our gaze from a far object to a near object, our eyes converge, the lenses of our eyes modify their focus (accommodate), and our pupils often constrict. These three combined responses are termed the near triad. convergence is the simultaneous inward movement of both eyes toward each other, usually in an effort to maintain single binocular vision when viewing an object. This is the only eye movement that is not conjugate, but instead adducts the eye—divergence is the simultaneous outward movement of both eyes away from each other, usually in an effort to maintain single binocular vision when viewing an object. It is a type of vergence eye movement. The mechanism and control of vergence eye movements involves complex neurological processes that may be compromised in individuals with traumatic brain injury, thus frequently resulting in a wide range of vergence dysfunctions and related near-work symptoms, such as oculomotor-based reading problems. The key pathologic feature of TBI is DAI, also known as a diffuse axonal shear injury, caused by shear-strain injury from rotational acceleration forces. These shear-related injuries commonly occur at the white-gray matter junction, corpus callosum, and superior colliculi, as well as other brain regions. It has been determined that 90 percent of patients have oculomotor dysfunctions encompassing vergence, accommodation, version, strabismus, and cranial nerve palsy in individuals with mTBI and reporting vision-based symptoms. A vergence system abnormality being the most common dysfunction.

The dynamic visual acuity (DVA) can be used interchangeably with kinetic visual acuity (KVA) as they both have the same meaning. In this document, DVA will be used to assess impairments in a person's ability to perceive objects accurately while actively moving the head, or the ability to track a moving object. It is an eye stabilization measurement while the head is in motion. In normal individuals, losses in visual acuity are minimized during head movements by the vestibulo-ocular system that maintains the direction of gaze on an external target by driving the eyes in the opposite direction of the head movement. When the vestibulo-ocular system is impaired, visual acuity degrades during head movements. The DVA is an impairment test that quantifies the impact of the vestibulo-ocular system pathology on a user's ability to maintain visual acuity while moving. Information provided by the DVA is complementary to and not a substitute for physiological tests of the VOR system. The DVA quantifies the combined influences of the underlying vestibulo-ocular pathology and the person's adaptive response to pathology. DVA testing is sometimes obtained for those persons suspected of having an inner ear abnormality. Abnormalities usually correlate with oscillopsia (a visual disturbance in which objects in the visual field appear to oscillate or jump while walking or moving). Currently with DVA testing, worsening of visual acuity by at least three lines on a visual acuity chart (e.g., Snellen chart or Rosenbaum card) during head turning from side to side at 1 Hz or more is reported as being abnormal. In normal individuals, losses in visual acuity are minimized during head movements by the vestibulo-ocular system that maintains the direction of gaze on an external target by driving the eyes in the opposite direction of the head movement When the vestibular system is impaired, visual acuity degrades during head movements. Individuals with such ocular performance deficits can improve their dynamic acuity by performing rapid "catch-up" saccadic eye movements and/or with predictive saccades.

Dynamic visual stability (DVS) and retinal image stability (RIS) can be used interchangeably. In this document, DVS will be used to describe the ability to visualize objects accurately, with foveal fixation, while actively moving the head. When the eye moves over the visual scene, the image of the world moves about on the retina, yet the world or image observed is perceive as being stable. DVS enables a person to prevent perceptual blurring when the body moves actively. The goal of oculomotor compensation is not retinal image stabilization, but rather controlled retinal image motion adjusted to be optimal for visual processing over the full range of natural motions of the body or with head movement. Although we perceive a stable visual world, the visual input to the retina is never stationary. Eye movements continually displace the retinal projection of the scene, even when we attempt to maintain steady fixation. Our visual system actively perceives the world by pointing the fovea, the area of the retina where resolution is best, towards a single part of the scene at a time. Using fixations and saccadic eye movements to sample the environment is an old strategy, in evolutionary terms, but this strategy requires an elaborate system of visual processing to create the rich perceptual experience. One of the most basic feats of the visual system is to correctly discern whether movement on the retina is owing to real motion in the world or rather to self-movement (displacement of our eyes, head or body in space). The retinal image is never particularly stable. This instability is owing to the frequent occurrence of tremors, drifts, microsaccades, blinks and small movements of the head. The perceptual cancellation of ocular drift appears to primarily occur through retinal mechanisms, rather than extra-retinal mechanisms. Attention also plays a role in visual stability, most probably by limiting the number of items that are fully processed and remembered.

Foveal Fixation Stability (FFS) refers to the ability to maintain an image on the fovea, which is crucial for the visual extraction of spatial detail. If the target image moves 1° from foveal center, or if random movement of the image on the fovea exceeds 2°/sec, visual acuity degrades substantially. Either of these conditions may occur if deficiencies in oculomotor control compromise the ability to maintain target alignment within these limits. Many aspects of oculomotor function do change with age. For example, smooth pursuit movements slow with age, and the range of voluntary eye movements becomes restricted, especially for upward gaze. DVA, FFS, and the vestibulo-ocular reflex decline with age.

Foveated rendering is a process which renders most of the view into a virtual world at lower resolution except for the exact area directly in front of where the user's eye is pointed. That area in front of the eye—where humans perceive the greatest detail—is rendered at a higher resolution.

Focused position of the eyes can be defined as the position or orientation of the eyes to provide a clear image of a visual element or visual object/target of interest on the fovea.

Basic Science: Concussion and Traumatic Brain Injury (TBI)

Broadly speaking, a concussion, the most common type of traumatic brain injury, results from impact or impulsive forces to the head, neck or face and typically affects the central nervous system and the peripheral vestibular system. Most concussions meet criteria for mild traumatic brain injury. Mild traumatic brain injury (mTBI) has been defined as loss of consciousness less than 30 minutes and less than 24 hours and no skull fracture. A moderate TBI has a loss of consciousness greater than 30 minutes and less than 24 hours, with or without skull fracture. Severe TBI is characterized by loss of consciousness greater than 24 hours, with contusion, hematoma or skull fracture.

Due to the variability and subtlety of symptoms, concussions may go unrecognized or be ignored, especially with the pressure placed on athletes to return to competition. There is public consensus that undiagnosed, and therefore untreated, concussions represent a significant long-term health risk to players.

Closed head injury can cause several different types of brain injury including coup, contre-coup, acceleration-deceleration trauma, rotational trauma and molecular commotion. Acceleration-deceleration trauma causes discrete lesions which affect only certain areas of the brain. Both rotational trauma and molecular commotion cause diffuse damage that impairs many aspects of brain functioning. Acceleration-deceleration trauma occurs when the head is accelerated and then stopped suddenly, as with players colliding, which can cause discrete, focal lesions to two areas of the brain. The brain will suffer contusions at the point of direct impact and at the site directly opposite the point of impact due to the oscillation movement of the brain within the skull (e.g., coup or site of contact and contrecoup or opposite site of contact respectively). Trauma results from the oscillation (bouncing) of the brain against bony projections on the inside of the skull. Brain injuries may also occur as a result of acceleration-deceleration trauma unaccompanied by impact. The prefrontal areas and the anterior portion of the temporal lobes are the parts of the brain most often affected by acceleration-deceleration trauma. Thus, if the brain is repeatedly propelled against the front part of the skull, there is likely to be major injuries. Rotational trauma occurs when impact causes the brain to move within the cranium at a different velocity than the skull. This results in a shearing of axons within the upper spinal cord, brainstem and midbrain. Because this type of injury damages neural connections rather than gray matter, it can affect a wide array of cerebral functions and should therefore be considered a type of diffuse injury. Molecular commotion is a disruption in the molecular structure of the brain which may cause permanent changes in both white and gray matter. This type of diffuse brain injury may occur in the absence of discrete lesions.

The major effects of trauma on the brain can be divided into two categories: primary and secondary (or late) effects. The primary effects are those that are caused directly by the head trauma and include concussion, contusion, and laceration of the central nervous system.

Concussion is a reversible state of diffuse cerebral dysfunction associated with a transient alteration in consciousness. Most often there is a brief period of loss of consciousness. However, athletes may be only severely stunned or dazed. Typically, there is loss of memory for recent events (retrograde amnesia), and this may extend for some seconds or minutes prior to the injury and, rarely, with more severe impact, for days or more. A variable period of inability to learn new material (anterograde amnesia) typically follows recovery of consciousness and may be dense enough to leave the individual with no memory of early post injury occurrences. Rarely, some players are unable to remember ongoing occurrences. The retrograde amnesia is presumed to be caused by a mechanical distortion of neurons, probably in the temporal lobes, which consolidate the memory trace. The anterograde amnesia is presumed to be the result of distortion of the mesial temporal-limbic circuits known to be necessary for learning.

The underlying pathophysiology of concussion appears to be a shearing effect. Rapid displacement of the head, in either acceleration or deceleration injury, causes a swirling of the cerebrum within the cranium, and shearing forces play most markedly at the junctions between brain tissues of different density and location. Rotational injuries may be particularly damaging, since the brain stem torques while there is a lot of inertia against the rotation of the cerebral cortex. This results in torsion of the nerve fibers in the core of the brain (i.e., the reticular activating system). Another major zone of diffuse axonal injury is the interface between gray and white matter. It is here and in the core of the rostral brain stem that microscopic evidence of ruptured axons can be found pathologically. It is not surprising that the athlete's resistance to future concussion tends to decline with repeated concussions or that repeated concussion may lead to dementia.

Contusions of the brain are bruises usually associated with more severe trauma than necessary for concussion. They are most prominent at the summits of gyri, the cerebral poles (particularly the frontal poles and the anterior temporal lobe), and portions of the brain stem. All these regions lie close to the bony and dural surfaces of the cranial cavity. They may directly underlie the site of the violent blow to the cranium or may be opposite the site of impact (contrecoup). The contusions can usually be seen acutely on CT or Mill scans.

Laceration of the brain usually follows cranial trauma severe enough to cause fracture of the skull and penetrating injury to the brain by skull fragments or foreign objects. However, fracture of the skull need not be associated with laceration or contusion or major concussion. On the other hand, laceration may on occasion occur with severe shearing forces unassociated with fracture. Usually some form of hemorrhage (intracerebral, subdural, epidural) is associated with laceration.

The secondary effects of cranial trauma that may further compromise brain function are edema, hypoxia, hemorrhage, infection and epilepsy. Edema may be the result of diffuse shearing of capillary, glial, and neuronal membranes or may be secondary to local contusion or laceration. Edema can generate local pressure that can compromise both arterial and venous cerebral blood flow, causing ischemia and more edema. This may precipitate a vicious cycle sometimes impossible to reverse. The mass effect of edema, focal or diffuse, can cause rostrocaudal brain stem deterioration (possibly with herniation), a major cause of delayed death from head trauma. Increased intracranial pressure ICP), mostly due to edema but added to by any intracranial bleeding, is a major cause of secondary injury. High pressure decreases the perfusion pressure in brain blood vessels (since the perfusion pressure is the mean arterial pressure minus the intracranial pressure). If this is too low, there will be further damage to neural tissue due to ischemia, which will result in further edema and an even greater increase in pressure.

Intracranial hemorrhage, arterial or venous, intra- or extracerebral, is a frequent sequela of cranial trauma and may be great enough to cause rostrocaudal deterioration of neural function and death if not recognized and attended to immediately. Rostrocaudal deterioration, if rapid, may itself cause hemorrhage by downward stretching and tearing of the paramedian penetrating arteries of the midbrain and pons. Subdural and epidural hematomas both can be treated via surgical intervention, which can be curative if undertaken prior to irreversible brain damage. Both epidural and subdural hematoma are extracerebral. For this reason, and because they are soft masses, there tends to be relatively little effect on the underlying and compressed cerebral hemispheres. However, due to distortion of the brain itself, secondary rostrocaudal distortion of the brain stem is the process that usually gives rise to the major clinical signs: depression of consciousness (reticular formation), hemiparesis (cerebral peduncles), eye signs (third and sixth nerves), and respiratory pattern abnormalities.

Herniation, the process of squeezing brain tissue from one intracranial compartment into another, is often the terminal occurrence since this produces permanent damage in the region of herniation.

Epidural hematomas are most often arterial. They are usually the result of transection of the middle meningeal artery by a skull fracture that passes through the middle meningeal groove. It must be emphasized, however, that fracture is not necessary since the skull has elasticity that may permit the violent blow to rupture the artery which is pinned between the dura matter and the skull. Because of the location of the middle meningeal artery, the clots typically lie over the lateral hemisphere (temporal and/or parietal lobes). Since the epidural hematoma is under arterial pressure, it typically continues to grow unless evacuated. However, because the dura is adhered to the inside of the skull, and since the clot is between these layers, the growth of the clot is over hours. The typical middle meningeal artery epidural hematoma is associated with a syndrome that appears within hours of the injury.

Classically, trauma is associated with a concussive loss of consciousness. The athlete may awaken from this to achieve a good level of consciousness (lucid interval) only to lose consciousness again from brain stem distortion caused by the clot growth. If the bleeding is very severe there is no lucid interval. The individual does not have time to awaken from the concussion before compressive brain stem deterioration begins. Surgical evacuation is critical. Less often, epidural collections may be the results of tears in the venous sinuses or leakage from the diploic veins. These hemorrhages may occur over any portion of the hemispheres or in the posterior fossa and are much slower.

A subarachnoid hemorrhage (SAH) involves bleeding into the space between the surface of the brain (the pia mater) and the arachnoid, one of three coverings of the brain. Strengthening rod-like fibers known as fibrous trabeculae cross through the subarachnoid space to connect the arachnoid membrane to the pia mater, and cerebrospinal fluid fills the cavity to flow around the brain. The subarachnoid space also contains the blood vessels which supply the brain and spinal cord with blood and oxygen. This cavity helps to cushion the brain to protect it from injury and continues down the spinal column along with the arachnoid membrane. The hemorrhage is presumed to arise from angular forces that cause shearing of vessels as acceleration/deceleration movement of the brain occurs with linear/tangential/rotational injuries. The bridging veins tend to shear where they enter the dura after passing through the thin subdural space between the dura and arachnoid. Symptoms associated with traumatic subarachnoid hemorrhage may or may not resemble those associated with spontaneous hemorrhage, as trauma can involve multiple injuries with overlapping symptoms. Because the blood is under very low pressure (being from veins) the hematoma tends to collect slowly, causing signs and symptoms that develop over days to months. Head trauma that can be so minor that it is not remembered may result in a subdural hematoma under these circumstances. Acute subdural hematomas are seen less frequently. They are usually associated with head trauma severe enough to cause skull fracture and cerebral contusion or laceration. Epidural hematoma and intracerebral hematoma are frequently associated. The mortality is extremely high, and the residual dysfunction of survivors is severe.

Arterial dissection may affect the carotid or vertebral arteries. This is usually associated with a tear in the intimal lining of the artery and an accumulation of blood in the media. Stroke may result from blockage of the artery or its branches or from artery-to-artery emboli arising from the site of vessel damage. The weakened artery may also rupture (often into the subarachnoid space) with potentially catastrophic results.

Pathologic Findings in the Brain with Trauma

Impact forces may cause linear, rotational, or angular movements of the brain, and more commonly a combination of these movements. In rotational movement, the head turns around its center of gravity, and in angular movement it turns on an axis not through its center of gravity. The amount of rotational force is thought to be the major component in concussion and its severity. As the angular acceleration increases, the risk of mild traumatic brain injury increases respectively.

The parts of the brain most affected by rotational forces are the midbrain and diencephalon. It is thought that the forces from the injury disrupt the normal cellular activities in the reticular activating system located in these areas, and that this disruption produces the loss of consciousness often seen in concussion. Other areas of the brain that may be affected include the upper part of the brain stem, the fornix, the corpus callosum, the temporal lobe, and the frontal lobe. Severe centrifugal forces exert tremendous shearing pressures on the brainstem and upper spinal cord. A form of neurodegeneration reported in professional football players is "Chronic Traumatic Encephalopathy" (CTE). In addition to football players, CTE has been reported in other athletes involved in violent blows to the head, in traumatic military activities and in a few non-athletes with a history of TBI.

The syndrome of CTE begins insidiously, usually many years after the individuals have stopped playing sports or their other activities, with inattention, mood and behavior disturbances, confusion, and memory loss, and progresses inexorably over many years to a stage of full-blown dementia and parkinsonism. The brain, in CTE, shows atrophy, dilatation of the lateral and third ventricles, and thinning of the corpus callosum. Microscopic examination reveals hyperphosphorylated tau (p-tau) deposition in neurons, astrocytes, and cell processes around small vessels. These changes are patchy and affect the deeper parts of cerebral sulci. Other neurodegenerative pathologies, including beta amyloid deposition in the form of diffuse or neuritic plaques, amyloid angiopathy, TDP-43-inclusions may co-exist with p-tau deposition. Tau deposition is the key cellular change in CTE. The cause of CTE is thought to be TBI, especially repeated cerebral concussions and sub-concussive trauma. In the acute phase, concussion, especially following side-to-side hits to the head, causes diffuse axonal injury (DAI) and triggers the release of tau and beta amyloid in the brain. This, along with cerebral hypoxia, excitotoxicity and inflammatory mediators, set in motion a progressive destructive cascade that causes neurodegeneration many years later.

Diffuse axonal injury (DAI) is a special traumatic lesion, which occurs following blows to the unsupported head. During such injuries, the cerebrum goes into a back and forth gliding motion, pivoting around the brainstem. The brainstem, together with the cerebellum, is held firmly fixed by the tentorium, and the falx prevents side-to-side motion. Axons are stretched but do not snap from this injury. Their sudden deformation causes changes in the axonal cytoskeleton (compaction of neurofilaments, fracture of microtubules) that lead to an arrest of the fast axoplasmic flow. Components of this flow, including mitochondria and other organelles, accumulate proximal to the lesion and cause axonal swellings (spheroids). Some axons with mild lesions probably recover but many eventually rupture. It takes several hours from trauma to axonal rupture. Influx of calcium through the stretched axolemma probably initiates the process that leads to the formation of spheroids. Mitochondrial dysfunction and neuroinflammation contribute to the local tissue injury. Ruptured axons undergo Wallerian degeneration leading to loss of neurological function. Loss of axons may lead to dying back of neurons. Thus, DAI is a multifaceted process that evolves over time. The swellings are located at nodes of Ranvier where the axolemma is more liable to deform because there is no myelin. Brain damage is most severe along midline structures (corpus callosum, brainstem) where the shear forces are greatest, and at the cortex-white matter junction because of the change in the consistency of brain tissue. Cerebral concussion is thought to be a mild form of DAI without permanent pathology. The loss of consciousness in concussion is probably due to a functional disturbance of the reticular activating substance of the brainstem. This is part of the central nervous system that is subjected to the highest twisting force during sagittal rotation of the hemispheres.

Anatomy and Biophysical Properties Supporting Impact Mitigation Functionality

For reference, FIG. 1A shows a top view of a typical human skull at 90. The shape of a normal human skull, as seen in a horizontal planar view from the top, is elliptical, not spherical. More specifically, it is egg-shaped in that it comprises a roughly circular (or spheroid in three dimensions) back side that is joined to a longer prolate circle (or prolate spheroid in 3D) front side. A human skull has a ratio of breadth, shown at 86, to length, shown at 88, that is not 1:1 and is typically 3:4 when viewed in the horizontal (also known as axial or transverse plane) plane (i.e., the horizontal midplane of a spherical helmet). The shape and size of the human skull will vary depending on race, gender, and other factors. Various measurements are used to determine head size differences. For example, the distance from the glabella (smooth part of the forehead above and between the eyebrows) to the back of the head may vary in men from 18.3 to 21.7 cm with the average being 20.0 cm. Often the skull measurement is referred to as the Cephalic index, which is the ratio of head width expressed as a percentage of head length. The normal range is 76-80.9%. Head length is measured between the glabella (the most prominent point on the frontal bone above the root of the nose) and the most prominent part of the occiput in the midline. Long headed skulls (Dolichocephalic) have a cephalic index of 70-74.9, average skulls (Mesaticephalic) are in the range of 75-79.9 and more rounded shaped skulls (Brachycephalic) are 80 or greater.

Figure 1B:
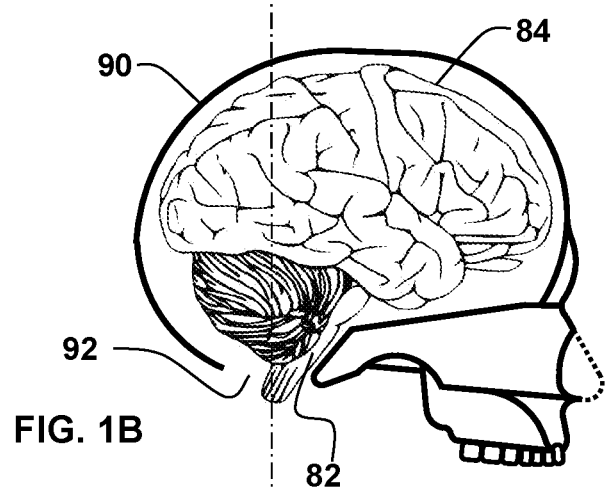
FIG. 1B shows a sagittal section view of the skull of FIG. 1A.

FIG. 1B shows a vertical side section view of the skull 90 of FIG. 1A, as well as parts of the brain. Within the bony skull 90, the cerebral cortex, 84, is the largest region of the cerebrum in the human brain and plays a key role in memory, attention, perception, cognition, awareness, thought, language, and consciousness. The cerebral cortex 84, is the most anterior (rostral) brain region and consists of an outer zone of neural tissue called gray matter, which contains neuronal cell bodies. Sitting between the cerebral cortex and the brain stem 82, is another segment of the brain, called the diencephalon, which combines the functions of the brain stem with the cerebral cortex. It is the posterior part of the forebrain that connects the midbrain with the cerebral hemispheres, encloses the third ventricle, and contains the thalamus and hypothalamus. The brainstem 82, is the region of the brain that connects the cerebrum with the spinal cord. It consists of the midbrain (superiorly located), the pons and medulla oblongata (inferiorly located). Motor and sensory neurons travel through the brainstem 82, allowing for the relay of signals between the brain and spinal cord. The cranial nerves are found in the brainstem 82. The brainstem 82, controls motor control signals sent from the brain to the body. This brain region also controls life supporting autonomic functions for the peripheral nervous system. The fourth cerebral ventricle located also in the brainstem, posterior to the pons and medulla oblongata. This cerebrospinal fluid-filled ventricle is continuous with the cerebral aqueduct and the central canal of the spinal cord. The spinal cord is the most important structure between the body and the brain. The spinal cord extends from the foramen magnum where it is continuous with the medulla to the level of the first or second lumbar vertebrae. It is a vital link between the brain and the body, and from the body to the brain. The spinal cord is 40 to 50 cm long and 1 cm to 1.5 cm in diameter. Two consecutive rows of nerve roots emerge on each of its sides. These nerve roots join distally to form 31 pairs of spinal nerves.

Figure 1C:
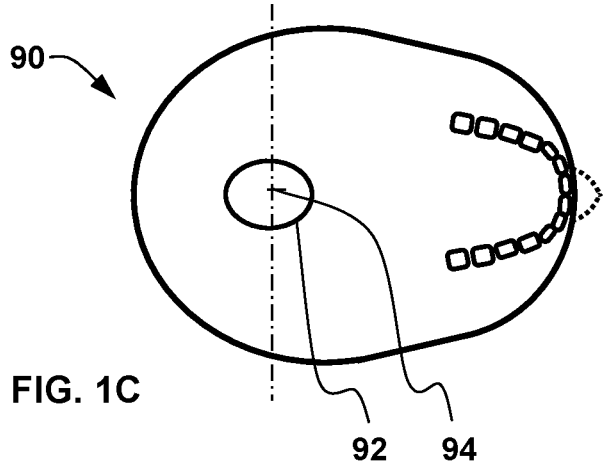
FIG. 1C shows a bottom view of the skull of FIG. 1A.

For reference, FIG. 1C shows a bottom view of the skull 90 of FIG. 1A. The foramen magnum 92, is located at the base of the skull in a posterior position. It is the largest foramen (bone aperture) in the skull base and the passage through which the spinal cord exits the cranial vault. The foramen magnum 92, is situated posteriorly in the occipital bone, and forms around the base of the brainstem (the medulla oblongata), separating the brain above from the spinal cord below. It is somewhat ovoid in shape and can vary in size and position in the posterior fossa, depending on race and sex. The foramen magnum 92, has also been identified by hidden (dotted) lines in FIG. 1A. The center of the foramen magnum 92, when seen from below, is in a plane just posterior to the mastoid tips on each side of the foramen. When viewed laterally, in the mid-sagittal plane, the center of rotation of a person's head occurs just posterior to the plane between the mastoid tips and medially at the center of the foramen magnum 92, i.e., at the point labeled 94 in FIG. 1A and FIG. 1B. FIG. 1A, FIG. 1B, and FIG. 1C have all been aligned so this center of rotation of the head falls on the same centerline. The mid-sagittal plane is equivalent to the horizontal midplane at the level of the foramen magnum 92. Seen laterally, the mid-sagittal plane is equivalent to the midplane of a spherical helmet when worn normally by a person.

In FIG. 1B, the foramen magnum 92, can be seen in the lowest part of the posterior fossa of the skull. It is in the foramen magnum area, 92, where the lower portion of the brainstem 82, (e.g., medulla oblongata) meets the upper spinal cord. The upper part of the spinal cord and medulla oblongata end on ventral wall of the $4^{th}$ ventricle. The obex is the point in the human brain at which the fourth ventricle narrows to become the central canal of the spinal cord. It occurs at the level of the foramen magnum 82, and is therefore considered the point where the medulla becomes the spinal cord. The spinal cord is the most important structure between the body and the brain. The spinal cord extends from the foramen magnum where it is continuous with the medulla to the level of the first or second lumbar vertebra Referring to FIG. 1A, FIG. 1B, and FIG. 1C, the center of rotation of a human's head 94, occurs at bottom of the skull 90, specifically in the region of the foramen magnum 92, through which nervous tissue and support cells of the upper spinal cord ascends to meet the brain stem 82, at the medulla oblongata. It is in this area (e.g., the center of the foramen magnum 92, or obex), defined as the pivot point 94, around which the brain rotates upon receiving a head impact. Because the position of the foramen magnum, 92, is more posteriorly located in the skull base, it is functionally beneficial align the center of the helmet or head worn protection system proximate over the center of rotation or the pivot point of the brain, specifically in the region of the upper spinal cord and brainstem junction (e.g., obex), at the foramen magnum. The least concussive effect can be achieved by this proximate alignment of the rotational center of a circular helmet with the center of rotation of a human's head. The center of rotation of a human's head is not at the same location as the center of the gravity of the brain.

As will be discussed further, head impacts can be linear or tangential, but most often are comprised of both. It has been established that the greatest injuries to the head, resulting in concussions and CTE, are from the tangential component of impacts, which creates a rotational acceleration. Tangential speed and rotational velocity have been shown to have a stronger correlation with relative brain motion than any other kinematic parameter. Relative brain motion is directly proportional to the rotational acceleration. Rotational acceleration is directly proportional to the magnitude of a tangential impact multiplied by the distance from the rotational center of the head. The greater the tangential speed prior to impact, the greater the tangential impact and the greater the rotational acceleration. As the rotational acceleration increases, the probability of injury and incidence of a concussive impact also increases dramatically. Also, higher rotational accelerations create worse concussions. Decreasing the rotational acceleration decreases the concussion incidence. The functionality of an impact mitigation device, system, or method can be significantly improved by aligning the center of rotation of the impact mitigation device, system, or method with the center of rotation of the wearer's head. This proximate alignment centering feature functionally reduces rotational acceleration. It is not done as a design choice, nor is it done for aesthetic reasons. In fact, this functional alignment solution may even look aesthetically unbalanced, but science shows that this solution works. By mitigating the rotational acceleration, an impact mitigation device such as a helmet, will decrease concussions and/or other pathologic brain injuries. Thus, the least concussive effect can be achieved by proximate alignment of the rotational center of a spherical helmet with the center of rotation of a human's head, located in the center of the foramen magnum, or obex) also defined as the pivot point, around which the brain rotates upon receiving a head impact.

Because the position of the foramen magnum 92 is more posteriorly located in the skull base, it is imperative to functionally align the center of the spherical head worn protection system proximate over the center of rotation or the pivot point of the brain, specifically in the region of the upper spinal cord and brainstem junction (e.g., obex), at the foramen magnum 92. The least concussive effect can be achieved by this proximate alignment of the rotational center of a circular helmet with the center of rotation of a human's head. The magnitude of a tangential impact is minimized by using a spherical shaped helmet (which has a circular shell when looked at in a horizontal mid-plane section) and aligning the center of the circular shell with the center of rotation of the head.

Detailed Description of Helmet-Based Impact Mitigation Devices

Figure 2A:
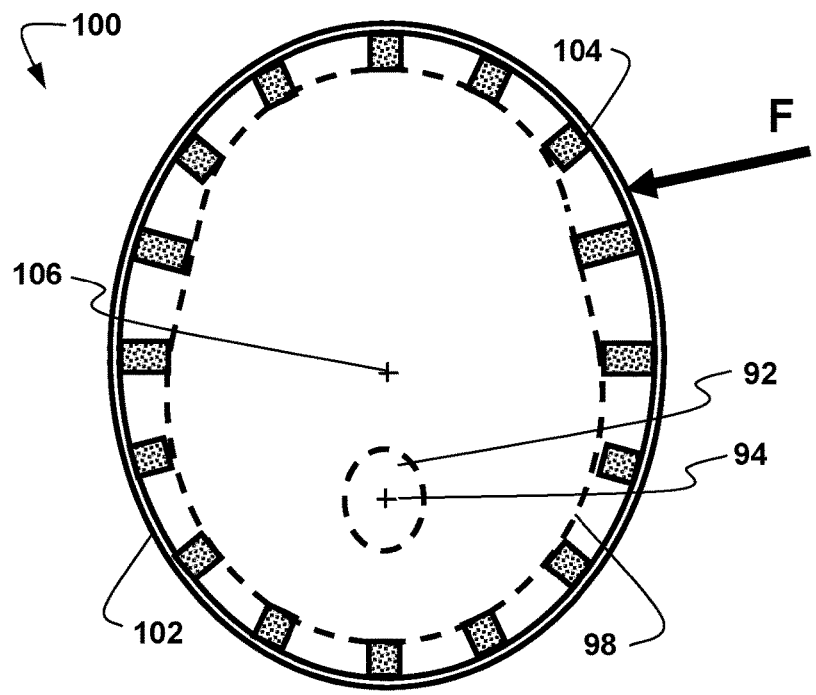
FIG. 2A is a horizontal section of a prior art helmet on a person's head.

Referring to the impact mitigation device drawings, FIG. 2A shows a horizontal section of a prior art helmet 100 on a person's head 98. The foramen magnum is shown at 92. The rotational center of the head is shown at 94. The prior art helmet 100 comprises a hard shell 102 and a set of pads 104 that conform to fit the person's head 98. Because the foramen magnum 92, center of head rotation 94, and spinal cord are located to the back of the person's head 98 and the pads 104 provide an approximately constant spacing between the person's head 98 and the hard shell 102, the center of the prior art helmet shell 106 is quite a distance from the rotational center of the head 94. A typical impact, shown at F, when applied to a prior art helmet generates a high rotational moment as will be further described below.

Figure 2B:
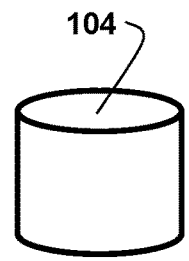
FIG. 2B is an isometric view of a prior art helmet pad.
Figure 2C:
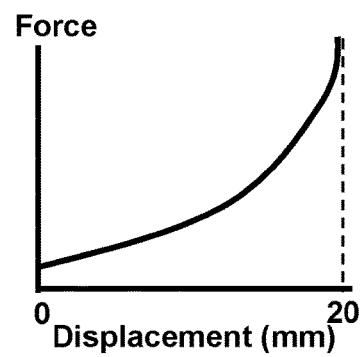
FIG. 2C is a force-displacement curve for a prior art helmet pad.

FIG. 2B shows an isometric view of the pad 104. FIG. 2C depicts the force-displacement relationship of the pad 104 in actual use. A typical prior art helmet pad 104 has a displacement of less than 20 mm in actual use before the pad is completely compressed. The force-displacement curve has a positive slope throughout its entire range. There is an initial force required before any displacement occurs because the pad is pre-loaded against the person's head (98 in FIG. 2A). This preload is shown by the y-axis intercept at 0 mm of displacement in FIG. 2C. The force rises steeply as displacement increases and the rate of increase per unit of displacement increases (i.e., the slope of the curve increases) until the displacement approaches the maximum displacement of the pad, at which point, the slope becomes asymptotically vertical because the pad 104 is fully compressed. This asymptotic line is shown at a value of 20 mm in FIG. 2C. The shape and characteristics of the force-displacement curve shown in FIG. 2C is typical of that for prior art helmets.

Figure 2D:
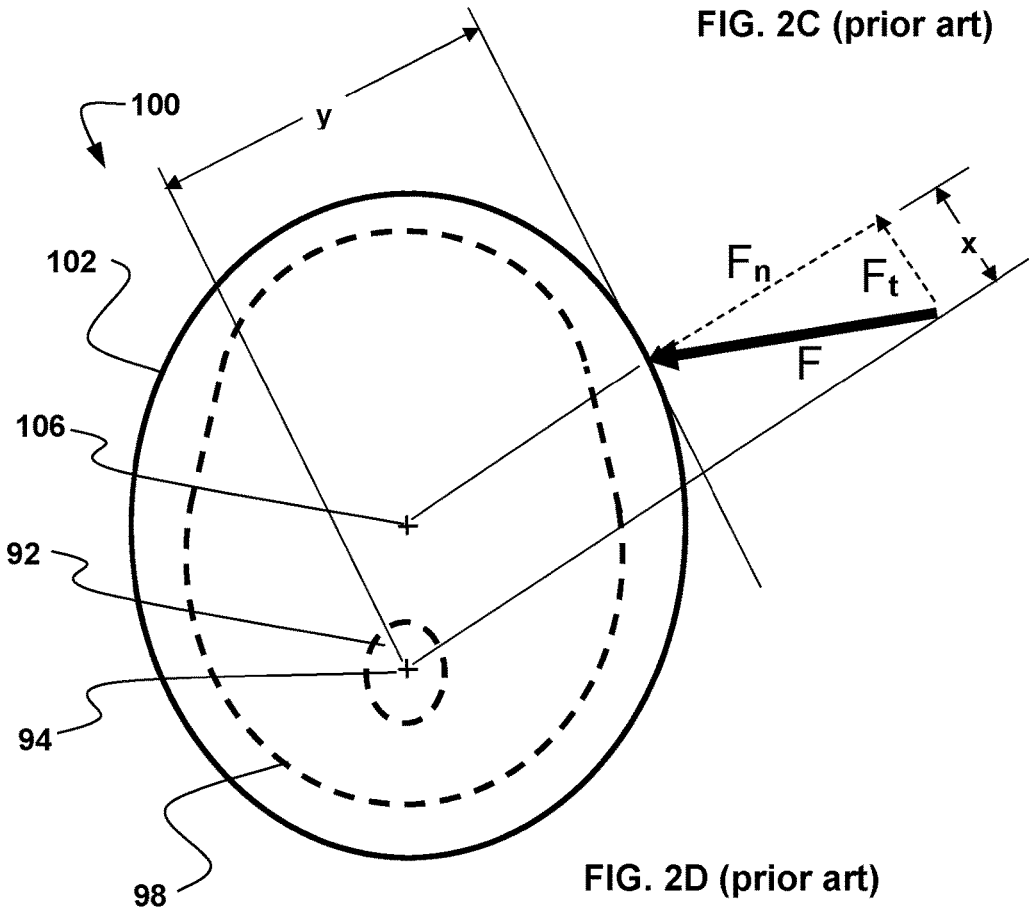
FIG. 2D shows the theory of operation of the prior art a helmet when subjected to an impact force at an arbitrary point.
Figure 3:
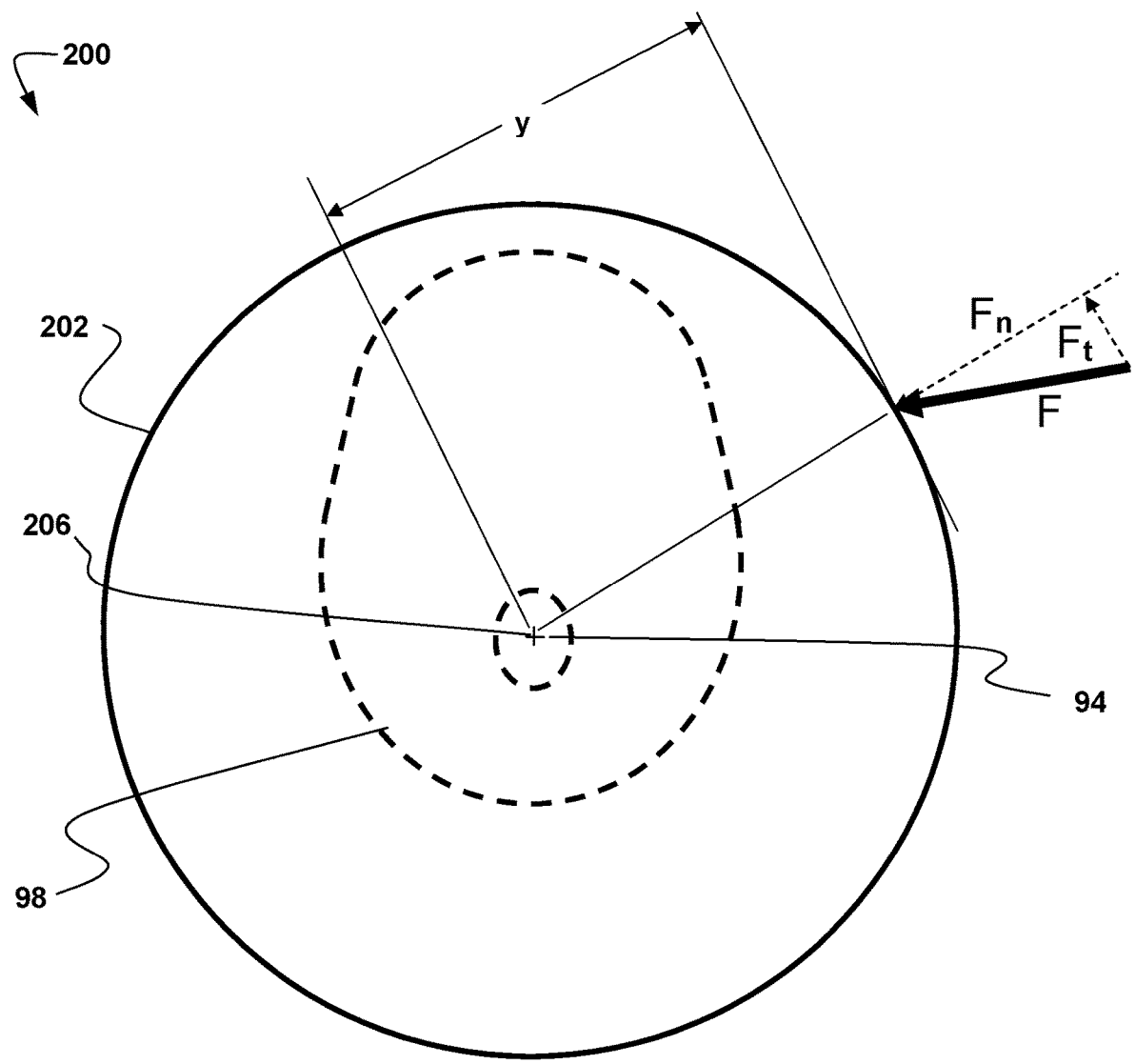
FIG. 3 shows the theory of operation of the top view of a spherical helmet that has been aligned with the center of rotation of the head.

FIG. 2D provides a 2-dimensional view of the theory of operation of a helmet by showing the same prior art helmet, 100 as in FIG. 2A, on a player's head 98. The foramen magnum 92, rotational center of the head 94, hard shell 102, and center of prior art helmet shell 106 are also shown. The force F is shown impacting the hard shell 102 at an arbitrary point. In actual use, impacts F can occur in any location and any direction on the exterior of a helmet. The impact F can be decomposed into: a force Ft that is tangential to the curvature of the exterior of the helmet at the point of impact and a force Fn that is normal to the exterior of the helmet at the point of impact. The tangential component of force Ft generates a rotational moment on the helmet 100 and hence on the brain stem and spinal cord transition located in the foramen magnum 92. The magnitude of this rotational moment depends on: (a) the coefficient of friction between the helmet exterior (in this case the hard shell 102) and the body that produced force F; (b) the perpendicular distance between the point of impact and the rotational center of the head 94, a distance shown at y; and (c) whether the collision is elastic, inelastic, or partially elastic. The tangential component of force Ft can also generate an axial force on the hard shell 102 and hence on the region of the foramen magnum 92. The magnitude of this axial force depends on (a) the coefficient of friction between the helmet exterior (in this case the hard shell 102) and the body that produced impact F and (b) whether the collision was elastic, inelastic, or partially elastic. Based on the preceding and as shown in FIG. 2D, one can minimize the effect of the tangential component of force Ft on the foramen magnum 92 region by minimizing the coefficient of friction between the helmet exterior and the body that produced force F and by making the center of curvature of the helmet exterior at the point of impact align as closely as possible with the rotational center of the head 94. More specifically the tangential component of force Ft will produce no force on the foramen magnum, 92, region if (a) there is a zero coefficient of friction between the helmet exterior and the body that produced impact F or (b) if the center of curvature of the helmet exterior at the point of impact is in the same location as the rotational center of the head 94, and the helmet exterior is coupled to the rest of the helmet in a way that allows the helmet exterior to rotate freely around the other elements of the helmet. In order for the center of curvature of the helmet exterior to be in the same location as the head rotational center for all tangential forces at all locations on the helmet, the helmet exterior must be spherical and the spherical helmet center must be at the same location as the center of the rotation of the person's head 94. This idealized configuration is shown in FIG. 3. Referring to FIG. 3, the rotational center of the head 94, has been aligned with the inertial center of an improved outer shell 202 having an inertial center 206 that is co-located with the rotational center of the head 94.

Further referring to FIG. 2D, the normal force Fn creates an axial force on the foramen magnum region 92. The normal force Fn can also create a bending moment (i.e., rotational force) at the rotational center of the head 94, if the center of the radius of curvature of the helmet exterior at the point of impact is not aligned with the rotational center of the head 94. For the geometry shown, a line drawn perpendicular to the tangent line the point of impact will intersect the center of prior art helmet shell 106. Therefore, for the geometry and impact shown, the size of bending moment created by Fn equals the offset between the center of the prior art helmet shell 106 (illustrated as x in FIG. 2D) multiplied by the magnitude of the normal force Fn. Note that if there is friction between the impact source and the hard shell 102 and the shell 102 is not free to rotate about the person's head 98, then the tangential force Ft will produce an additional bending moment equal to Ft multiplied by the perpendicular distance between a line tangent to the point of impact on the hard shell 102 and a parallel line that intersects the rotational center of the head 94. This perpendicular distance is shown at y in FIG. 2D. Referring to FIG. 3, the normal force Fn produces no bending moment if the radius of curvature of the helmet exterior at the point of impact (i.e., the center of the helmet shell if the shell is spherical) is aligned with the rotational center of the head 94. By comparing FIG. 2D with FIG. 3, one can see that there is no "x" dimension in FIG. 3.

Figure 4A:
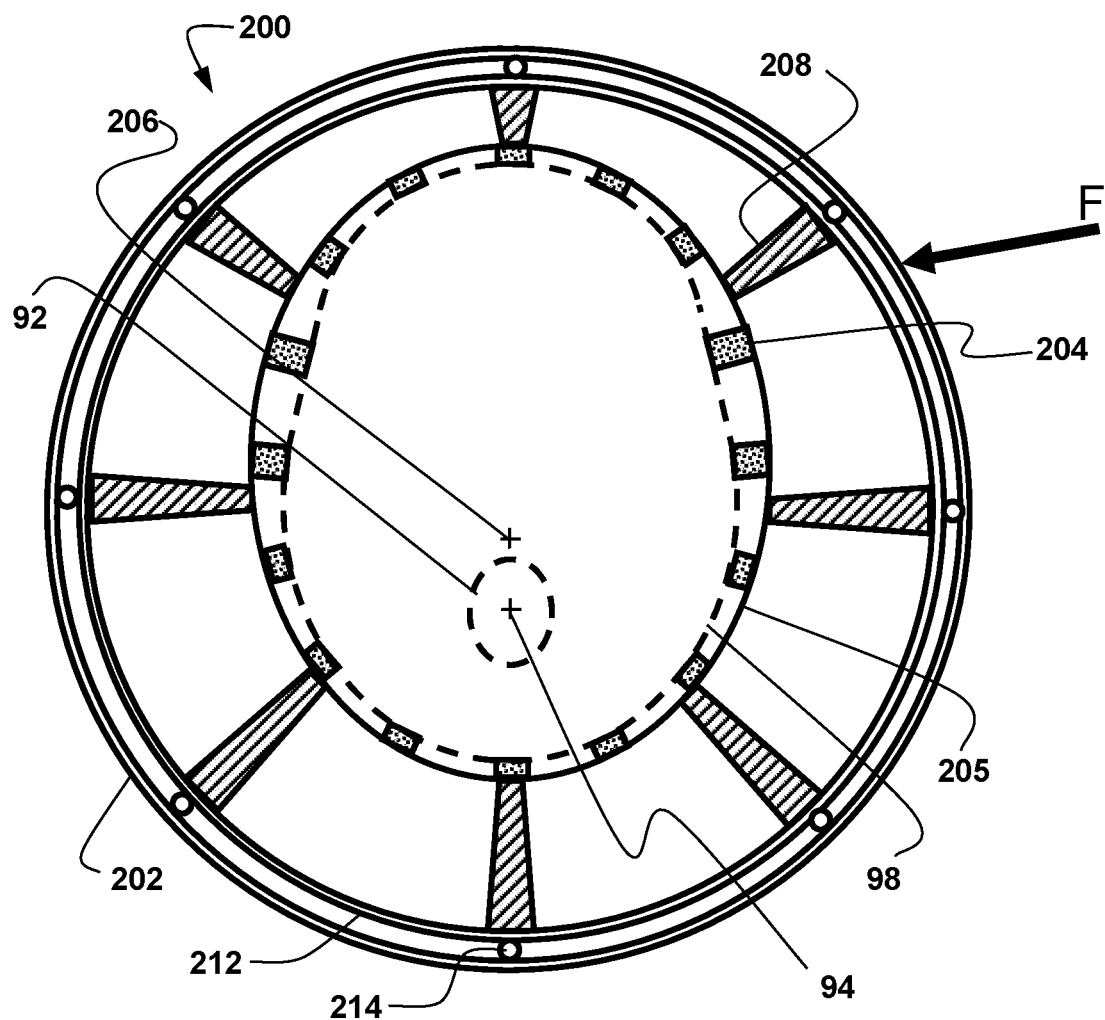
FIG. 4A is a horizontal section of the spherical helmet of FIG. 3.

FIG. 4A shows a horizontal section view of a rotationally centered impact reduction helmet 200 on a person's head. Like in FIG. 2A, the person's head is shown at 98, the foramen magnum is shown at 92, and the rotational center of the head is shown at 94. The embodiment of the impact reduction helmet 200 in FIG. 4A has several improvements over the prior art helmet 100 of FIG. 2A. A first improvement, shown in FIG. 4A, is that the head-conforming pads 204 are thinner. The head-conforming pads 204 are customized and configured to fit inside of a pad frame (or inner frame) 205 and press against the person's head, 98. In the improved helmet 200, the pad frame 205 is separate from the hard shell, shown at 202. The pad frame 205 is sized and shaped to conform as closely as possibly to the person's head 98, and custom fitted to each user. The pad frame 205 can be sized and shaped independently of the size and shape of the hard shell 202. By having a pad frame 205 that conforms as closely as possible to a person's head 98, the head-conforming pads 204 can be thinner than the pads 104 in the prior art design (FIG. 2A). In the prior art helmet (shown in FIG. 2A) the prior art pads 104 were configured to perform two functions: (a) to provide a comfortable fit on the person's head 98 and (b) to provide shock absorption. In the improved helmet, 200 FIG. 4A, shock absorption elements shown at 208 have been added to the system and these shock absorption elements 208 can be independent of the head-conforming pads 204. In the prior art shown in FIG. 2A, the pads 104 needed to be relatively thick to provide sufficient compliance to fit both big heads and small heads into the same shell 202. The improved helmet 200 of FIG. 4A allows a closer fitting of a pad frame 205 to a person's head 98. One of the ways to accomplish this closer fitting is to make the pad frame 205 from material that is initially flexible to fit the person's head 98 and subsequently hardened once the fit has been determined. Another technique for producing a custom pad frame 205 is to make a 3-dimensional scan of the person's head 98 and then to manufacture the custom pad frame 205 using a 3-dimensional printer. The methods for making this custom pad frame 205 can be any method or technique capable of being understood by anyone skilled in the art. The pad frame 205 can be rigid with the properties of being lightweight and strong. The pad frame (or inner frame) 205 could be made of materials such as carbon fiber, carbon fiber composites, graphene, boron nitride, lonsdaleite, linear acetylencic carbon, and/or other allotropes of carbon or carborundum.

Further referring to FIG. 4A, the shell 202 of the rotationally centered impact reduction helmet 200 is spherical. The use of a spherical shell 202 makes it is possible to minimize or completely eliminate the relationship between a tangential components of impact force (Ft shown in FIG. 2D) and any resulting rotational forces at the rotational center of the head 94. Rotational forces at the rotational center of the head 94, can be minimized or eliminated by either (a) minimizing friction between the source of impact and the spherical shell 202 or (b) allowing the spherical shell, 202, to rotate relative to an inner frame member, shown at 212.

The coefficient of friction between the source of impact and the spherical shell, 202, can be minimized by making the spherical shell out of a material that is "slippery" when relative to the materials used for the source of impact. Materials such as PTFE (polytetrafluoroethylene), PEEK (polyether ether ketone), polyimide, polyphenylene sulfide, nylon, acetal, and polyester are examples of materials that have a low coefficient of friction in most environments.

The spherical shell, 202, can be allowed to rotate relative to an inner frame member, 212, through the use of rotational couplers, shown at 214. This rotational friction reduction could also be accomplished through the choice of materials that provide a low coefficient sliding contact, such as the materials such as PTFE that were mentioned in the previous paragraph with regard to the spherical shell.

Note that the improvements shown in FIG. 4A can either be used with a spherical shell, which can allow rotation about two perpendicular axes or with a shell that has a circular geometry in one axis, but is non-circular about an axis perpendicular to this axis. In the latter case, the helmet could rotate freely about an axis aligned with the rotation of the upper spinal cord, but would not rotate about an axis perpendicular to this spinal rotation axis.

Further referring to FIG. 4A, the rotational center of the shell 202, is shown at the point labeled 206. This rotational center 206, is brought much closer to the rotational center of the head 94, than in the prior art shown in FIG. 2A and FIG. 2D. This repositioning of the rotational center 206, backwards on the person's head 98, further reduces the rotational forces as explained previously when describing the theory of operation and FIG. 4A. In an ideal case, the rotational center 206, would be the same as the rotational center of the head 94. Note that the center of the radius of curvature of a circle is the same as the center of the circle, and the same applies to a sphere. Thus, the center of curvature for a shell having a circular geometry will be the same as the rotational center 206. It is also the case that the center of the moment of inertia of a circle, or anything having a circular geometry will be the rotational center of that circle or item having a circular or spherical geometry. To summarize, the magnitude of a tangential impact can be minimized using a spherical shaped helmet (which has a circular shell when looked at in a horizontal section) when aligning the center of the circular shell with the center of rotation of the head. As the horizontally viewed center of a circular shell becomes more closely aligned with the rotational center or pivot point of a human head (e.g., in the region of the upper spinal cord and brainstem junction, (in the region of the foramen magnum), the tangential impact on the human can be decreased.

Further referring to FIG. 4A the customized pad frame 205, and inner shell 212 (or inner frame member) are connected through shock absorption elements 208. In the embodiment shown in FIG. 4A, the shock absorption elements 208, are fixed at one end to the pad frame 205, and at the other end to a shell 212, that is coupled to the outer shell 202. The shock absorption elements 208, shown in FIG. 4A can be sized to provide greater spacing between the customized pad frame 205, and the inner frame member 212, at the sides and the rear of the rotationally centered impact reduction helmet 200, than at the front of the improved helmet 200, to (a) allow a spherical shell 202, to fit onto a head that is oval and (b) allow the helmet rotational center 206, to be located proximate to the rotational center of the head 94—ideally the two centers of rotation would be at the same point.

Figure 4B:
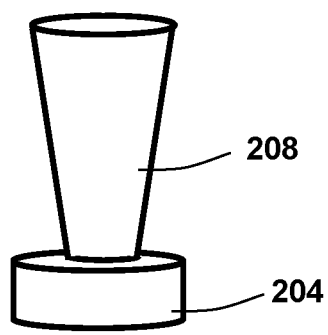
FIG. 4B is an isometric view of a head conforming pad and a shock absorption element in series.

Referring to FIG. 4B the head-conforming pads 204, and the shock absorption elements 208, operate in series in response to an impact. In the embodiment show in FIG. 4A, the shock absorption elements 208, are sized to provide a significantly greater displacement of the shell 202, relative to the person's head 98 than in the prior art design shown in FIG. 2A. The total displacement for even the shortest impact absorption elements 208, located near the front of the improved helmet 200, in FIG. 4A can be greater than the displacement of the largest pad 104, in the prior art design FIG. 2A. The higher displacement is needed to provide the distance required to decelerate from the typical speeds of impact in football while minimizing the risk of exceeding the accelerations that cause concussions.

The head conforming pads 204, and/or the customized shock absorption elements 208, can further comprise sensors and/or transducers to detect, measure and transmit biomedical and/or physical information related to the protective structure, in the form of visual, haptic or auditory signals to the user or to another device remotely, which can be viewed by others. These sensors/transducers could be self-adjusting, could interact with other sensors and can respond by changing form or characteristics when sensing elements/transducers on the outer rigid shell detect an impending violent blow which may require greater resistance to deformation.

In another embodiment, the head conforming pads 204, can comprise sensing elements and/or transducers to detect, measure and transmit biometric or abnormal physiologic and/or biochemical information related to health of the user, in the form of a visual, haptic or auditory signal to the user, to the protective structure worn, or to another device remotely, which can be viewed by others.

The head contains 28 bones and 17 named fusions where the bones are joined. The cranium or cranial vault is the portion of the skull which encloses and protects the brain (e.g., the braincase) and is comprised of 8 bones. Each of these different bones have different areas of thickness. For example, the temporal bone, on the side of the cranium, is the thinnest bone of the skull. The occipital bone is the thickest skull bone, and the frontal bone is the second thickest bone of the skull. The bones of skull have a limited amount of elasticity. If the limits of elasticity are not exceeded, the bone will recoil to its normal shape and fracture will not occur. Fractures due to general deformation are usually fissured and they can occur in parts of the skull distant from the site of application of the force. Because some bones are thick, they are likely to be stiff and deform little when loaded. The majority of bones varied in thickness from 5 to 7 mm except temporal and parietal bones, which can vary from 3-4 mm. Also, the skull bones are not uniform plates and have great variations in thickness and shape at different points, depending on age, sex, culture and hereditary factors. The pericranium is a dense membranous outer periosteum of the calvarium. It covers the external surfaces of the frontal, parietal, and occipital bones deep to the subgaleal areolar tissue and extends as far laterally as the superior temporal line on each side. The pericranium also varies in thickness from individual to individual and from region to region. Generally, however, the pericranium is thicker frontally than at the vertex. The temporal bone has little pericranium and can offer little resistance to bending. It is a simple fact that a thin plate of bone will break first because of the poor resistance when compared to thick bone. The importance of these anatomic features such as the varying skull bone thickness and thinness can be correlated with skull fractures sites and intracranial damage. These anatomical features of the skull can be correlated with specific placement needs of the head conforming pads 204, as seen in FIGS. 4A, 4B, 5A and 7A, and/or the customized shock absorption elements 208, 306, 304, as seen in 4A, 4B, 5A. 6A, 6B, 6C, 6D, 6E and 6F, having different thickness, construction, shapes, resiliency, elasticity, rebound rates, different impact mitigation elements, different purposes and force displacement characteristics. Specifically, in embodiments of the invention, different types of head conforming pads and/or shock absorption elements can be selected and specifically placed, based on the anatomical features discussed, such as thickness or thinness of the cranial vault or the area near the most likely part of the brain for injury or for a specific purpose of measurement. As an example, shock absorption elements having different elastomeric properties, shape, size, rebound rate, or force displacement characteristics may be placed in the temporal area compared to the impact material selected and placed in the occipital region. The head conforming pads 204, are not just for comfort and adjustment of the helmet to prevent slippage and accommodate different sizes of heads. These pads as indicated, can have additional purpose of impact mitigation and for selected areas of the head, the properties of such pads can vary, depending on the area in which they are placed as mentioned above. They can also be used to assist other biochemical and/or physiologic measurement functions, with the use of attached or adherent sensors, which would be in contact with the skin in those anatomically chosen locations for the purpose the sensors were designed.

The head conforming pads 204, and/or the shock absorption elements 208, can be adjustable to maintain proper relationship of the outer shell 202, and the inner frame 212, both of which can be centered over the upper spinal cord in the region of the foramen magnum. The conforming pads/cushions, 204 and 208, can be inflatable. Sensors and/or transducers in any of these elements can be specific to that component for the measurement of a specific function and can be anatomically and strategically positioned for more precise measurement for which the specific sensors and/or transducers are designed.

Figure 4C:
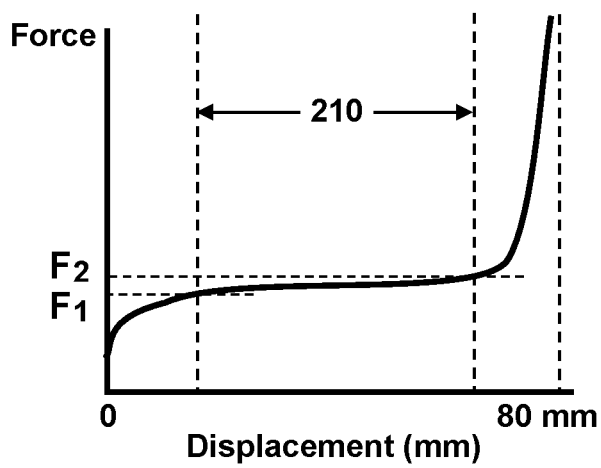
FIG. 4C is a force-displacement curve for a head confirming pad helmet pad and a shock absorption element in series.

FIG. 4C illustrates a force deflection characteristic for the head-conforming pads 204, and shock absorption elements 208, of the improved helmet 200, of FIG. 4A and FIG. 4B. To decelerate as much as possible without exceeding an unsafe (concussion-risky) G-force it is desirable to decelerate as linearly as possible. Since force equals mass times acceleration, this means that the resistance force of the shock absorption elements should be as linear as possible. As shown by the force displacement curve in FIG. 4C, and based on the calculations shown earlier, we would like to have a displacement of at least 60 millimeters in which the resistance force of the shock absorption elements 208, is as flat (i.e., constant) as possible. The table below illustrates the relationship between speed of impact, displacement in the linear region (shown at 210, in FIG. 4C and 354, in FIG. 7B), slope of the linear region (defined and calculated as [F2−F1]/F2), and maximum acceleration if this section of the force-displacement curve is responsible for dissipating the entire impact. The values in the table below for a slope of 1 were generated by assuming that jerk (the rate of change of acceleration as a function of time) is a constant. This generates the following simultaneous equations to be solved:

$v = (1/2) j\, t^2$ (if jerk is constant)

$x = (1/6) j\, t^3$ (if jerk is constant)

$a = j\, t$ (if jerk is constant)

where: x is displacement, v=velocity, a=acceleration, j=jerk, and t=time

| Impact speed | Slope | Displacement | Time | Maximum Acceleration |
|---|---|---|---|---|
| 10 meters/sec | 0 | 25 mm | 5 msec | 2000 m/sec$^2$ (200 g) |
| 5 meters/sec | 0 | 25 mm | 10 msec | 500 m/sec$^2$ (50 g) |
| 10 meters/sec | 0 | 50 mm | 10 msec | 500 m/sec$^2$ (50 g) |
| 5 meters/sec | 0 | 50 mm | 20 msec | 125 m/sec$^2$ (12.5 g) |
| 10 meters/sec | 1 | 25 mm | 7.5 msec | 2667/sec$^2$ (267 g) |
| 5 meters/sec | 1 | 25 mm | 15 msec | 667/sec$^2$ (67 g) |
| 10 meters/sec | 1 | 50 mm | 15 msec | 667/sec$^2$ (67 g) |
| 5 meters/sec | 1 | 50 mm | 30 msec | 167/sec$^2$ (16.7 g) |

Figure 5A:
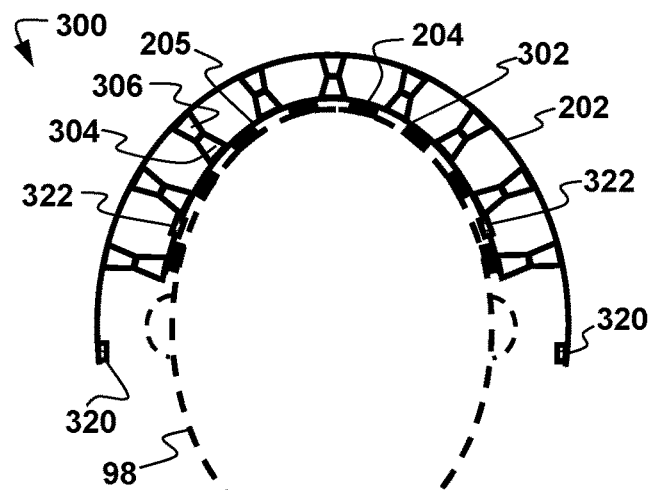
FIG. 5A shows a vertical section of an alternate embodiment helmet.

FIG. 5A shows a cross-section front view (i.e., a coronal view) of an alternate embodiment improved helmet 300, on a person's head 98. The alternate embodiment 300, is similar to the improved helmet 200, in FIG. 4A in that the alternate embodiment 300 comprises a plurality of head conforming pads 204 located closest to the person's head 98 and mounted in a pad frame 205. The alternate embodiment 300, is different from the improved helmet 200, of FIG. 4A in that the alternate embodiment 300, does not have an inner frame (212 in FIG. 4A) that can be rotationally coupled to the shell 202, in FIG. 4A. Instead, the alternate embodiment 300, has a plurality of customized compound shock absorption elements, each of which comprises a first elastically resilient impression, shown at 304, and a second elastically resilient impression, shown at 306. In the alternate embodiment 300, the second elastically resilient impression 306, is connected directly to the spherical shell 202 and the first elastically resilient impression 304, is connected to the pad frame 205.

Referring generally to the embodiments shown in FIG. 4A and FIG. 5A, one skilled in the art can imagine further combinations of the elements and configurations shown in these two figures. For example, another possible embodiment of the improved helmet could comprise compound shock absorption elements of the type shown at 304, and 306, in FIG. 5A with these elements attached on their outside to an inner shell like that shown at 212, in FIG. 4A. A further possible embodiment could be to have compound or non-compound shock absorption elements like those shown at 208, in FIG. 4A that attach directly to the shell of the type shown at 202, in FIG. 5A.

Referring further to FIG. 5A, the elastically resilient impressions 304, and 306, can be made of a variety of materials, including carbon fiber or nanometer-scale carbon nanotubes. They can also have a variety of shapes, resiliency, elasticity, rebound rates, different impact mitigation elements and force displacement characteristics. These elastically resilient impressions can be fluid (gas or liquid) filled sealed units. They can be plastic or rubber dimples. They can be metal or non-metal springs, such as leaf springs or coil springs. They can be dimples made from a material such as polyethylene or some other plastic, metal, rubber material, or any other material having at least some elasticity. They can be made of any other materials or implemented in any other configurations capable of being understood by anyone skilled in the art.

Further referring to FIG. 5A, the configuration of the helmet 300 can include sensors, shown at 320 and 322. The sensors shown at 320, are attached to the shell 202. The sensors shown at 322 are proximate to the user's head 98. These sensors 320, and 322, could also be attached to the wearer's body. The sensors 320 and 322, could be shielded from the wearer's body for safety reasons. The sensors 320, could be used to detect a variety of parameters, examples of which can include:

- detecting a rotational or angular acceleration, which might be useful in determining characteristics such as, the timing of an impact, the magnitude of an impact, the direction of an impact, or the effectiveness of the impact reduction system in reducing the severity of the impact;
- detecting an orientation, which might be useful in determining a characteristic such as the position of a person's body part at the time of an impact;
- detecting a velocity, which might useful in determining a characteristic such as the velocity at which an impact occurred;
- detecting a parameter of another object in the vicinity, an example might be detecting the location and velocity of other impact pads (such as helmets) being worn by other persons in the vicinity, which might be useful in identifying an impending impact;
- detecting a signal from another object in the vicinity, an example might be detecting an alarm signal coming from a device on another soldier in the vicinity;
- detecting other sensors such as those on other helmets in the vicinity or detecting some parameter or sensor associated with the person wearing the helmet, a feature that can allow the helmet to identify and/or respond to of the person wearing the helmet; and/or
- the sensors 322, could be used to detect a variety of parameters, examples of which can include detecting a biometric, physiologic and/or biochemical parameter associated with the wearer of the helmet. These sensors would be specifically anatomically located depending on the purpose for which the measurement is designed. Examples of biometric, physiologic and/or biochemical parameters can include blood pressure, pulse, body temperature, oxygen saturation, electro-cardio activity, brain activity, neural activity, chemical levels in the sweat, such as sugars, electrolytes and/or cortisol.

The sensors shown in FIG. 5A can be connected to a processor that is part of the impact reduction system. This processor can include a memory element to store sensor data. This stored sensor data can be used for data logging, which can facilitate evidence-driven management of the sensing and data collection process, whereby data derived from the sensors could be used to repair, modify, or alter the responsiveness of a sensor or to alter the responsiveness of a sensor and/or alter the data being recorded from a sensor or to alter the frequency at which data is being recorded from a sensor. The sensor data can also be transmitted and this transmission can be in the form of a wireless protocol such as WiFi, Bluetooth, Zigbee (and related IEEE 802.15.4 and XBee), a cellphone signal, or any other wireless protocol capable of being understood by someone skilled in the art and using sensing elements/transducer materials which promote wireless connectivity. An example can be the use of materials for flexible electronics with faster transistors and semiconductors such as Graphene and Cyrene (dihydrolevoglucosenone), which can provide higher concentrations and conductivity of graphene ink for wireless connectivity to the IoT as well as provide RF energy harvesting for low power electronics.

The sensor data can also be used to produce an alarm signal capable of being understood by a human, examples of which might include an audio alarm, a visual flashing red light, or a vibration or other tactile signal. The sensors 320 and 322 can be powered by a battery, by a generator, or by an external power source that sends its power over a wired or wireless method. Other power sources could include: a rechargeable lithium-ion battery, solar power, mechanical power, liquid-free and cobalt free battery, battery using waste graphite, 3-D battery, salt water battery, flexible nickel-metal hydride battery, ZIF-derived bifunctional air electrodes, knittable zinc-air batteries, combinations of graphene, hybrids of Magnesium Oxide, flexible nanowire networks harvesting energy from biological systems (moisture enabled electricity generation, flexible supercapacitor comprised of layers of flexible, 3D porous foam formed from graphene and silver electrodes, lead zirconate titanate coated with flexible metal foil, ultracapacitors or various other power supply materials or non-battery power sources and types known in the art. The sensors can be self-adjusting sensors that learn from data being received to better tune themselves to signals and discriminate these useful signals from other signals and background noise.

Figure 5B:
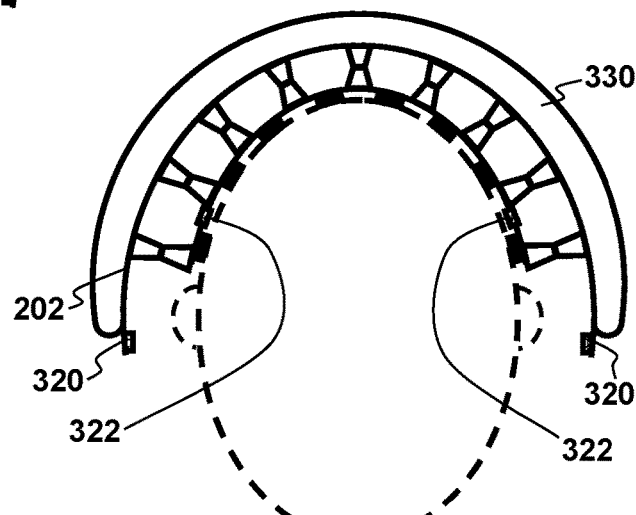
FIG. 5B shows the helmet of FIG. 5A further comprising an external airbag.

The sensors 320 and 322, shown in FIG. 5A can also be connected to an impact mitigation device such as an air bag (330 in FIG. 5B). This air bag 330 could be located anywhere outside of the shell 202. Thus, an impact-detecting or impact-anticipating sensor could issue a signal to the airbag system that causes the airbag to deploy, cushioning the impact and thereby reducing the magnitude of the impact and bodily damage to the person wearing the impact reduction system.

Figure 5C:
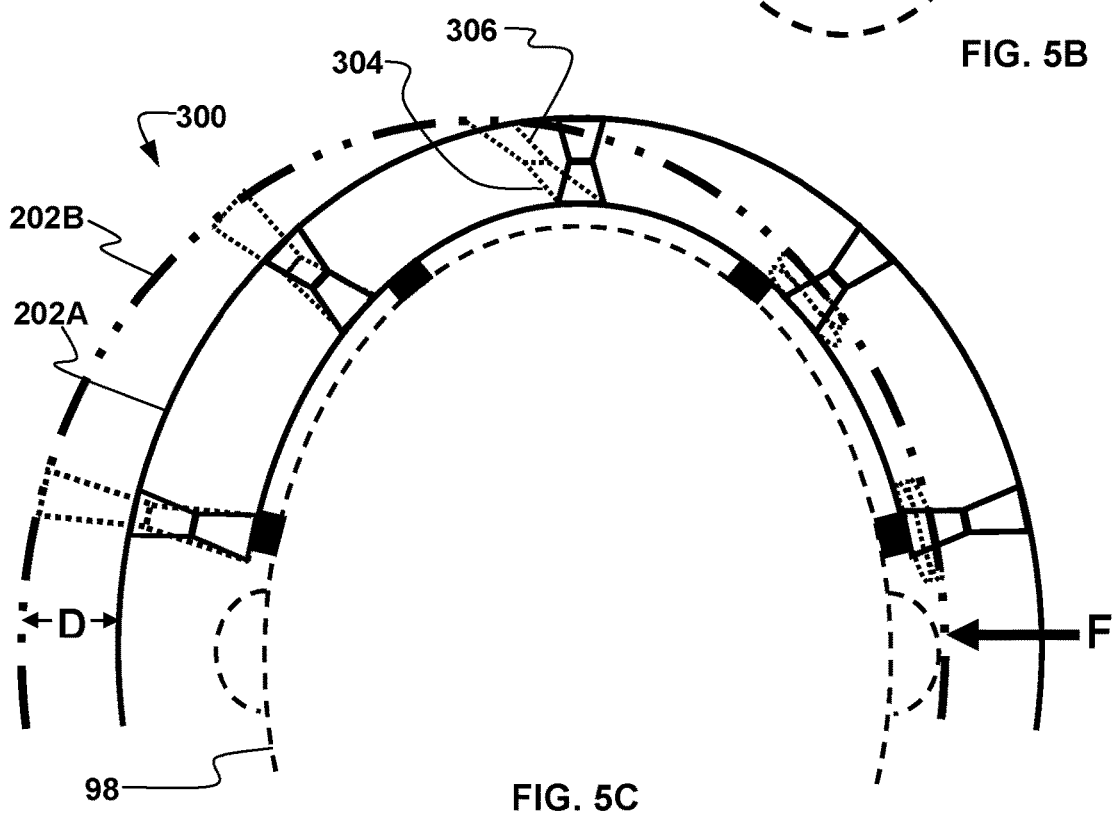
FIG. 5C shows the displacement of the helmet of FIG. 5A when subjected to a lateral force.

FIG. 5C shows the result of a side impact F on the helmet embodiment 300, that was also shown in FIG. 5A. More specifically, this shows the movement of the helmet shell from an initial position 202A to a final position 202B, on the opposite side, as a result of the applied force F. This applied force F causes a lateral displacement shown as dimension D in FIG. 5C. Examples of the displacement of the impact pads that were shown at 304 and 306, in FIG. 5A can be seen by dotted lines in FIG. 5C.

Figure 6A:
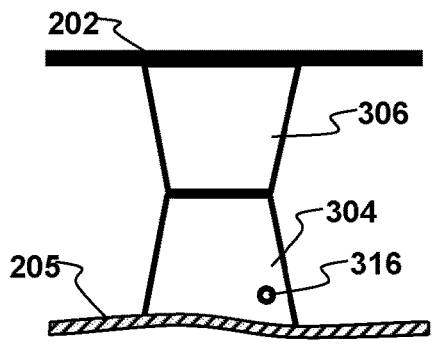
FIGS. 6A, 6B, and 6C are detailed views of two layers of elastically-resilient impressions in a serial configuration for use in a helmet.
Figure 6D:
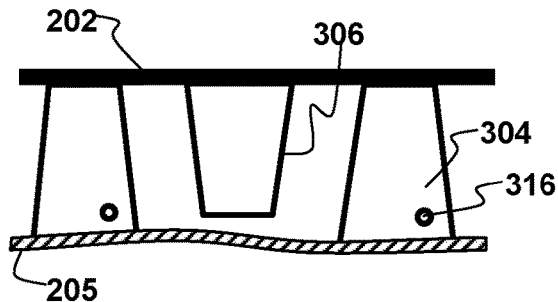
FIGS. 6D, 6E, and 6F are detailed views of elastically-resilient impressions in a parallel configuration for use in a helmet.
Figure 6B:
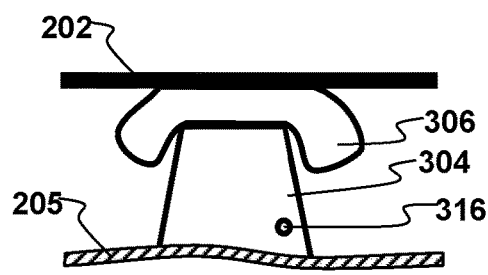
Figure 6E:
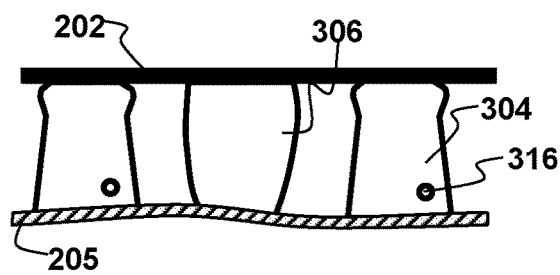
Figure 6C:
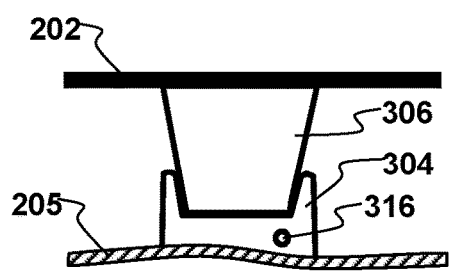

Referring to FIGS. 6A, 6B, and 6C, detailed views of elements of the alternate embodiment (300 in FIG. 5A) are shown. Among the elements from FIG. 5A that are shown in FIG. 6A, FIG. 6B, and FIG. 6C are the pad frame 205, a first elastically-resilient impression 304, a second elastically-resilient impression 306, and a shell 202. These elements (pad frame 205, first elastically-resilient impression 304, second elastically-resilient impression 306, and a shell 202) can be described as a four-layer impact reduction system. In the embodiments shown in FIGS. 6A, 6B, and 6C, the two layers with dimples 304 and 306, are in a series relationship (i.e., an aligned contact) in that the same force that passes through the first elastic impression, 304, is transmitted to the second elastic impression 306 and the total compression is the sum of the compression of the first elastic impression layer 304 and the compression of the second elastic impression layer 306. In the embodiment shown in FIGS. 6A, 6B, and 6C the second elastic impression 306, comprises a sealed air chamber and the first elastic impression 304 comprises an orifice 316, that allows air (or any other gas or liquid) to bleed out of the impression, providing a damping or "shock absorber" feature whose resistance to compression (or tension) is velocity sensitive. Note that the sealed air chamber shown in the second impression 306, could be implemented in a variety of ways examples of which include using a permanently sealed chamber, using a bladder that can be filled or emptied as desired through a closeable valve, and/or using a closed cell foam. Note also that the elements with damping in them can have a single orifice 316, or multiple orifices, and at an extreme the damping could comprise open-cell foam. FIG. 6A shows the system in a relaxed state in which there is no force compressing the shell 202, towards the pad frame 205. FIG. 6B shows an exaggerated example what happens as a result of a high-speed acceleration of the shell 202, towards the pad frame 205, as the bulk of the deflection is taken by the sealed second elastically resilient impressions 306, because there is not enough time to bleed the air through the orifice 316, in the first elastically resilient impressions 304. FIG. 6C shows an exaggerated example of what happens as a result of a low speed acceleration of the shell 202, towards the pad frame 205, as the bulk of the deflection is taken by the unsealed first elastically resilient impressions 304, because there is time to bleed the air through the orifice 316, and the second elastically resilient impressions 306, are deformed less because the bulk of the deflection occurs as a result of air bleeding through the orifice 316, from the first elastically-resilient impressions 304.

Figure 6F:
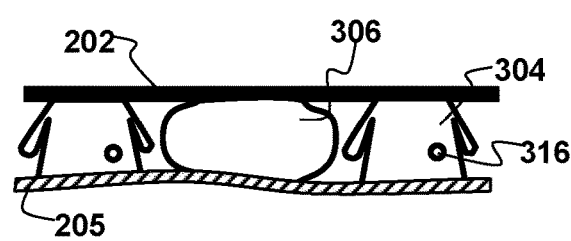

Referring to FIGS. 6D, 6E, and 6F, detailed views of elements of another embodiment of a helmet similar to the alternate embodiment 300, FIG. 5A are shown, including the pad frame 205, a first elastically-resilient impression 304, a second elastically-resilient impression 306, and a shell 202. In the embodiments shown in FIGS. 6D, 6E, and 6F, the first elastically-resilient impressions 304 and the second elastically-resilient impressions 306, are in a parallel relationship (i.e., an offset contact) in that an equivalent deflection occurs in both the first impressions 304. and the second impressions 306. and the total compressive force being transmitted is the sum of the force in the first impressions 304, and the force in the second impressions 306. In the embodiment shown in FIGS. 6D, 6E, and 6F the second impressions 306, comprise sealed air chambers and the first impressions 304, comprise orifices 316, that allow air to bleed out of these impressions, providing a damping feature. FIG. 6D shows the system in a relaxed state in which there is no force compressing the shell 202 towards the pad frame 205. FIG. 6E shows an exaggerated example what happens as a result of a high-speed acceleration shell 202 towards the pad frame 205, as the bulk of the compression is resisted by the first impressions 304, because there is not enough time to bleed the air through the orifices 316. FIG. 6F shows an exaggerated example of what happens as a result of a low speed acceleration of the shell 202, towards the pad frame 205, as the bulk of the compressive force is resisted by the sealed second impression 306, because there is time to bleed the air through the orifices 316, of the first impressions 304.

Further referring to FIG. 5A and FIG. 6A to FIG. 6F, the first elastically resilient impressions 304, and second elastically resilient impressions 306, can be designed to have different resistance to deflection in a direction perpendicular to the surfaces of the pad frame 205, and the shell 202, than their resistance to deflection parallel to the surfaces of the pad frame 205, and shell 202, whereby the rotational resistance of the helmet shown as 300, in FIG. 4 might be different than the resistance to impacts perpendicular to the shell of the helmet 300, in FIG. 5A. Note also that the force deflection characteristics can be different for different resilient impressions in the helmet 300. Thus, the helmet can comprise shock absorption elements that have force-displacement relationships that vary:

as a function of direction;
    as a function of speed;
    as a function of position;
    as a function of location; and/or
as a function of rotation versus translation.

Figure 7A:
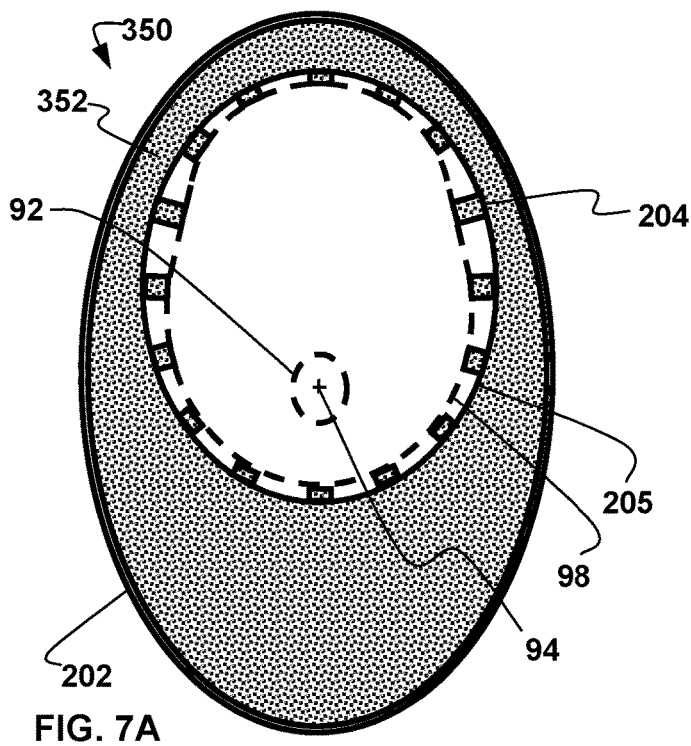
FIG. 7A shows a configuration of an embodiment of an improved helmet that incorporates a single-use impact reduction material.
Figure 7B:
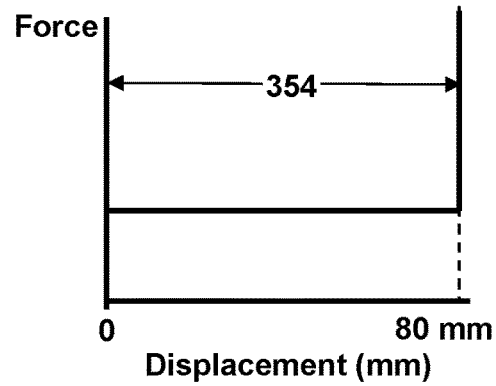
FIG. 7B is a force-displacement curve for a single-use constant force impact reduction material.

Referring to FIG. 7A yet another embodiment of an impact reduction helmet is shown at 350. More specifically, this is a single-use impact reduction helmet 350, that incorporates a single-use impact material 352. One example of a single-use impact material 352, is metal foam. The advantage of this type of a material is that after an accident the size of the impact can be directly seen from the amount of material that has been permanently deformed. FIG. 7B shows the force-displacement relationship for the single-use impact material 354. As one can see, the force is totally constant for the entire range of displacement until all of the material has been crushed. Note that this single use helmet 350, can also incorporate a change in the gap between the front of the helmet and the rear of the helmet. In this case, the oval shape of the helmet is retained to reduce wind resistance, but the center of rotation and the center of curvature have been moved back to the rotational center 94, which is the center of the upper spinal cord in the region of the foramen magnum 92.

Figure 7C:
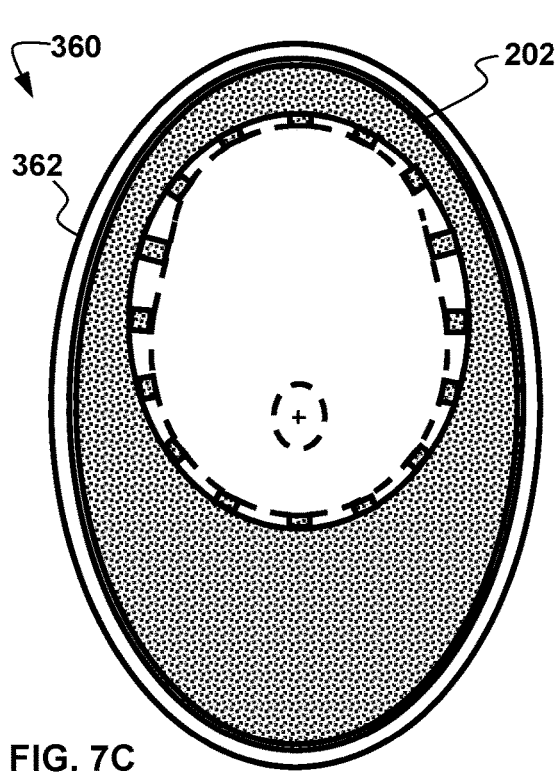
FIG. 7C is an oval helmet with a rotationally compliant cover.
Figure 7D:
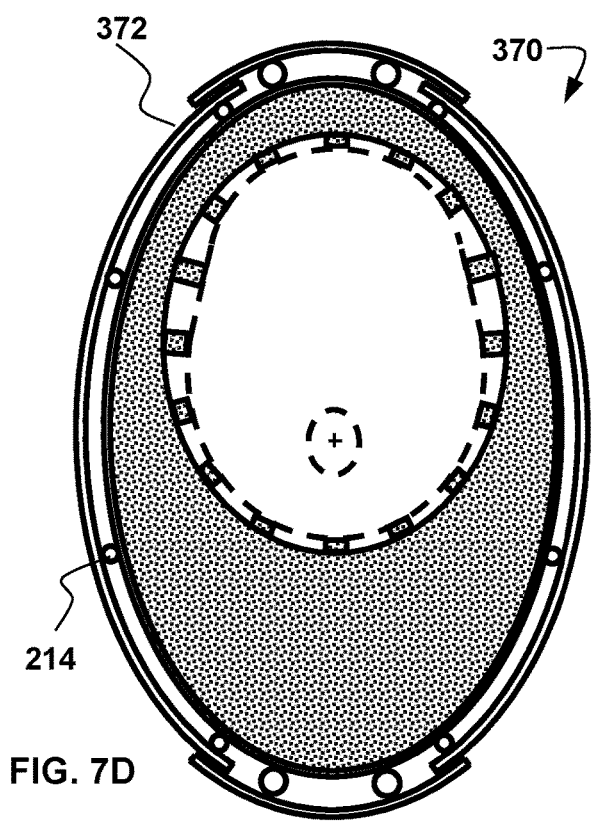
FIG. 7D is an oval helmet with a multi-element rotationally compliant cover.

Referring to FIG. 7C an oval helmet similar to that of FIG. 7A has been illustrated. The oval helmet, shown at 360, incorporates a rotationally compliant cover, shown at 362. The cover 362, that is shown could be made out of a soft material, such as a knit fabric that has a very low coefficient of friction relative to the shell 202, that is below it, making it easy to prevent tangential forces on the shell 202, from creating a load on the wearer of the helmet. Referring to FIG. 7D, it is also possible to place multiple rigid segments of elements on the outside of the helmet and allow those to be rotationally compliant as shown by the helmet 370, having rigid shell elements 372, that attach to the rest of the helmet through rotational couplers 214.

Further improvements that can be made to any of the embodiments described above can include:

1. The addition of sensors to warn of an impending collision, similar to the sensors being used on driverless vehicles. These collision-detection sensors can be used to deploy additional padding such as air bags outside of the outer shell.
2. The use of inertial sensors in the helmet. These sensors can measure impact. They can additionally record these impacts and/or transmit impact information using a wireless protocol. Transmission can be in the ultra-high frequency band, which is from 300 Mhz to 3 Ghz, the super high frequency band, which is from 3 Ghz to 30 Ghz, or the extremely high frequency band, which is from 30 Ghz to 300 Ghz. These sensed impacts can also generate alarms that can be auditory, visual, tactic, or communicated to the helmet wearer or another person at another location. The sensors may be self-adjusting based on a measurement of background noise or based on calibration to a specific user and use profile. The sensors may change an alarm in response to past history. The sensors may provide feedback to the shock absorption elements in the helmet to help tune these shock absorption elements.

3. In one embodiment, the sensors could be responsive to remote assistance that allows a remote device or person to evaluate, correct, repair, or switch from sensor to sensor. Similarly, another person (remotely) can evaluate individual sensors and use data logging and evidence-driven information to make changes to the sensors.
4. In one embodiment, the sensors may provide active streaming of the person's biometric/physiologic or biochemical information. The biometric information can include parameters such as pulse, oxygen saturation, blood pressure, change in neural activity such as an EEG, and body temperature. These biometric sensors could be located closest to the person's skin surface. Sensors further from the wearer's body can measure an impending impact, the type of impact (i.e., whether it is a projectile or a blunt object), and impact speed, and impact direction. Sensors in the helmet may also provide information about the wearer's identity. These sensors could be located on the outer shell or could be located closer to the person's body.
5. Making the shell (shown as 202, in FIG. 4A) can be made of multiple elements that have the ability to move relative to one another and have energy absorption between them. For example, a face mask (not shown) or face shield could be attached to other parts of the outer shell through an energy-absorbing coupling.
6. The shell (shown at 202 in FIG. 4A) could be specifically designed to be smooth and completely free of non-spherical obstructions, such a protrusions, ridges, or indentations. Non-spherical obstructions can make it more difficult for a helmet to "bounce" off of another helmet or other impacting device or material surface. The spherical shell could have multiple openings for ventilation, or to reduce weight. Prior art helmets typically have ridges or indentations on the shell that can be grabbed or catch on things or surfaces and increase the forces on the helmet, especially rotational forces.

It should be noted that the embodiments shown in this invention could be made of a material that aids in the effectiveness of the helmet. Such specialized materials can include: silicon carbide; boron carbide; amorphous boron; hafnium carbine; tantalum carbide; tungsten carbide; magnesium diboride; carbon nanotubes; glassy carbon; diamond-like carbon; single-crystal tungsten; boron nitride; titanium diboride; hafnium diboride; lanthanum hexaboride; cerium hexaboride; molybdenum carbide; tungsten disulfide; polyethylene; polyurethane; polyvinyl; nylon; an aramid material such as Kevlar; or any organic or inorganic material. In various embodiments, shear responsive materials may be incorporated into various components of the outer shell, pad frame, inner frame and/or liner components, including materials that stiffen and/or harden in response to impact forces such as PORON XRD urethane.

It should be noted that the embodiments shown in this invention could have sensors made of a variety of materials including nanotubes of pure carbon, graphene made of pure carbon, single electron transistors (SETs), organic molecular materials, magnetoelectronic materials (spintronics), organic or plastic electronics, or any other material capable of being understood by someone skilled in the art. Sensors can also be comprised soft mesh and flexible (of materials such as gold-coated silver nanowires mixed with a type of rubber, called polystrene-butadiene-styrene. Among electrochemical transducing elements, organic electrochemical transistors (OECTs) can be used for bioelectronics due to their exceptional ability to interface electronics with biology.

Ocular Performance-Based Head Impact Measurement Devices

Figure 8:
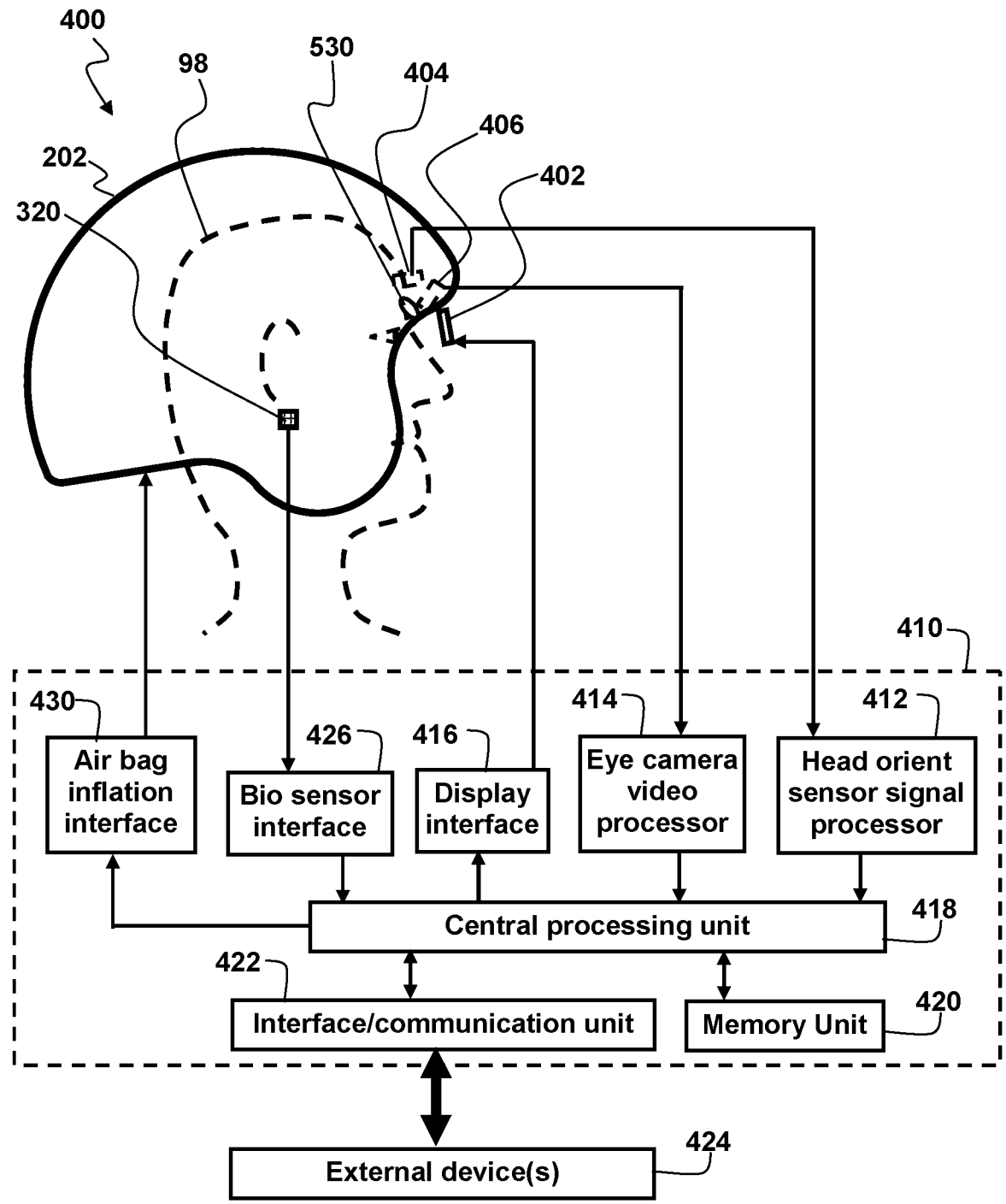
FIG. 8 shows a centered spherical helmet that comprises an ocular performance measuring system.

Referring now to the figures that describe ocular performance-based head impact measurement, FIG. 8 shows a helmet, similar to the ones illustrated and described with reference to FIG. 3 through FIG. 7D, that further comprises an ocular performance-based measuring system. Referring in more detail to FIG. 8, the rotationally centered impact reduction helmet comprising an ocular performance measuring system 400 is shown on the head 98, of a person. The centered ocular performance measuring helmet 400, can comprise a spherical shell 202, a see-through display 402, a head orientation sensor 404, an eye measuring sensor 406, and an illumination source 530. The centered ocular performance measuring helmet 400, is designed to fit snugly on the head of the person 98 so that all changes in head orientation result in equal changes in orientation of the centered ocular performance measuring helmet 400. The head orientation sensor 404, is rigidly attached to the centered ocular performance measuring helmet 400. In at least one embodiment, the head orientation sensor 404, senses (is responsive to) pitch, roll, and/or yaw. Pitch can be described as upward or downward movement of the face. Roll can be described as rotation of the face when viewed from the front. Yaw can be described as leftward and rightward movement of the face when viewed from the front. The head orientation sensor 404, can be constructed from one or more elements or it can be monolithic. The head orientation sensor 404, can use one or more accelerometers, gyroscopes, magnetometers, or any other relative or absolute position, velocity, or acceleration sensing device capable of being understood by anyone skilled in the art. In one embodiment, the orientation sensor comprises a micro-electro-mechanical system (MEMS) integrated circuit.

Further referring to FIG. 8, in one embodiment, the eye sensor 406, is more specifically an eye tracking digital video camera that is pointed at the eyes of the person. The eye sensor 406, can be responsive to any eye position, including vertical movement of the eyes (which represents pitch), rotation of the eyes (which represents roll), and horizontal movement of eyes (which represents yaw). It can also be responsive to eyelid position. There can be one eye sensor camera 406, that monitors only one eye, one eye sensor camera 406, with a wide angle, that can monitor both eyes, or two cameras, one to monitor each eye. There can also be multiple cameras, to monitor different areas of each eye (e.g., eye response sensors tracking pupil features and corneal reflection surfaces). The eye sensor video camera 406, can be positioned anywhere around the eye, and can utilize visible or invisible light. In one embodiment, the system shown at 400 further comprises an illumination source 530 to help illuminate the eyes of the person. This illumination source 530 could project infrared light, near infrared light, or visible light in the direction of the person's eyes to help improve the sensitivity of the eye sensor 406 and make it less sensitive of other light sources, which may produce noise and/or glint.

In the embodiment shown in FIG. 8, the see-through display 402, head orientation sensor 404, and eye tracking camera 406, are connected to an electronic module 410. The electronic module 410, comprises a head orientation sensor signal pre-processor 412, that is connected to the head orientation sensor 404, an eye camera video processor 414, that is connected to an eye tracking camera (406), and a display interface 416, that is connected to the display 402. Inside the electronic module 410, the head orientation sensor signal preprocessor 412, the eye measuring camera video processor 414, and the display interface 416, are connected to a central processing unit 418. Also connected to the central processing unit 418, is a memory unit 420, and an interface and/or communications unit 422. The memory unit 420, can store multiple readings and results, which can be used for data logging, tracking of multiple users, and tracking of performance at various times. The interface and/or communications unit 422, can be connected to an external device 424. Transmission of signals between the communications unit 422, and the external device can be through a wired connection or a wireless connection using any connection method and/or protocol capable of being understood by anyone skilled in the art, including, but not limited to a serial protocol (such as USB), an ethernet protocol (such as TCP/IP), and a cellphone protocol (such as LTE). Additional elements that are not shown but might be included in the electronic module 410 can be a battery, a battery charge level indicator, and a power management module. The battery in the electronic module could be wirelessly charged. The worn device can contain a dual-purpose charging/connection port and this port could comprise a USB-C or a USB-Micro B connection. The connector on the other side of the charging cable could be a standard rectangular USB connector. The connection could be USB 3.0 or better. Communication between the electronic module 410, and the head worn unit can be through a wired connection or a wireless connection using any connection method and/or protocol including, but not limited to those described for the connection between the interface/communication unit 422, and the external device 424.

Note that the embodiment of the helmet shown at 400 in FIG. 8 could also comprise additional sensors 320 and 322, such as those described previously with reference to FIG. 5A. These additional sensors 320 and 322, could detect biometric, physiologic and/or biochemical parameters of the wearer of the helmet. The sensors could be connected to the electronic module 410, and more specifically to a bio-sensor interface 426, that communicates with the central processing unit 418, and the other parts of the system described herein.

The embodiment of the helmet shown at 400 in FIG. 8 could further comprise an airbag, such as the airbag shown at 330 in FIG. 5B. FIG. 8 does not specifically show an airbag (in order to keep this illustration simpler), but it can be understood that such an airbag would typically be located outside of the shell 202, which is shown in FIG. 8. The airbag would require an inflation interface, which is shown at 430 in FIG. 8. The inflation source is responsive to the central processing unit 418. The airbag inflation interface 430 could inflate the airbag in response to the detection of an impact by the head orientation sensor processor 412, or in response to device configured for sensing an impact before it occurs, such as a proximity detector, video camera, or information from the helmets of other players on a sports field.

Figure 9:
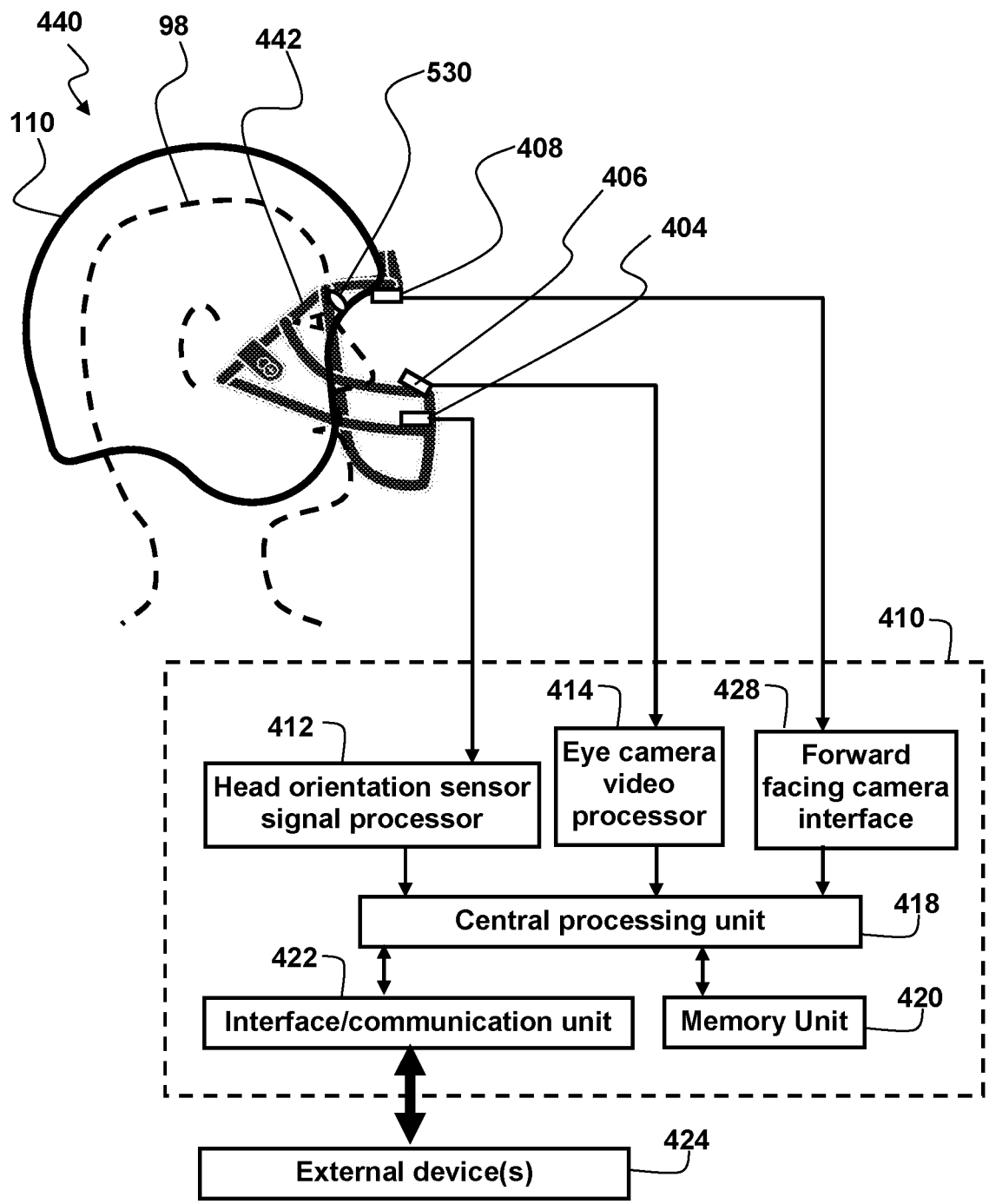
FIG. 9 shows a face guard that comprises an ocular performance measuring system.

Embodiments of the system and method described herein could also be applied to a face guard, or similar device, instead of or in addition to a helmet. FIG. 9 illustrates one example of a faceguard-based ocular performance measuring system 440. In this embodiment, the face guard frame is shown at 442. The face guard frame 442 could be rigid. The face guard frame 442, could comprise of the same types of materials previously listed for the helmet including carbon fiber, titanium, graphene. The face guard frame 442, could comprise eye sensing elements and/or transducers for detecting and measuring eye movements and a head orientation sensing element/transducer and circuitry to the electronic elements such as:

the head orientation sensor shown at 404, connected to the orientation sensor signal processor 412;
the eye-tracking digital video camera 406, connected to the eye camera video processor 414; and
the central processing unit 418, memory unit 420, and interface/communication unit 422 for communicating with an external device 424.

The helmet 110 in FIG. 9 could be a prior art helmet (such as 100 in FIG. 2A and FIG. 2D). The helmet 110 in FIG. 9 could be a helmet of the embodiments shown at 200 in FIG. 3 and FIG. 4A, 300 in FIG. 5A and FIG. 5C, 350 in FIG. 7A, 360 in FIG. 7C, and/or 370 in FIG. 7D. The helmet 110 in FIG. 9 could be any other helmet (hard or soft) capable of being understood by anyone skilled in the art.

The faceguard-based system 440, of FIG. 9 could have other sensors (320 in FIG. 8) interfaced with the electronic module 410, in the same way as was described for the helmet-based system in FIG. 8. The faceguard-based system 440, could have a display (402 in FIG. 8) and display interface (416 in FIG. 8) implemented in the same way as was described for the helmet-based system of FIG. 8. However, a display might be difficult for the person to use when active. As an alternative, the faceguard-based system 440, of FIG. 9 might have a forward-facing camera 408, that communicates with a forward-facing camera interface 428, in the electronic module 410. The forward-facing camera 408, can be responsive to the eye sensors to measure the ocular performance. In this case, the central processing unit 418, or the external device 424, could combine the information from the head orientation sensors 404, the eye-tracking digital video camera 406, and the forward-facing camera 408, to determine one of the ocular performance parameters described herein. The faceguard-based system could also comprise an illumination source 530 to help illuminate the eyes of the person. This illumination source 530 could project infrared light, near infrared light, or visible light in the direction of the person's eyes to help improve the sensitivity of the eye sensor 406 and make it less sensitive of other light sources, which may produce noise and/or glint.

Figure 10A:
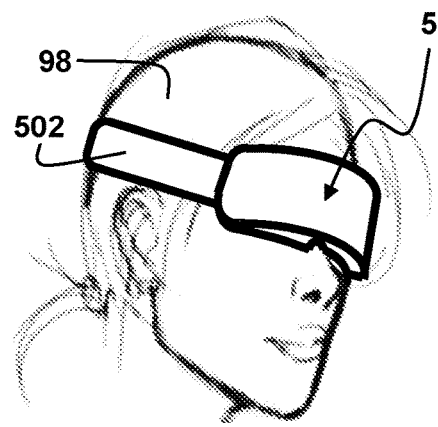
FIG. 10A shows a goggles embodiment of a head-worn virtual reality unit.
Figure 10B:
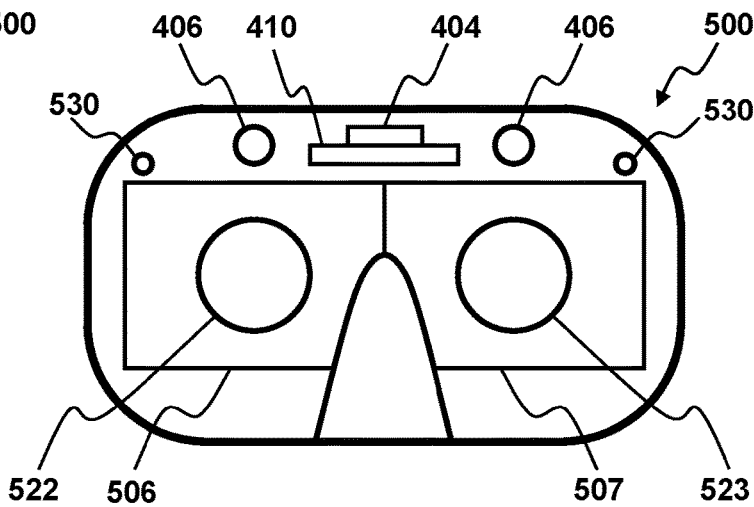
FIG. 10B shows the virtual reality unit of FIG. 10A when viewed from the inside of the goggles looking outward.

FIG. 10A and FIG. 10B show a virtual reality (VR) goggles embodiment of a head-worn device for measuring human ocular performance. FIG. 10A shows the head-worn VR device 500, attached to a person's head 98, with a strap or headband 502. FIG. 10B shows the head-worn VR device 500, when looked at from the inside looking outward. In the augmented device shown in FIG. 8, the display (402) was a see-through display and it only covered one eye or part of an eye. In the VR device of FIG. 10A and FIG. 10B, shown at 500, the left virtual reality display, shown at 506 and right virtual reality display 507, are opaque and the person is typically completely immersed in the scene being displayed. Other than the difference in displays, the VR goggles embodiment 500, can have many of the same elements and configurations that were described with respect to FIG. 8 and FIG. 9, including but not limited to the head orientation sensor 404, the eye tracking video camera(s) 406 (of which there can be one for the left eye and one for the right eye), and the electronic module 410. In order for the person's eyes to be able to focus on the displays (506 and 507), there are typically two lenses 522 (left eye lens) and 523 (right eye lens) between the person's eyes and the displays, 506 and 507, when the VR device 500, is worn normally by the person. Because the interior of the VR device 500 is not exposed to external light, there can be one or more illumination source(s) 530, to provide light that can be used by the video camera(s) 406 to sense ocular parameters such as eye or eyelid position or eye motion or any of the other ocular parameters described in other parts of this document. The illumination source or sources 530, can use infrared, near infrared, or visible light.

Referring specifically to the left and right eye tracking digital video cameras 406 in FIG. 10B, these cameras (more generally eye sensors) can be used for more than just the tracking of eye position in response to head movement. The eye sensors 406 can also be used to perform the following functions:

(a) The eye sensors could be used to provide control information. For example, the position of one or both of the eyes (or the orientation or movement of the eyes or eyelids) could be used to determine which of a plurality of choices a user has selected in a menu of options presented on a display. This selection could be to change the scene being displayed to the user. This selection could be used to turn something on or off.

(b) The eye sensors could be used to image one or both retinas of the person, to capture anatomic features of a retina, to capture motion and/or orientation of a retina, and/or to determine retinal image stability and/or foveal fixation.

Embodiments of the present invention could also be implemented with eye trackers (also described herein as eye sensors), shown for example at 406 in FIG. 8, FIG. 9, and FIG. 10B, which are not video cameras. Examples of non-video camera eye trackers can include electromyography trackers and electromagnetic trackers. Embodiments of the present invention could also be implemented with the use of a virtual retinal display providing an image directly on the retina of the user's eye.

Figure 10C:
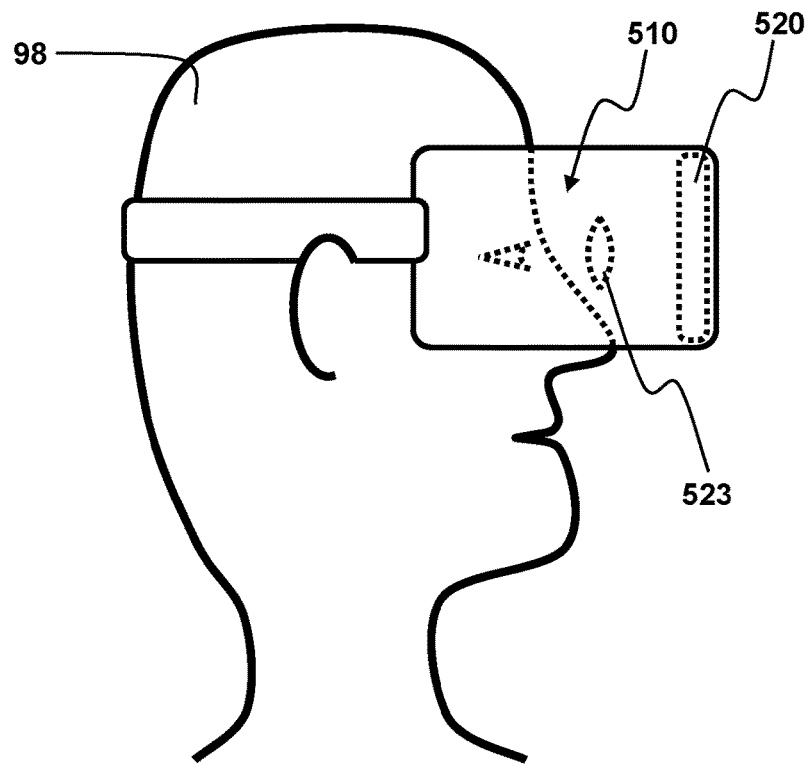
FIG. 10C shows head-worn virtual reality goggles comprising a smartphone.

FIG. 10C shows head-worn virtual reality goggles 510, comprising a smartphone 520. These goggles 510, use the smartphone 520, to provide the display, the eye tracking digital video camera, and the head tracker functionality, and doing many, or all, of the functions of the electronic module. To help the person's eyes focus on the display of the smartphone 520, these virtual reality goggles further comprise one or two lenses 522 and/or 523, that sit between the eyes of the person's head 98, and the smartphone 520. In the embodiment shown in FIG. 10C, the smartphone 520 can contain embedded software to perform all of the necessary functions of measuring all eye movements and/or ocular functions as well as measuring head movements. Alternatively, in another embodiment, the smart phone or smart device can be hand-held and the head and eye measurements for each eye discussed herein can be made from embedded software. As an example, head tracking and eye movements can be detected and measured to perform VOR testing. Instructional signals, such as when to rotate the head while looking a visual target, can be random to prevent the subject from anticipating the timing, in the form of visual cues, auditory signals or a haptic signal. Such signals could be provided through the smart phone. Calibration and other specific ocular parameters test measures can similarly be performed with the smart phone application. Data obtained can be logged and transmitted wirelessly to another smart device.

Figure 11:
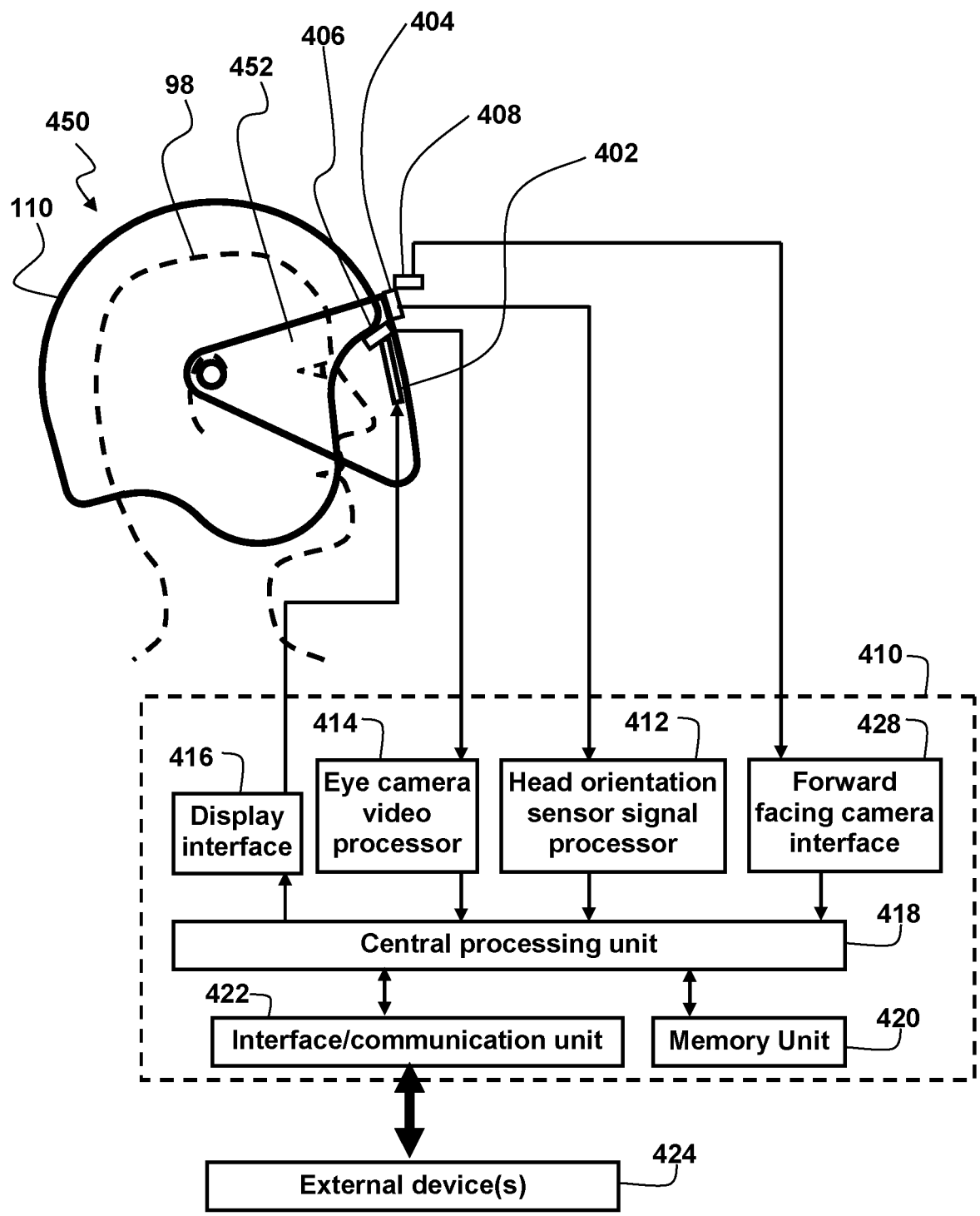
FIG. 11 shows a face shield that comprises an ocular performance measuring system.

FIG. 11 shows a face shield or visor embodiment of an ocular performance measuring system head-worn augmented reality unit 450. The faceshield/visor system 450, shown in FIG. 11 is similar to the helmet system, 400 in FIG. 8, and the faceguard system, 440 in FIG. 9 and could have any of the features and attributes of these other embodiments. The faceshield/visor system 450, could be electronically coupled to the electronic module 410, and this electronic module 410, could be part of the faceshield/visor system 450, or the electronic module 410, could be external to the faceshield/visor system 450, and communicate through a wired or wireless connection.

Figure 12A:
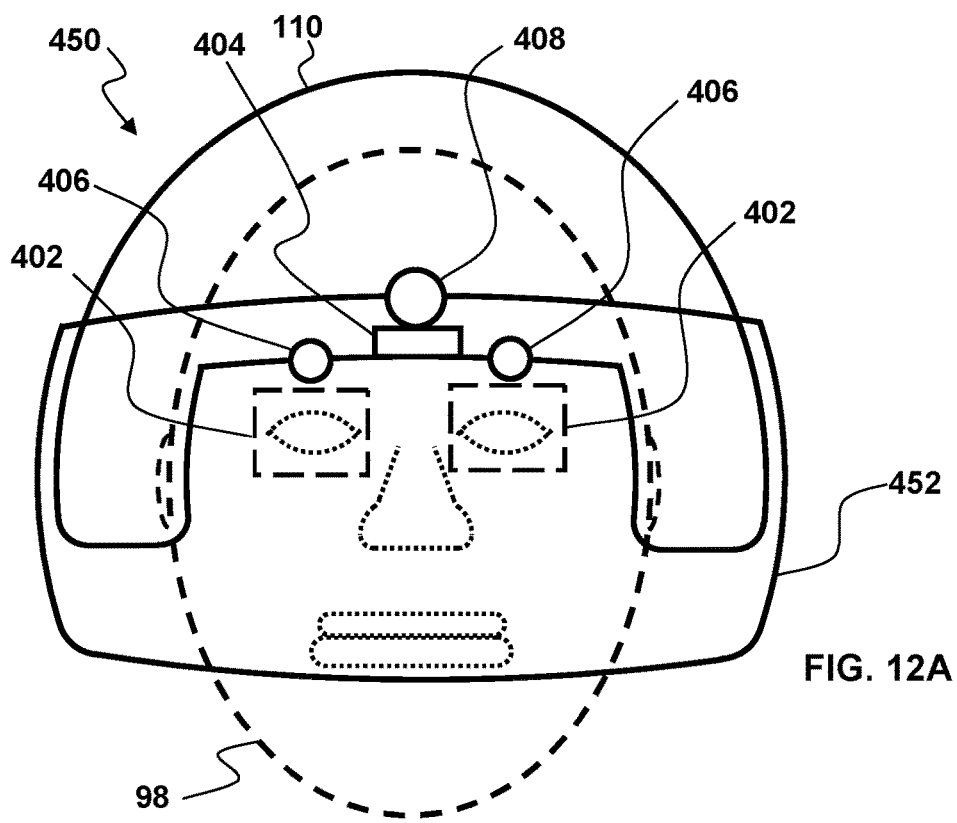
FIG. 12A shows a face shield comprising two micro light emitting diode see-through display panels.

FIG. 12A shows a front view of the faceshield/visor system 450 of FIG. 11, without the electronic module. The faceshield/visor system 450 in FIG. 11 and FIG. 12A, could be used for measurement of any human ocular performance parameter described herein. The faceshield/visor system 450 shown in FIG. 11 and FIG. 12A is configured to be worn on a person's head 98. The faceshield/visor system 450 can comprise: a see-through display 402; a head orientation sensor (head tracker) 404; an eye tracker 406, which could more specifically be an eye-tracking digital video camera; a forward-facing camera 408; a face shield or visor 452; and a helmet 110. The helmet 110 in FIG. 11 and FIG. 12A could be a prior art helmet (such as 100 in FIG. 2A and FIG. 2D). The helmet 110 in FIG. 11 and FIG. 12A could be a helmet of the embodiments shown at 200 in FIG. 3 and FIG. 4A, 300 in FIG. 5A and FIG. 5C, 350 in FIG. 7A, 360 in FIG. 7C, and/or 370 in FIG. 7D. The helmet 110 in FIG. 11 and FIG. 12A could be any other helmet (hard or soft) capable of being understood by anyone skilled in the art.

The electronic module 410 shown in FIG. 11 can comprise a display interface 416, an eye camera video processor 414, a head orientation signal processor 412, a forward-facing camera 428, a central processing unit 418, a memory unit 420, and an interface and/or communication unit 422 as shown and configured in FIG. 11. The electronic module 410 can be configured to communicate with an external device (or devices) 424 using any of the methods and systems described herein.

Figure 12B:
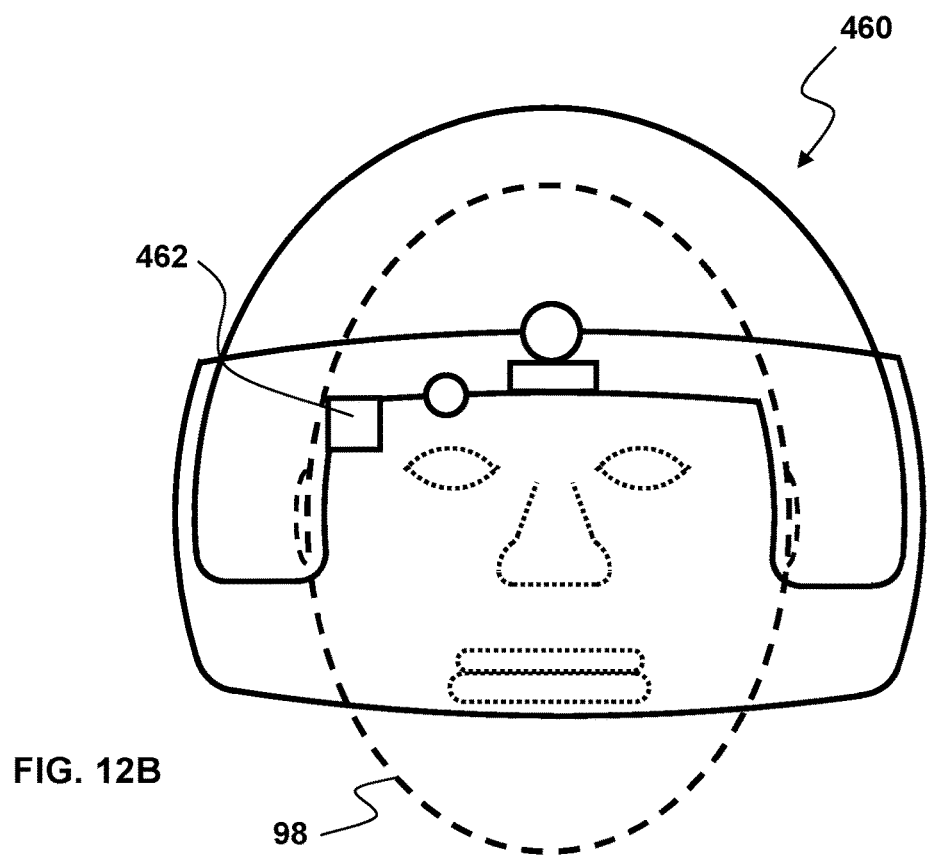
FIG. 12B shows a face shield comprising an augmented reality see-through prism.

FIG. 12B shows an alternate embodiment of the system shown in FIG. 11 and FIG. 12A. This alternate embodiment could more specifically be called a faceshield/visor based augmented peripheral vision ocular performance measuring system 460. The augmented peripheral vision system 460 in FIG. 12B differs from the see-through-display-based system 450 in FIG. 12A by having a peripheral vision display element 462 in FIG. 12B instead of the see-through display (or augmented reality display) 402 in FIG. 12A. The peripheral vision display element 462 can be implemented in any way capable of being understood by anyone skilled in the art, including the use of any optical elements described in U.S. Pat. No. 9,075,249 (Google Glass). The advantage of a peripheral vision display element 462 is that, because it is in a person's peripheral vision, the display element does not need to be see-through.

It is possible to have other embodiments of ocular performance-based head impact measurement systems and methods that use some of the elements shown in FIG. 11, FIG. 12A, and FIG. 12B. An example of such an alternate embodiment would be an ocular performance-based head impact measurement system (or method) that uses a virtual retinal display, as described in U.S. Pat. No. 5,659,327, instead of the see-through display (402 in FIG. 11 and FIG. 12A) or the peripheral vision display element (462 in FIG. 12B). Such an alternate embodiment could further include having an augmented reality display or displays in any configuration capable of being understood by anyone skilled in the art, such as the augmented reality virtual retinal displays described in US Patent Application Publications 2015/0016777 and 2018/0160956 (Magic Leap).

Figure 13A:
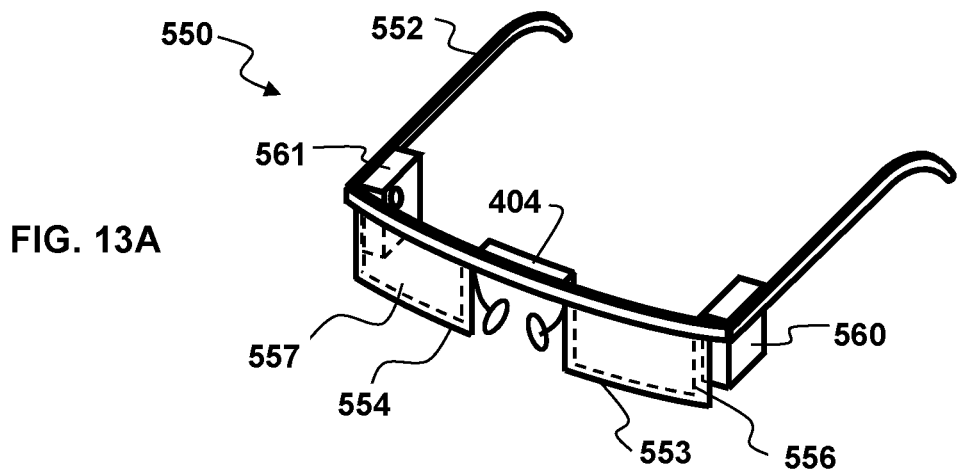
FIG. 13A shows an eyeglasses embodiment of a head-worn augmented reality unit.

FIG. 13A shows an eyeglasses embodiment of a head-worn device for measuring human ocular performance 550. The eyeglasses unit 550, shown in FIG. 13A is similar to the helmet-based unit 400, shown in FIG. 8, the goggles-based unit in FIG. 10B, and the face shield unit 450 in FIG. 11 and could have any of the features and attributes described and shown with these other embodiments. The eyeglasses unit 550 in FIG. 13A, could be electronically coupled to an electronic module 410, and this electronic module 410 could be part of the eyeglasses unit 550, or the electronic module 410, could be external to the eyeglasses unit 550, and communicate through a wired or wireless connection. The eyeglasses unit 550, could be used for measurement of any human ocular performance parameter. The eyeglasses unit 550, comprises a spectacles frame 552, which is attaches the eyeglasses unit 550 to a person's head. The eyeglasses unit 550 also comprises a left eyeglass 553, and a right eyeglass 554. The left and/or right eyeglasses could be lenses, they could be clear windows, or they could be translucent windows. Also shown are a left display 556, and a right display 557. In the embodiment shown in FIG. 13A, the displays, 556, and 557, are see-through displays that are located between the left and right eyeglass, 553, and 554, and the eyes of the person. When the displays, 556, and 557, are in this location, it is not as obvious to an outsider that the unit 550 is a head-worn system for measuring ocular performance. The displays, 556, and 557, could also be external to the left and right eyeglasses 553, and 554. In another embodiment, the displays, 556, and 557, could be located within the eyeglass unit, 554, and 555. There could be only one display, 556, or 557. The display could be off-bore and only visible in a person's peripheral vision, such as the embodiments shown in U.S. Pat. No. 9,075,249.

Further referring to FIG. 13A, the eyeglasses unit also comprises a head orientation sensor located in the bridge 404, a left eye tracking digital video camera 560, and a right eye tracking digital video camera 561. All of these components can be connected similarly and, in any configuration, and combination to other embodiments described herein. The embodiments shown in FIG. 8, FIG. 11, FIG. 12A, FIG. 12B, and FIG. 13A can be considered augmented reality implementations. In these augmented reality units, the display could be see-through or opaque. If it is opaque, it could cover part or all of the field of view. If it is see-through or opaque and covers only part of the field of view, it could be in one eye or both eyes. If it is opaque and covers the entire field of view, it can only be in one eye. The augmented reality display(s) in these embodiments can provide an image of interest or a target for the user to focus on. This image of interest (or target) could be a circular object, such as a pool ball. This image of interest or target could be static (not moving) in the field or view or it could be dynamic (i.e., moving in the field of view).

Figure 13B:
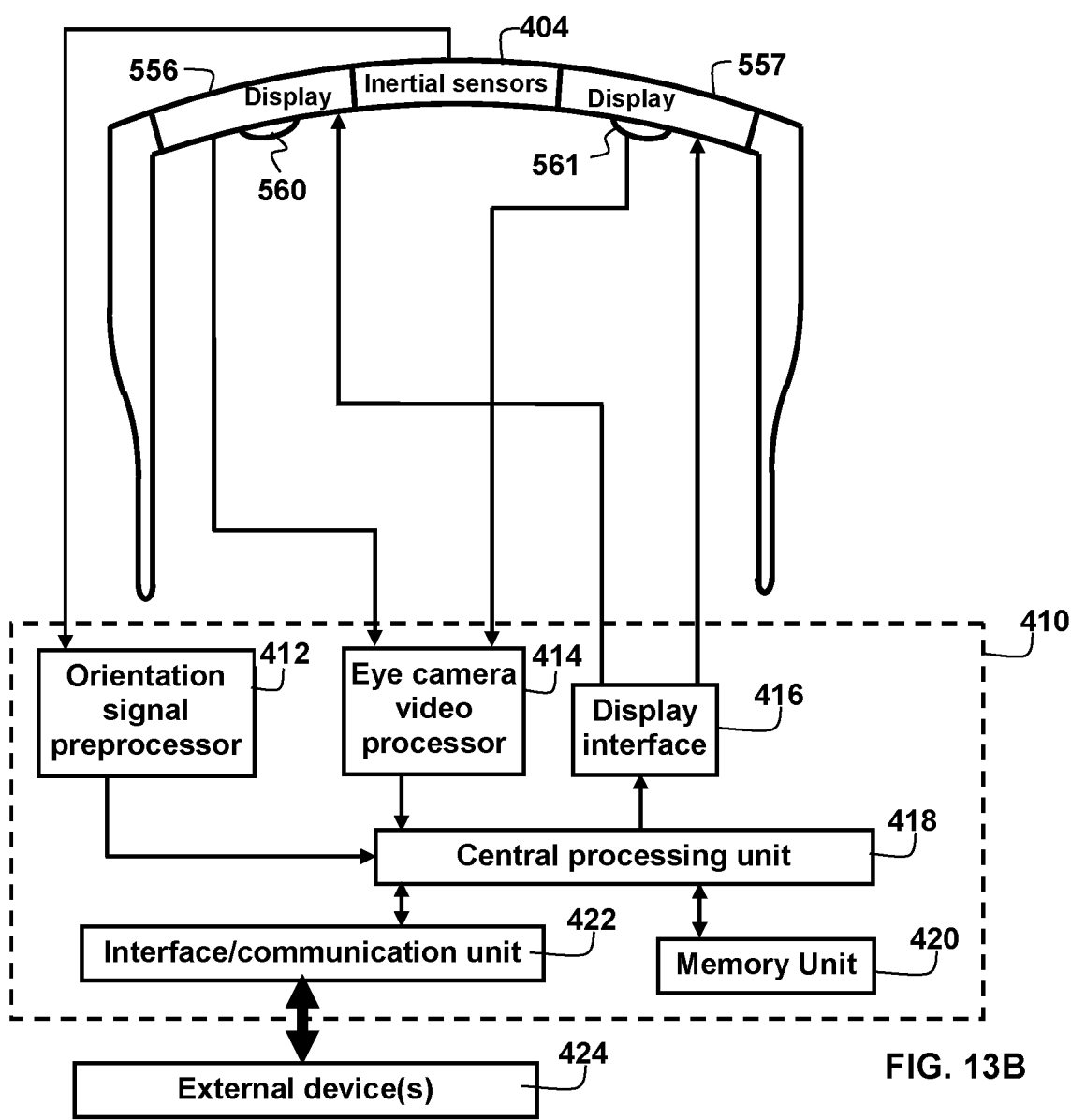
FIG. 13B shows a top view of an augmented reality or virtual reality system.

FIG. 13B shows a top view of an augmented reality or virtual reality system that also includes the main elements that were shown in the systems of FIG. 10A to FIG. 13A, including a head orientation sensor 404, a left display 556, a right display 557, a left eye tracking digital video camera 560, a right eye tracking digital video camera 561, an electronic module 410, an orientation signal processor 412, an eye camera video processor 414, a display interface 416, a central processing unit 418, a memory unit 420, an interface/communication unit 422, and an external device 424. An alternate embodiment can include a forward-facing camera 408, like that previously described in FIG. 9, that communicates with a forward-facing camera interface 428, in the electronic module 410. The forward-facing camera 408, can be responsive to the eye sensors to measure the ocular performance.

It should be noted that the AR and VR embodiments of the inventions disclosed herein can also be implemented using computer-generated 3-dimensional synthetic information instead of the monoscopic or stereoscopic "reality" information used for the augmented reality (AR) and virtual reality embodiments discussed herein.

Figure 14:
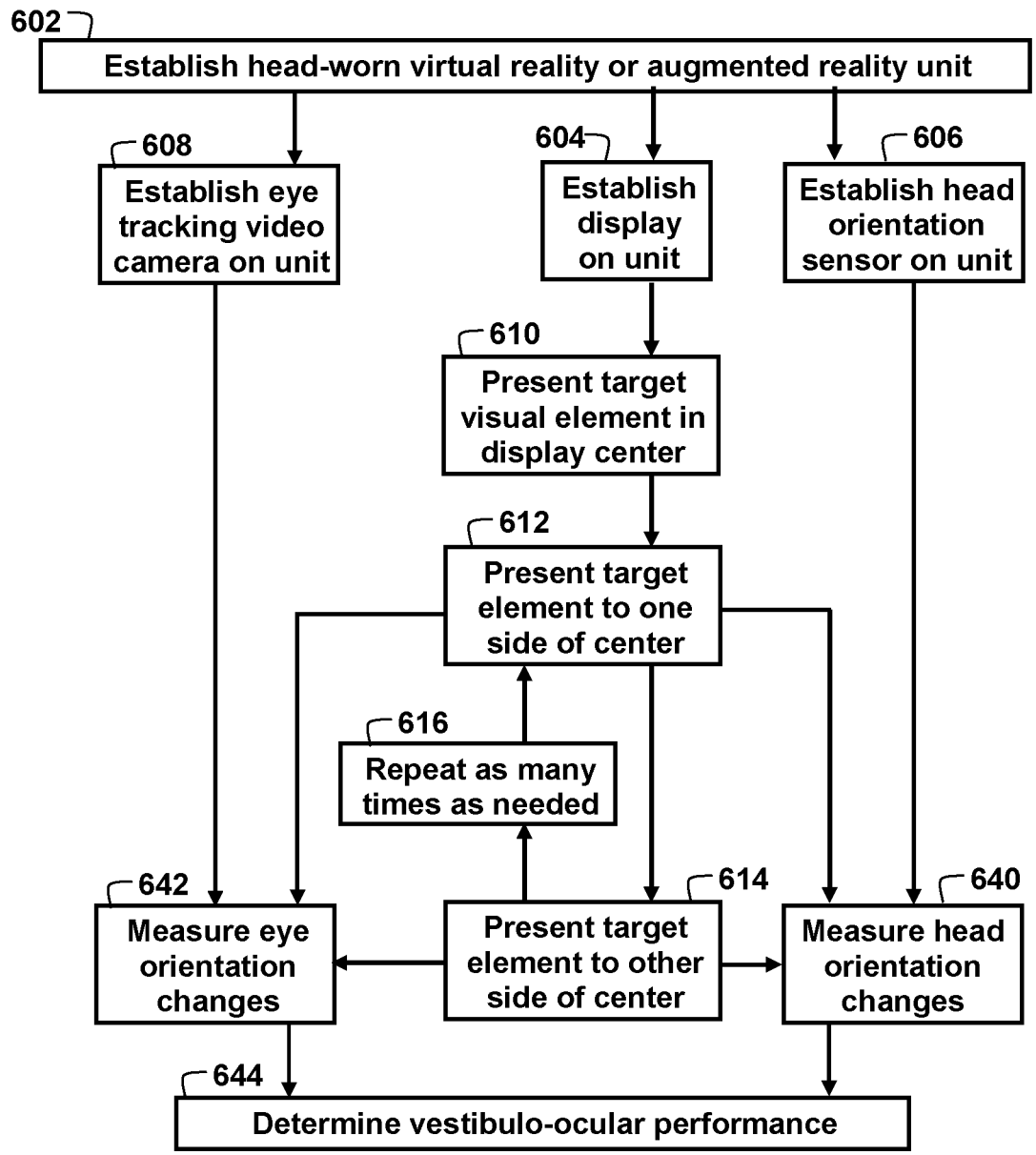
FIG. 14 shows an ocular performance calibration test method.

FIG. 14 shows an example of a vestibulo-ocular performance calibration test that can be implemented using a head-worn AR/VR unit. This test comprises the following configuration and steps:

The AR/VR unit 602, comprises a display 604, a head orientation sensor 606, and an eye tracking video camera 608.

Head: In this test, the subject is asked to keep his/her head motionless or the head is constrained to keep it motionless. The head orientation sensor 606, is used to verify that the head is stationary.

Eyes: The subject is asked to track a visual target element of interest by moving his/her eyes. The eye sensor (typically a video camera) measures the subject's eye movement 642, as visual elements are displayed.

Display: The display background is subdued, plain, solid, and/or non-distracting. In this test, the display background is similar to the background that has been used in prior art VOR testing in which the subject is asked to look at a solid colored wall which has a bright white circular dot (the target visual element of interest) projected on it. In the AR/VR embodiment of this test, the display background on the head-worn device is similar to the wall of the prior art test. The display also presents a target visual element of interest that can be similar the projected white circular dot of the prior art clinical test or it can be visually enhanced for better image or target eye fixation. The target visual element of interest then behaves in the following way:
1. The target visual element is initially displayed centrally 610.
2. It is then displayed off center on a first side (left or right) of the display center as the central image is dimmed, as shown at 612. This is typically about 20-25 degrees off center.
3. It is then displayed off center on the opposite (or second) side of the display center as the previous image to the first side is dimmed, as shown at 614. This is also typically about 20-25 degrees off center.
4. This process of dimming or removing the target visual element of interest on one side and displaying it on the opposite side is repeated as many times as needed, as shown at 616.
5. This test can be conducted in the vertical, as well as the horizontal direction.

Processor: The processor in the AR/VR system then compares eye movement to timing and appearance/disappearance of visual elements on display, and the location of these visual elements to determine vestibulo-ocular performance 644. Performance could be measured as accuracy, gain, phase, symmetry, velocity, saccades, and/or visual acuity.

Figure 15:
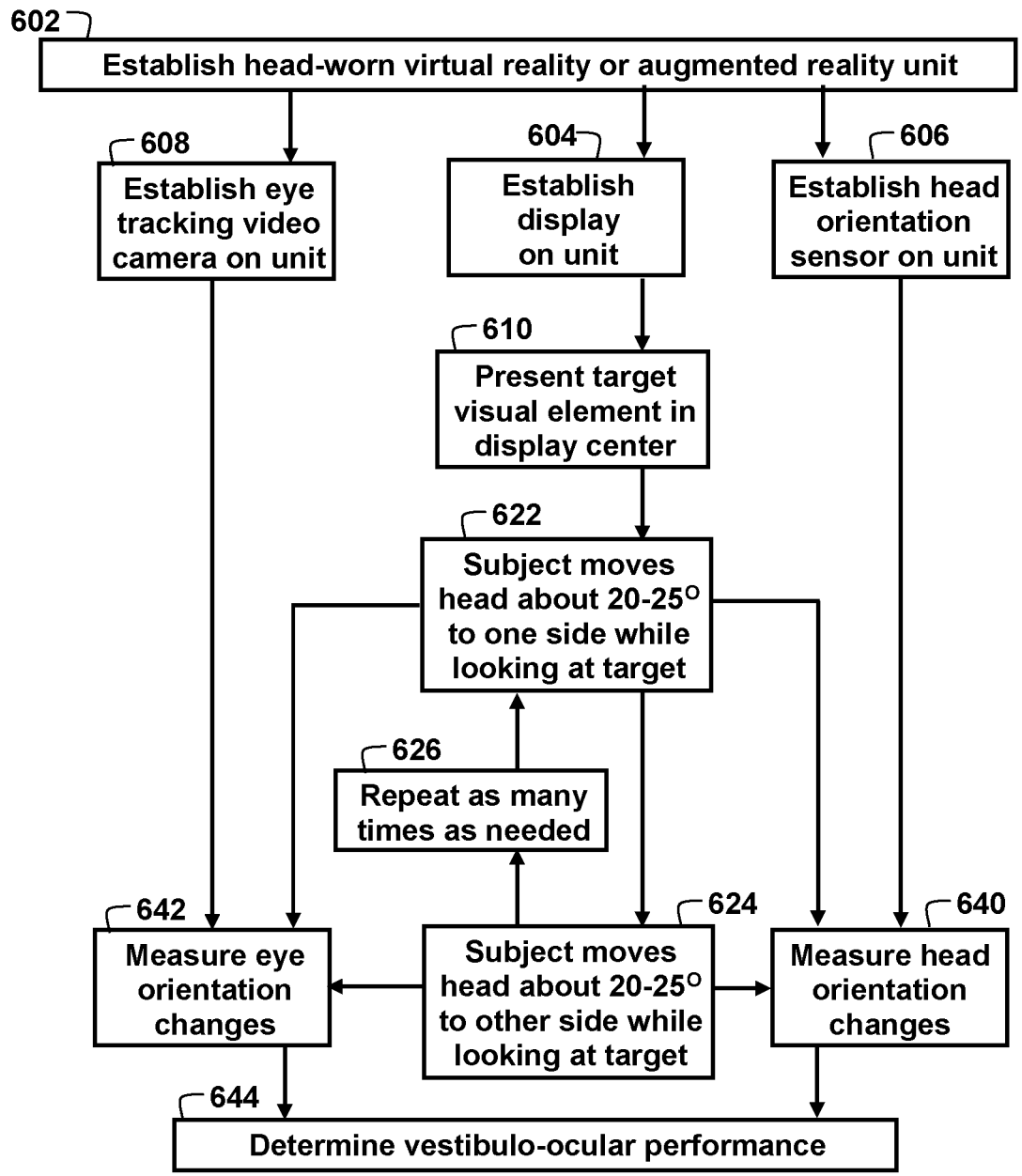
FIG. 15 shows a static active ocular performance test method.

FIG. 15 shows an example of static active vestibulo-ocular performance testing that can be implemented in a head-worn AR or VR unit. This test comprises the following configuration and steps:

The head-worn AR/VR unit 602 comprises a display 604, a head orientation sensor 606, and an eye tracking video camera 608.

Display: In this test, the display is static—neither the background nor the target visual element of interest moves or changes in any way. The display comprises a subdued background and a centered white circular dot or visually enhanced target element 610, similar to what was described with reference to the test shown in FIG. 14.

Head: In this test, the subject is asked to actively move his/her head each time he/she is given a cue signal. The head should typically move about 20-25 degrees off center about a vertical axis (i.e., left or right). The head orientation sensor measures changes in head pitch, roll, and/or yaw 640.

Eyes: The subject is instructed to keep his/her eyes focused on the target visual element as the head moves. The eye sensor (typically a video camera) measures eye movement 642, relative to head movement 640.

Cues are provided to tell the subject when to move the head. These cues can be audio cues. The cues could be haptic (i.e., vibration on the side of the person's head). The cues could be visual (i.e., change of color or intensity of the visual target element of interest). The cues are typically timed randomly so the subject doesn't try to anticipate the timing.

The test sequence is as follows:
1. The subject is instructed to move the head about 20-25 degrees in one direction when a first cue is given, and to hold the head in this new position 622.
2. The subject is instructed to move the head back about 20-25 degrees when the second cue is given 624.
3. The subject is instructed to move the head in the first direction a second time when the third cue is given.
4. The process is repeated as many times as needed 626.
5. This test can be conducted in the vertical, as well as the horizontal direction.

Processor: The processor in the AR/VR system then compares eye movement to timing and appearance/disappearance of visual elements on display, and the location of these visual elements to determine vestibulo-ocular performance 644. Performance could be measured as accuracy, gain, phase, symmetry, velocity, saccades, and/or dynamic visual acuity.

Figure 16:
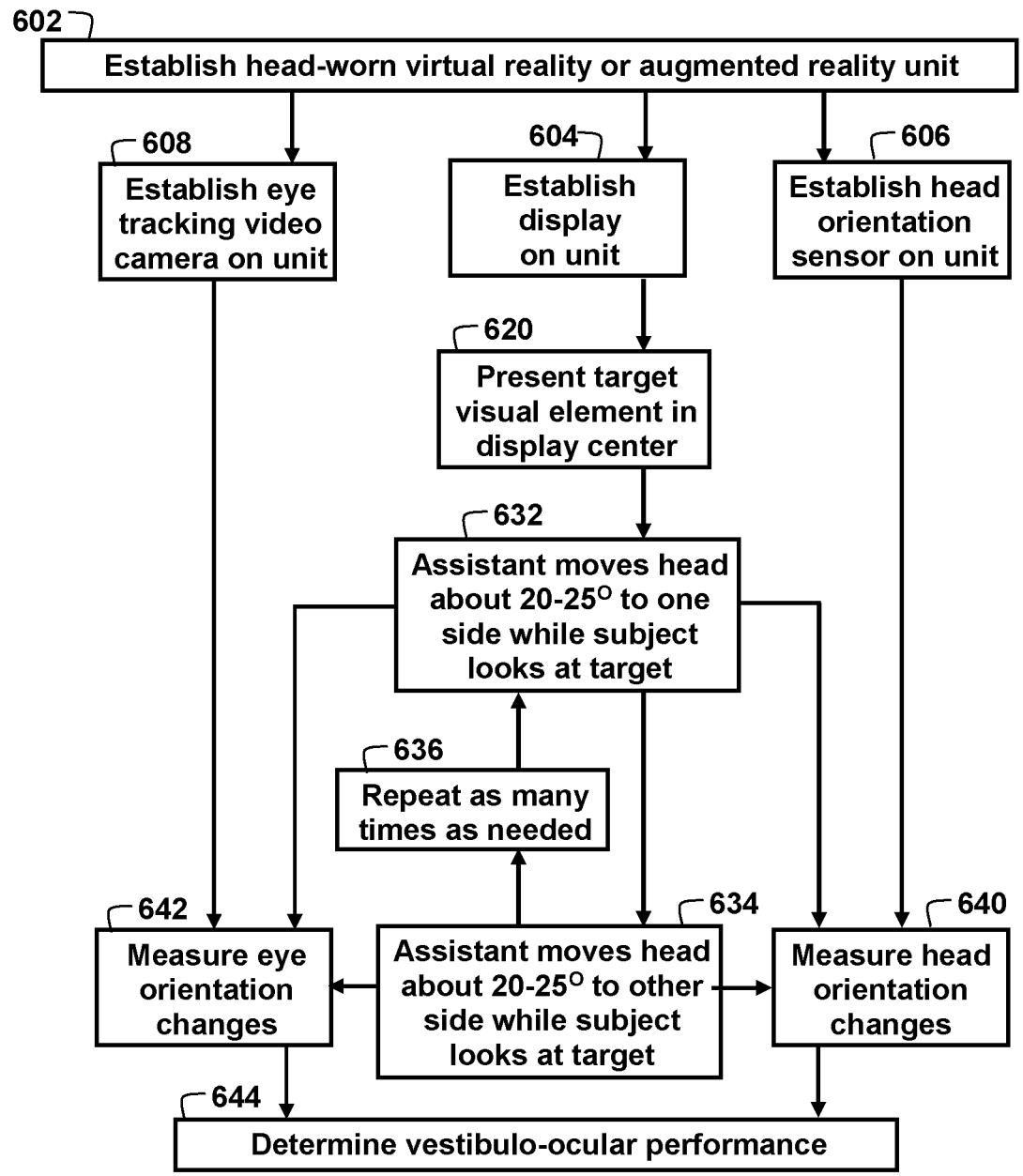
FIG. 16 shows a static passive ocular performance test method.

FIG. 16 shows a static passive vestibulo-ocular performance test that can be implemented in a head-worn AR or VR unit. This test comprises the following configuration and steps:

The head-worn AR/VR unit 602, comprises a display 604, a head orientation sensor 606, and an eye tracking video camera 608.

Display: In this test, the display is the same as for the test described with reference to FIG. 14 and FIG. 15, with a target visual element presented in the center 610.

Head: In this test, the assistant holds the subject's head and moves it about 20-25 degrees each time 632. The head orientation sensor measures changes in head pitch, roll, and/or yaw 640.

Eyes: The subject is instructed to keep his/her eyes focused on the target visual element as the head moves. The eye sensor (typically a video camera) measures eye movement relative to head movement 642.

The test sequence is as follows:
1. The assistant moves the subject's head about 20-25 degrees in one direction and then holds it in this new position 632.
2. The assistant then moves the head back in the opposite direction, 20-25 degrees and holds it 634.
3. The assistant moves the head in the first direction a second time.
4. The process is repeated as many times as needed 636.
5. This test can be conducted in the vertical, as well as the horizontal direction.

Processor: The processor in the AR/VR system then compares head movement and eye movement to determine vestibulo-ocular performance 644. Performance could be measured as accuracy, gain, phase, symmetry, velocity, saccades, and/or dynamic visual acuity.

There can be many additional embodiments of the ocular performance tests described with reference to FIG. 14, FIG. 15, and FIG. 16. Some of these embodiments can include combinations of the variations listed here:

a. The visual target element (an example of which would be a white dot or a visually enhanced target element) can be any other shape, size, or coloring or have any other features capable of being understood by anyone skilled in the art. Examples of these variations in the target visual element could include:
A different shape (such as a shape comprising a cross hair);
Different contrast, either more or less;
Different intensity;
Different size;
Different focus, either more in-focus or out of focus;
Having one or more features in the visual element that move relative to the rest of the visual element;
Different depths;
The appearance of a natural object (such as a baseball, a basketball, or a bird); and/or;
Any combination of any of the above.

b. The test shown in FIG. 15 and/or FIG. 16 could be run with the target visual element not being stationary. This would make the overall test more similar to a natural environment in which the head, the eyes, and the visual world are all moving relative to one another and relative to a stationary reference frame at all times. When implemented on a display in an AR/VR environment, this would mean that the target visual element could:
Move with the head movement;
Move contrary to the head movement;
Move perpendicular to head movement; and/or
Move in any random pattern not associated with head movement c. The background (traditionally subdued, plain, solid, and/or non-distracting) could be presented on the display of the AR/VR system as any other background understood by anyone skilled in the art. Examples of variations of the background can include embodiments in which the background is more natural and similar to actual scene and/or any of the variations in the following list:
The background can be completely static;
The background can have moving and/or flashing elements;
The background can be enhanced with auditory distractions consistent with the imagery being displayed;
The background can be in or out of focus;
The background can be low intensity/contrast or high intensity/contrast relative to target of interest;
The object of interest or image can utilize foveated rendering, in which only the target of interest which the user is visualizing is seen clearly, where the fovea is focused, and the remainder of the adjacent region is less detailed.

Visual acuity, visual fixation ability, DVA (dynamic visual acuity) and FVS (foveal visual stability) can be tested using a system and method similar to the vestibulo-ocular performance (VOP) test shown in FIG. 15 and/or FIG. 16. The following are the main elements of a DVA or FVS test performed in this way using a VR or AR environment:

Step 1. Perform a routine vision test by presenting a Snellen chart, or something similar, using the display of the AR/VR unit. This is needed to establish a baseline visual acuity in a static environment. This static test does not necessarily need to be done with a Snellen chart (the standard chart used by optometrists and ophthalmologists), it could also be done by asking the subject to identify characters of various sizes, positions, and/or locations.

Step 2. The subject is presented a visual element (such as a number or letter) in the display center in a manner similar to step 610 of FIG. 15, but in the case of a DVA or FVS test, the target visual element also comprises a character that the subject must identify.

Step 3. The size and character of the target visual element in the display center changes at random times while the subject is performing the steps described at 622, and 624, in FIG. 15 and/or 632 and 634 in FIG. 16.

Step 4. The subject speaks out the character observed each time it changes.

A VR/AR environment can also be used for positional testing. For example, VR goggles can be configured to display a background that has illumination, but no definable image that might provide orientation information to the subject. The subject, could then be asked to turn the head left, right, lie supine, while supine head turns right, head turns left, then turn the body (roll) right and turn the body (roll) left. During each positional change, the eyes are tracked using the AR/VR system to look for abnormal eye movements. If a target visual element was visible during this testing the nystagmus would be suppressed. However, elements with poor contrast can be displayed to provide a more immersive test environment. Visual elements in this instance should not have defining characteristics that might enable eye fixation.

A subject can be tested for BPPV using the method shown in FIG. 16 with the assistant moving the head in a specific pattern that allows the individual semicircular canals to be tested. Note that this means the head is not moved the 20 degrees side-to-side, but is instead moved based on standard protocol for the specific semicircular canal being tested.

Figure 17A:
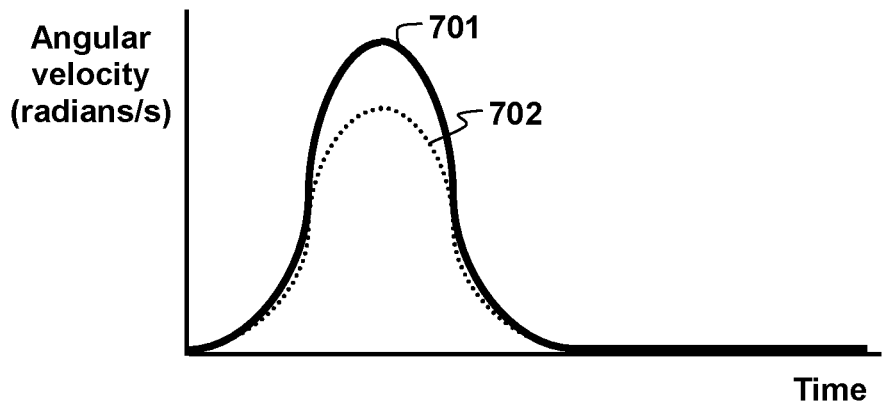
FIG. 17A shows a vestibulo-ocular gain measurement.
Figure 17B:
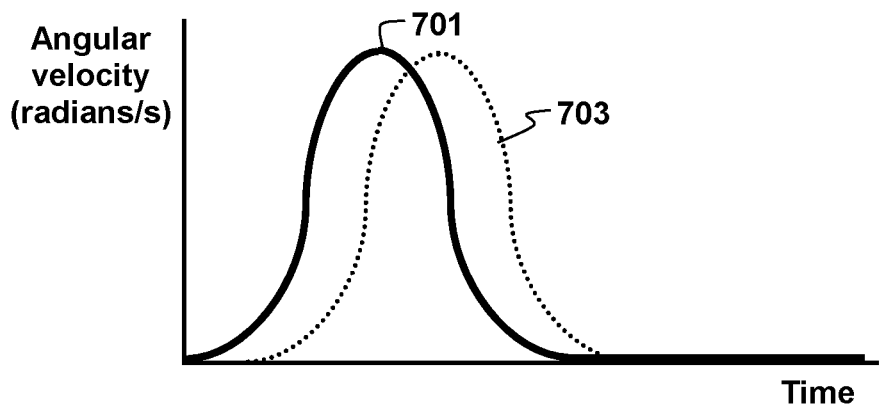
FIG. 17B shows a vestibulo-ocular phase measurement.
Figure 17C:
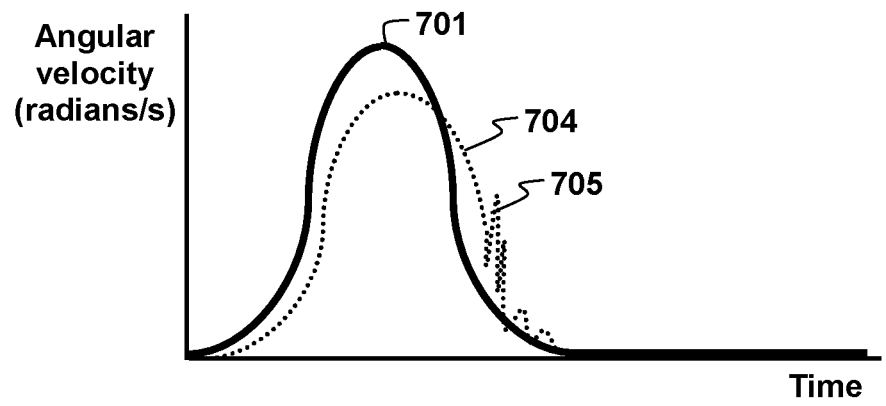
FIG. 17C shows ocular saccades.

FIG. 17A, FIG. 17B, and FIG. 17C provide graphs of time versus angular velocity that show how ocular response to a vestibular input can be measured. In these figures, the input is a rotation of the head, which is shown as the solid line at 701. This head rotation information would typically be measured using the head orientation sensor 404, that has been shown in FIG. 8, FIG. 9, FIG. 10B, FIG. 11, FIG. 12A, and FIG. 13B. The output is the eye response to the head rotation, which is shown as the dotted line at 702, 703, and 704, and would typically be measured using the eye sensor, which is typically an eye tracking digital video camera 406, such as that shown in FIG. 8, FIG. 9, FIG. 10B, and FIG. 11. The actual eye response is in the direction opposite of the head rotation, 701, but it has been plotted in the same direction to make it easier to compare the input and output of a person's vestibulo-ocular system. In FIG. 17A, the velocity of the eyes is slower than that of the head, which results in a gain of less than 1.0 (i.e., a loss of amplitude 702). In FIG. 17B there is a delay between the rotation of the head and the rotation of the eyes, which results in a phase lag, 703. In FIG. 17C, the eye rotation also lags the head rotation as shown at 704, but is caught up by saccades 705 near the end of the rotation.

Figure 18A:
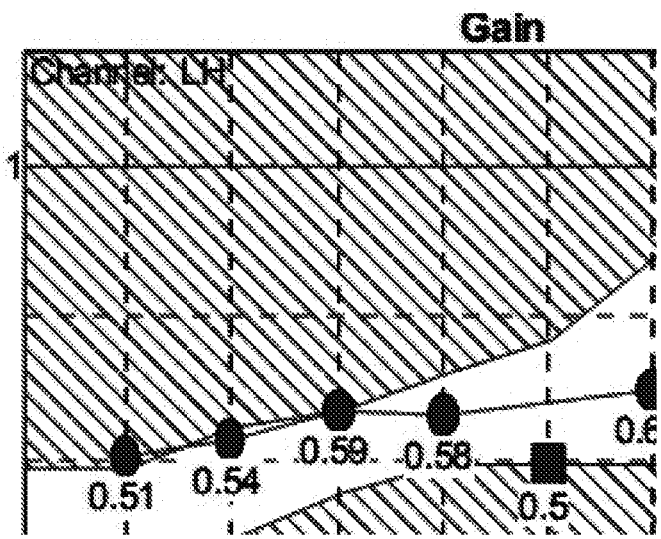
FIG. 18A illustrates an example of the left eye gain of a healthy person's vestibulo-ocular response to motion between 0.1 Hertz and 1.28 Hertz.
Figure 18B:
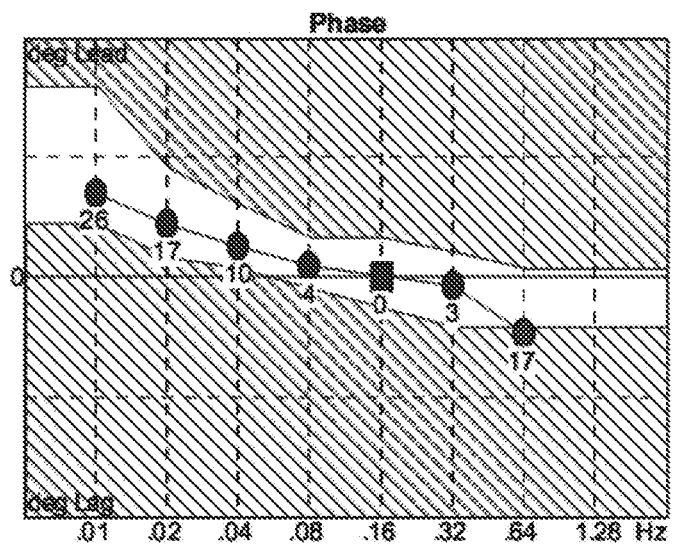
FIG. 18B illustrates an example of the phase lead and lag for a health healthy person's vestibulo-ocular response to motion between 0.1 Hertz and 1.28 Hertz.
Figure 18C:
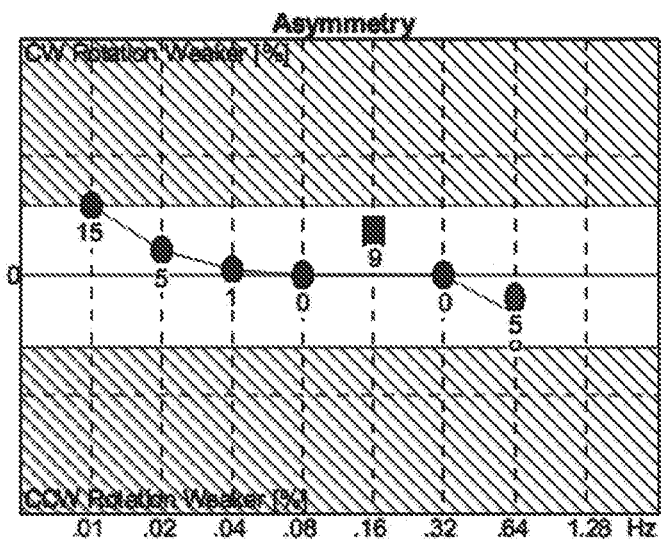
FIG. 18C illustrates an example of the asymmetry readings between counterclockwise and clockwise horizontal rotation of a healthy person's vestibulo-ocular response to motion between 0.1 Hertz and 1.28 Hertz.

The measures shown in FIG. 17A, FIG. 17B, and FIG. 17C, can be plotted at different frequencies and compared between the left eye and the right eye to create the plots shown in FIG. 18A, FIG. 18B, and FIG. 18C, which illustrate some typical eye responses to oscillation of a healthy person's head (e.g., vestibulo-ocular responses) in a horizontal plane at frequencies ranging from 0.1 Hertz (1 cycle every 10 seconds) to 1.28 Hertz (approximately 5 cycles every 4 seconds). More specifically, FIG. 18A shows the gain at these frequencies, FIG. 18B shows the phase lead and lag at these frequencies, and FIG. 18C shows the relative symmetry (or asymmetry) between clockwise and counter-clockwise oscillations. It should be noted that 0.1 Hertz to 1.28 Hertz is typical for the range of frequencies being used by prior art VOR testing systems. The embodiments described in this disclosure can include any frequency in the range of 0.01 Hertz (1 cycle every 100 seconds) to 15 Hertz (approximately 15 cycles every second).

FIG. 19A, FIG. 19B, FIG. 20, FIG. 21, FIG. 22, and FIG. 23 relate to targets or visual elements that could be projected without the use of VR or AR displays or presented on a VR or AR display to facilitate measurement and/or improve ocular performance parameters such as vestibulo-ocular reflex function, visual pursuit, vergence, DVA, or other ocular parameters discussed herein. These targets or visual elements can be designed to enhance the eye fixation on the displayed image when the head is motionless and the visual element is in motion. These targets or visual elements could also be designed for when the head is in motion and the visual element is motionless or when both the head and the visual element are in motion. In embodiments of the invention, projection of visual elements without the use of VR or AR displays or when using either VR or AR display systems, the displayed targets or visual elements can be static in a position or location or the displayed targets or visual elements can be dynamically changing in position, depending on the specific test being performed or rehabilitation method being used. The targets or visual elements, upon which the eyes are attempting to focus, can be of a variety of colors, sizes, shapes, and forms. They can change in color, size, shape, and form. They can contrast with other items being displayed to be more or less dominant in order to provide visual weight to enable fixation. These targets or visual elements can use specific colors with more saturation and can change in scale and proportion, all in an effort to draw the fovea toward a specific point of fixation on the target or visual element. With stereoscopic or 3-dimensional viewing, foveated rendering can also allow the image of interest to be seen in detail seen clearly and the remaining adjacent region is less detailed. Without using such enhancements to what is displayed, when performing VOR, DVA, or other ocular performance testing, the eyes tend to wander and have more microsaccades, which decrease the fixation ability and lessens the attentiveness of the person performing the test and the accuracy of testing. Generally, it is important to have some small point of focus on the visual element to lessen the microsaccades and enhance the fixation ability. These same targets or visual elements can be used for any oculomotor or ocular performance testing including VOR re-training when a VOR abnormality exists.

The ideas expressed in the previous paragraph can best be explained by looking at some examples. FIG. 19A shows an example of a target or visual element in the form of a soccer ball 902. This soccer ball could be part of an existing scene viewed on a VR or AR display or viewed through an AR display or the soccer ball could have been added to the scene. The soccer ball could be spinning, which might make the pattern on the ball distracting. FIG. 19B shows the visual element (soccer ball) of FIG. 19A that has been altered by defocusing the ball 904, and superimposing a target in the form of a cross-hair 906, that is more precise for the eyes to focus on. It would be more accurate fixation for the eyes to focus on the center of the cross-hair element shown in FIG. 19B than the element shown in 19A due to the shape, size, contrast, and suppression of the pattern on the ball. Although this example has been done using a black and white image, color and color contrast can be more effective. For example, the visual element seen in the VR or AR platform display could be a red colored ball and within the center of the ball or a dark cross-hair surrounded by a lighter yellow circle could be placed. This strongly contrasted central focal point could help the eye focus on a specific point and lessen the "eye scanning" while undergoing any ocular performance measurement such as VOR testing or VOR re-training. In another example, the element being viewed can be in the shape of a familiar object, such as a basketball, football, helmet or object used in one's occupation. It can also have a centered focal point, created by high contrast and high color saturation compared to the surrounding background to maintain the foveal fixation duration attractiveness and lessen microsaccades.

FIG. 20 shows a scene that can be used for optokinetic testing in a virtual or augmented environment. In traditional optokinetic testing, a person's head is motionless while seated inside a moving drum with alternating black and white vertical lines or alternatively, a hand-held drum, with alternating black and white vertical lines, is placed in front of the person. The drum is slowly rotated. The alternating lines induce nystagmus and cause visually induced motion sickness. The movement of the eyes is measured as the drum rotates left and then right. Measurements can be at different drum speeds. This same test can be performed using an AR or VR platform by creating a visual image that includes elements that work just like the vertical lines in the drum. Examples of natural scenes that are similar to the drum with lines can include examples such as being seated in a car and watching a train go by or driving and watching the telephone poles move by, such as the scene 910 shown in FIG. 12. Similarly flying objects can be visualized as moving across the visual field or along another plane of motion beside the person. These visual elements can also change in size, color or other dimensions, as the person gets closer to the virtual object or further from the visual element. Motion can occur in any direction or depth relative to the person, as the eye movement is being assessed and measured.

Figure 21:
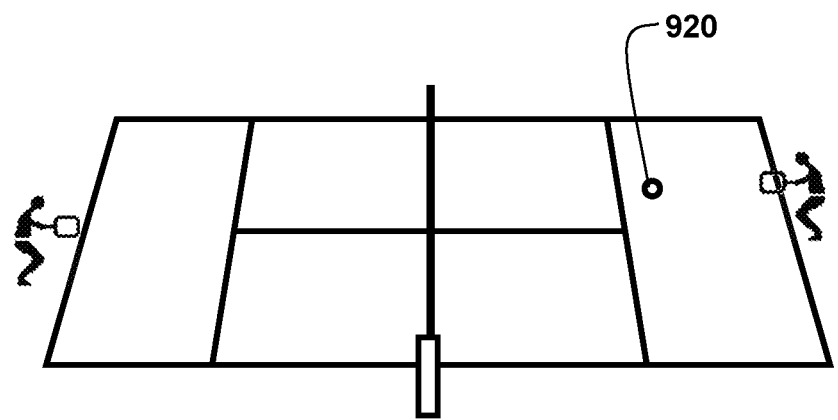
FIG. 21 shows a scene that can be used for testing eye-tracking performance.
Figure 22:
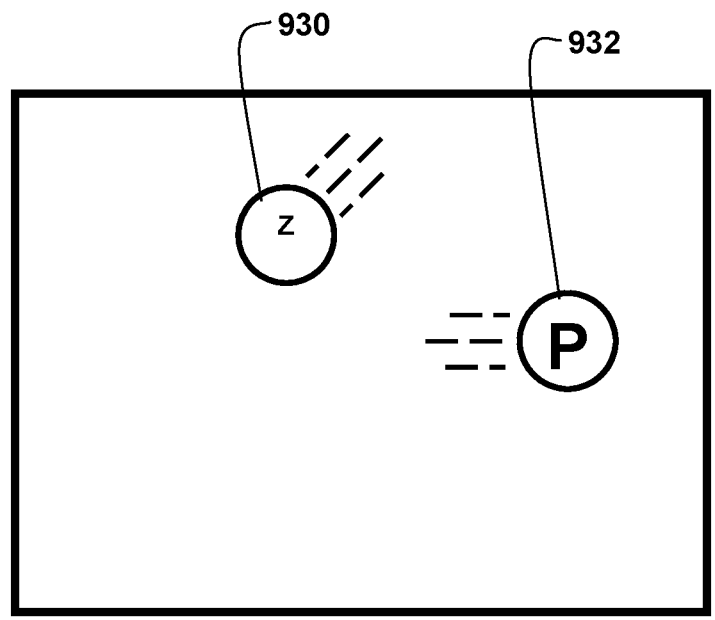
FIG. 22 shows a scene that can be used for dynamic visual acuity testing.
Figure 23:
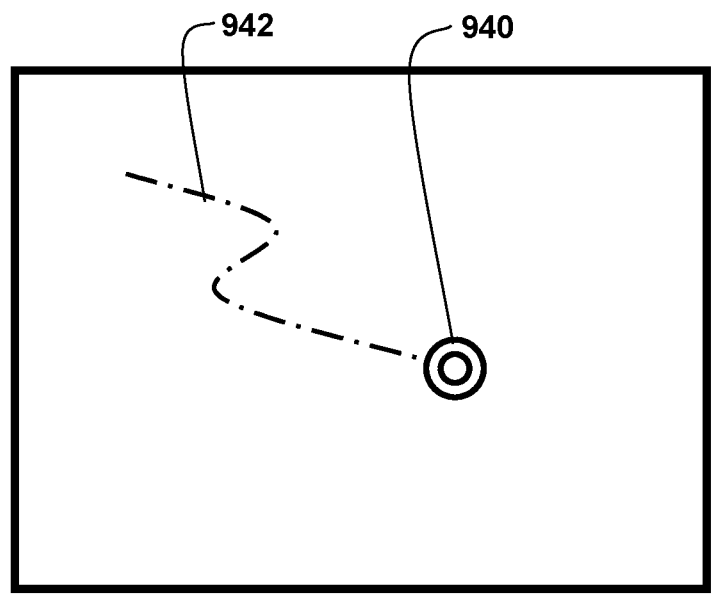
FIG. 23 shows a scene that can be used for scan path tracking.

FIG. 21, FIG. 22, and FIG. 23 illustrate other AR/VR/synthetic 3D display scenes that can be used for ocular performance testing such as VOR, DVA, visual pursuit, and/or fixation ability testing. These scenes can include a test environment comprising natural background features combined with a visual element or target whose shape, color, size, motion, depth, or other attributes have been selected or added to facilitate testing of vestibulo-ocular performance. FIG. 21 shows an example of a scene which illustrates what this type of ocular performance testing, such as with visual pursuit, DVA and/or VOR might look like. In the example shown in FIG. 21, the static scene can be a tennis court and the moving target is the tennis ball 920. The visual element (e.g., tennis) can remain motionless in the center, surrounded by a static court with 2 players on each side. The individual being tested would rotate his/her head in the horizontal and vertical plane while focusing on the visual element. Alternatively, as the person focuses on the static visual element in front of the player on one side of the court, it can suddenly become dimmed and re-appear on the other side of the court. The individual being tested is required to rotate the head each time the visual element reappears. This action can occur in a back and forth manner until the measurement is complete. For more complex testing, the surrounding courtside scene can be filled with fans who are in motion. As another example, if the VOR is being tested on a basketball player, the dynamic background features may be a basketball court surrounded by fans, who are yelling and moving and the visual element (e.g., basketball) may suddenly appear in the hands of a player on one side, then dimmed or removed, and then alternatively appear in the hands of another player on the other side, requiring the individual being tested to move the head in a horizontal manner. Visual pursuit can also be virtually measured using the basketball as the visual element to be tracked as it is in motion from player to player and being thrown upwards to the basketball hoop. This can be a more realistic method of assessing ocular performance with VOR and visual pursuit measurement. DVA measurement can also be performed with dynamic changes of the target or visual element of interest, requiring the person to identify characteristics of the element while it is in motion and the person is in motion and comparing this to the SVA prior to the onset of the DVA test. FIG. 22 shows letters that could be superimposed onto the moving element (such as the tennis ball in FIG. 21) to test DVA. The target visual element 920 in FIGS. 21, 930 and 932 in FIG. 22, or 940 in FIG. 23 could move in different trajectories, in different depths, the letters could be of different sizes, and the ball could move at different speeds and accelerations to provide a meaningful test as shown by comparing visual element 930 with visual element 932. The targets can be static or rapidly moving is a specific plane or scan path for (such as watching a tennis ball move across the court or with tracking tests that have a rotating target visual element) depending on the ocular parameter being tested.

DVA testing could be performed with lettered optotypes and as the head rotates back and forth, the letters can rotate in position. Alternatively, numbers can be used as well as other familiar images of objects. The images can also be native or natural to the background environment displayed. As the head rotates back and forth, the target or visual element is more difficult to visualize. If there is a VOR abnormality, for example the eyes will not be able to focus on the target or visual element of interest and will subsequently have less fixation and more errors in identifying a visual element. Measurement can also be performed with the visual element stationary and the head in motion or both the visual element and head in motion, which would be more realistic with everyday experiences. Static visual testing (SVT) can be performed to obtain a normal visual test. The visual acuity can be obtained, while the head and the visual element, or optotype being displayed are both motionless. Similar to a standard eye exam, an AR/VR platform can enable a person's static visual acuity (SVA), a component of DVA testing, by asking a person to identify a multitude of images or optotypes (letters, symbols, characters, figures of different sizes, shapes, orientation) on the visual screen.

Visual pursuit testing can be performed with similar targets or visual elements of interest as have been described previously. Smooth pursuit testing has traditionally been performed with the head motionless and the eyes following a moving light or finger moving across a visual field. FIG. 23 shows a scene that can be used for scan path tracking in a virtual or augmented environment. An enhanced target visual element 940, can be sent across the scene along a specific path 942, while the measured eye movement follows the visual element. The path of these visual images or elements can assume any pattern, such as a zigzag, a saw toothed, or a square wave, or have a scan path that is snake-like, curved, circular, sinusoidal or rotational to provide a realistic and natural method of assessment of visual pursuit.

Figure 24:
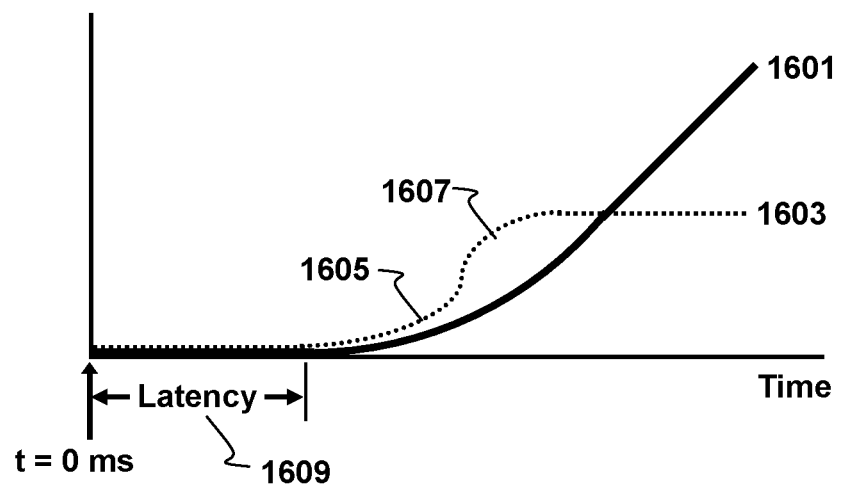
FIG. 24 shows the relationship between target movement, eye position, eye velocity, and eye acceleration for smooth pursuit.

FIG. 24 shows the relationship between target movement, eye position 1601, eye velocity 1603, and eye acceleration for smooth pursuit. The time when the target is moved is identified as t=0 ms. The eye position 1601, and eye velocity 1603, can then be tracked as a function of time. Latency 1609, is the delay from the time the target moves to the time the eye starts to move. Then the eye velocity 1603, will first accelerate 1605, and decelerate 1607, until the eye velocity 1603, matches the target velocity.

Figure 25A:
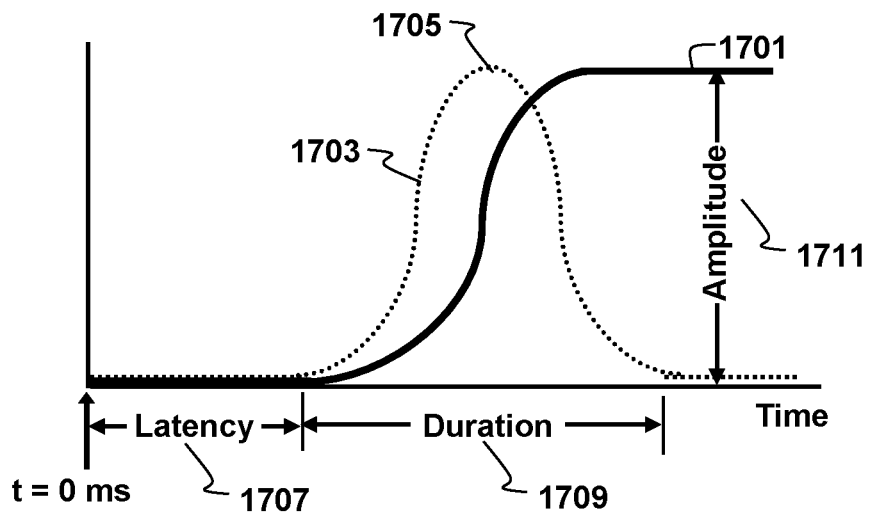
FIG. 25A shows the relationship between target movement, eye position, and eye velocity for a saccade.
Figure 25B:
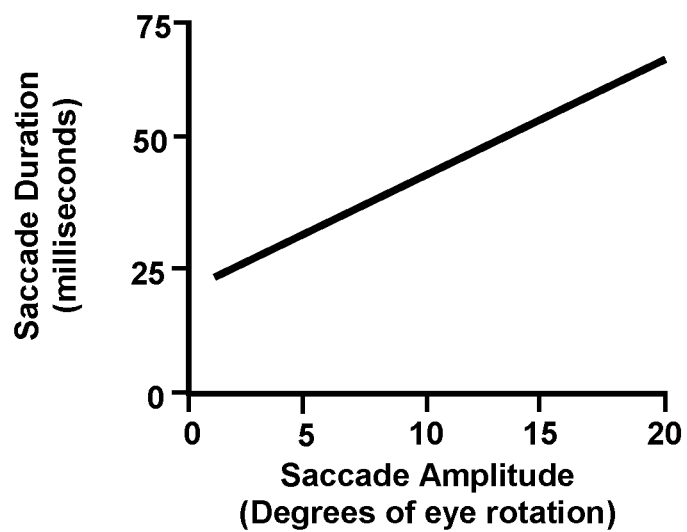
FIG. 25B shows the typical relationship between saccade amplitude and saccade duration.

FIG. 25A shows the relationship between target movement, eye position 1701, and eye velocity 1703, for a saccade. The time when the target is moved is identified as t=0 ms. The eye position 1701, and eye velocity 1703, can then be tracked as a function of time. Latency 1707, is the delay from the time the target moves to the time the onset of a saccade. As shown, the saccade eye velocity 1703, increases, reaches a peak velocity 1705, and then returns to zero. The length of time from the start to the end of this velocity curve is called the saccade duration 1709. The saccade eye position 1701, changes during this duration 1709 to reach a new position that differs from the initial eye position by a distance that can be defined as a saccade amplitude 1711. FIG. 25B shows the typical relationship between saccade amplitude and saccade duration.

Note that any of the testing described for any of these embodiments can be done with static targets or visual elements being viewed, or with dynamic targets or elements. The images or elements viewed may be familiar objects, such as balls, or objects more familiar to one's occupation. The visual target or visual elements may be displayed in a manner that is native or natural to the background.

Figure 26:
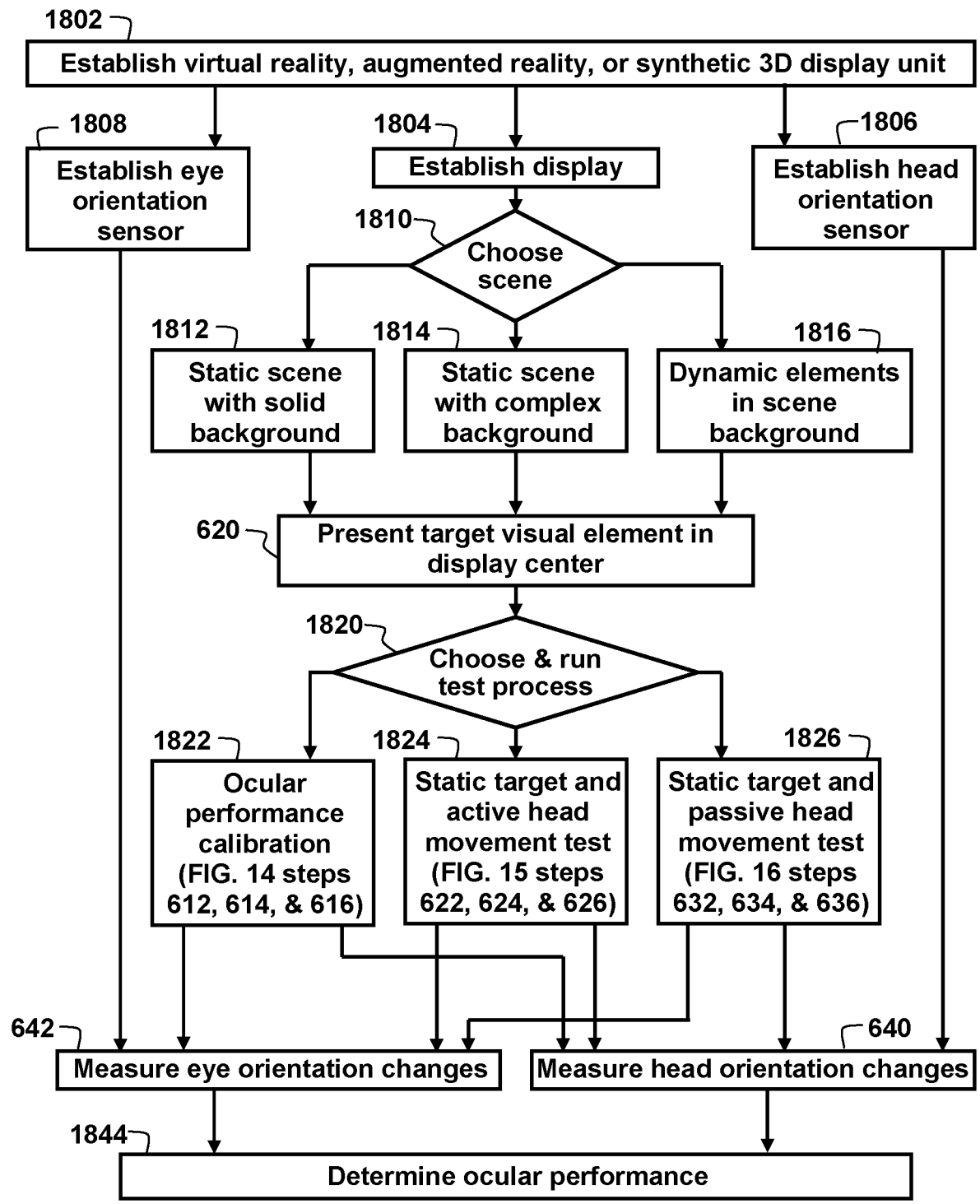
FIG. 26 shows a generalized method for ocular testing using virtual reality, augmented reality, or a synthetic 3-dimensional scene on a display.

FIG. 26 provides a more generalized embodiment of the system and method that was presented in FIG. 14, FIG. 15, and FIG. 16. Referring to FIG. 26, the head-worn virtual reality or augmented reality unit that was shown at 602, in FIG. 14, FIG. 15, and FIG. 16, can more generally also be a synthetic computer-generated 3D display unit and it does not necessarily need to be head-worn. Thus, it could be a VR/AR, or synthetic 3D display unit, as shown at 1802 in FIG. 26. The eye tracking video camera on the unit that was shown at 608, in FIG. 14, FIG. 15, and FIG. 16 can more generally be an eye orientation sensor and it does not need to be mounted as part of the unit. Thus, it could be simply an eye orientation sensor, as shown at 1808. Similarly, the display 604, and head orientation sensor 606, that were shown in FIG. 14, FIG. 15, and FIG. 16 do not necessarily need to be on the unit. They could be located somewhere else as shown at 1804, and 1806, in FIG. 26. As shown in FIG. 26, the process can further include the step of choosing a scene 1810, and the choices of scenes can comprise a static scene with a solid background 1812, a static scene with a complex background 1814, and/or scene with dynamic (i.e., moving) elements in the background 1816. The process shown in FIG. 26 includes the step of presenting a target visual element in the display center 610 and 620, just like the processes shown in FIG. 14, FIG. 15, and FIG. 16.

Further referring to FIG. 26, the method can comprise the step of choosing which ocular test to run on a subject as shown at 1820, and the choices can include ocular performance calibration 1822, static target and active head movement testing 1824, and/or static target and passive head movement testing 1826. Each of these three test processes (1822, 1824, and 1826) involves measuring eye orientation changes 642 and head orientation changes 640, just like the processes shown in FIG. 14, FIG. 15, and FIG. 16. The output of the process illustrated in FIG. 26 can be broaded (e.g., compared to FIG. 14, FIG. 15, and FIG. 16) and can comprise any ocular performance parameter discussed herein. These ocular performance parameters can include any of the following parameters that have been discussed in other parts of this disclosure, including but not limited to:

(a) vestibulo-ocular reflex;
(b) pupillometry;
(c) saccades (overt and covert);
(d) visual pursuit tracking;
(e) vergence (convergence and divergence)
(f) eyelid closure;
(g) dynamic visual acuity;
(h) dynamic visual stability;
(i) retinal image stability;
(j) foveal fixation stability;
(k) focused position of the eyes;
(l) visual fixation of the eyes at any given moment and
(m) nystagmus In an alternate embodiment to the configuration shown in step 1824 in FIG. 26, the visual target of interest can be dynamic and the head movement can also be dynamically moving in the same direction as the visual target movement. The process is repeated as many times as needed. This test can be conducted in the vertical, horizontal or any other direction.

Figure 27:
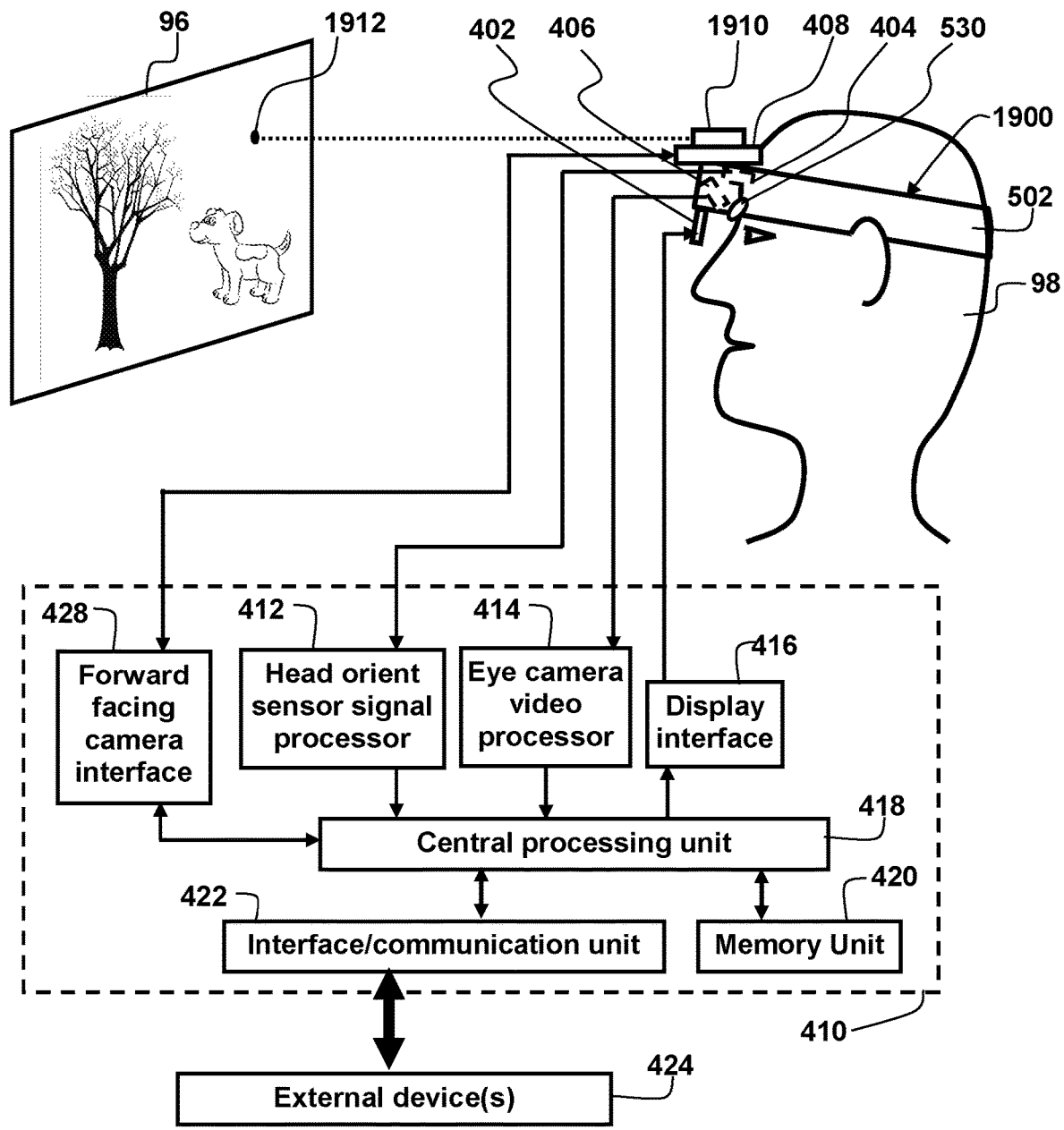
FIG. 27 shows an embodiment similar to that shown in FIG. 1 and FIG. 2, that further comprises a forward-facing camera and a light beam projector.

FIG. 27 shows an augmented reality system at 1900. The augmented reality system 1900 is similar to the embodiments described with reference to FIG. 8, FIG. 11, and FIG. 13A. The embodiment shown in FIG. 27 uses a head band 502 as the structure for head attachment and has many other components similar to the systems described in FIG. 8, FIG. 11, and FIG. 13 with the same numbers in FIG. 27 referring to the same elements, features, or attributes. The augmented reality system 1900 shown in FIG. 27 can be used for ocular performance tests as described in other parts of this document. FIG. 27 also shows a scene 96 that is visible to the user 98. The scene example 96 shows a tree and a dog. The scene 96 can be blank. The scene 96 could be comprised exclusively of static images, such as the tree. The scene 96 could include dynamic (i.e., moving) images, such as the dog.

In addition to all of the items described with regard to FIG. 8, FIG. 11, and FIG. 13, the embodiment of the augmented reality system 1900 shown in FIG. 27 further comprises a light beam projector, shown at 1910, and a forward-facing camera, shown at 408, responsive to eye sensors to measure various ocular parameters. The light beam projector 1910, can be a laser pointer or any other source of a light that can be projected from the head-worn device into the user's field of view, as depicted by the scene 96. The projected light can produce a spot or shape in the user's field of view that can serve as a reference point, a projected object that the user can focus on, as shown at 1912. The reference point or projected object generated by the light beam projector 1912, can be used as a target that the user is asked to follow or focus on as part of an ocular performance test. This reference point or projected object 1912, can be in addition to any information presented by the AR display 402, (also called a see-through display), or it can substitute for one or more of the functions of the AR display 402. For clarity, no connection has been shown between the light beam projector 1910, and the electronic module 410. However, it should be clear to anyone who understands the art that the light beam projector 1910 could be responsive to communication from the electronic module 410. Signals from the electronic module could travel to the light beam projector via a wired or a wireless connection. Such signals could control light intensity, size, shape, color, location, depth, and motion of the object 1912, generated by the light beam projector 1910, or any other parameter of the object capable of being understood by anyone skilled in the art.

Regarding the forward-facing camera, shown at 408 in FIG. 9, FIG. 11, FIG. 12A, and FIG. 27, it should be noted that this forward-facing camera 480 can be configured to record an image of what the user is seeing. In the embodiments discussed herein, the forward-facing camera 408, can be configured to determine, measure and log where the eyes of an individual, such as an athlete or military person, are looking during their play, occupational or military activities. This can be used to measure the duration of time an individual is visually focused on an object or target of interest. For example, this can measure if an athlete or military person can see an opponent or parts of an opponent (such as the hand or helmet) more quickly in time than others and how long the individual maintains focus on the visual object during the play or activity. This can be correlated with the eye tracking video camera 406, for measurement of reaction times. Individuals with highly focused ability on the object of interest can more accurately anticipate and more precisely predict the movements of their opponents. This data can be used in training and/or the selection process of individuals prior to performing the activities needed.

Further referring to FIG. 9, FIG. 11, FIG. 12A, FIG. 27, and other embodiments discussed herein, the forward-facing camera 408, can be configured to adjust its field of view, focal length, or to zoom in or out in response to an eye sensor. The electronic module 410, using the central processing unit 418, could control the forward-facing camera 408. This control of the forward-facing camera 408, could be through wired or wireless electronic signals. The forward-facing camera 408, could transmit video information to the electronic module 410, and this video information could analog or digital information and could be transmitted through a wired or a wireless connection. Any other component in the augmented reality system shown at 1900, could also be controlled through the forward-facing camera 408. The information collected and/or recorded by the forward-facing camera 408, can be responsive to the eye sensors 406, to measure ocular performance parameters. For VOR measurement, head rotation information would be measured using the head orientation sensor 404. The information collected and/or recorded by the forward-facing camera 408, could also be used, in conjunction with other information collected by the augmented reality system 1900 in FIG. 27, for capturing visual images of the user's surroundings, or activate a photo or video feature of the synthetic 3-D scene and determine the intended focal point of the use. As discussed previously, this determined intended focal point can be measured and correlated with the fixation accuracy of the eye tracking sensors. The user can also perform a predetermined action with the his/her eye(s) by focusing on a specific image or orienting the eye in a specific manner as an input control. Data collected can be uploaded and transmitted to a remote or external device.

Figure 28:
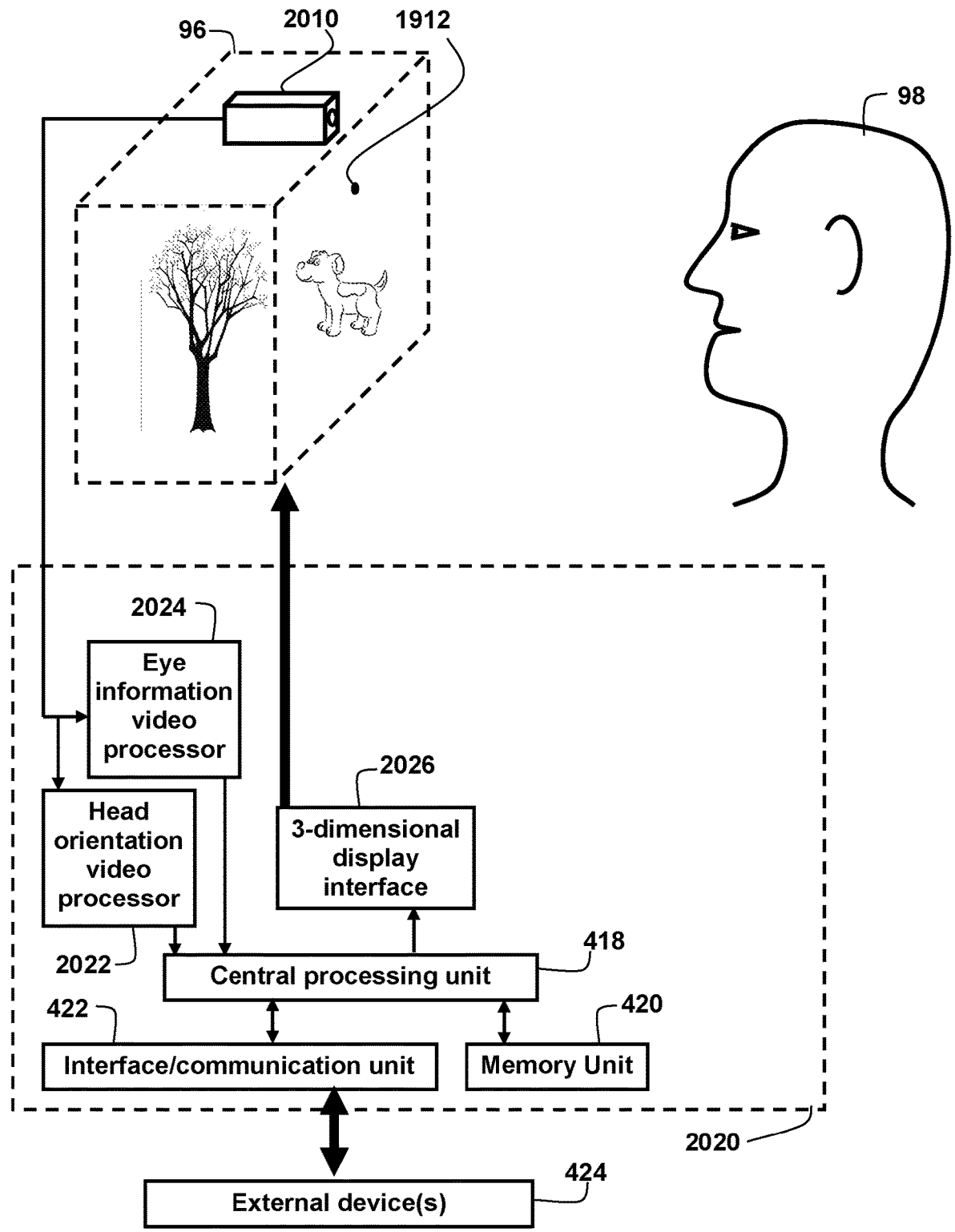
FIG. 28 shows an embodiment of a system similar to the ones described previously that requires no head-worn components.

FIG. 28 shows an embodiment of a system and method using AR/VR/3D simulation that is similar to the embodiments previously. In the embodiment shown in FIG. 28, the functions illustrated and described previously are performed without a head-worn device. In the embodiment shown in FIG. 28, the scene 96, is produced using an electronic module 2020, that comprises a 3-dimensional display interface (or device) 2026, for presenting the information. This 3D display interface/device 2026, could use any 3D display technology capable of being understood by anyone skilled in the art, including any of the 3D display technologies discussed in other parts of this document. Holography is one example of such a 3D display technology. Due to the realism available through the use of a 3D display device/technology, the person (or subject, or user), feels that they are immersed in the scene 96. Non-user-worn eye tracking can be accomplished using any of the technologies discussed in other parts of this document. The use of a video camera located above the scene 2010, is one example of such an eye tracking and head tracking technology. Non-user-worn head tracking could be accomplished using any of the technologies discussed in other parts of this document. The use of a video camera located above the scene 2010, is one example of such a head tracking technology. Note that in the embodiment shown in FIG. 28, the same video camera 2010, is used for both eye tracking and head tracking. This could also be accomplished using two separate cameras and any combination of any of the technologies discussed in this document. The video camera(s) 2010, could be connected to an eye orientation video processor 2024, and a head orientation video processor 2022, both of which can be connected to a central processing unit 418, in the electronic module 2020. The visual object 1912, that can serve as a target, as described with reference to FIG. 27 can be generated as part of the scene 96. This target 1912, could be stationary (static) or it could be dynamic (moving). The electronic module 2020, through the display interface 2026, can control the target 1912. The electronic module 2020, comprising a central processing unit 418 and a memory unit 420, can also be used to record display information, head orientation information, and eye information to keep a record of a test for subsequent analysis. The system shown in FIG. 28 can further comprise an interface and/or communication unit 422, which can be configured to communicate with an external device or remote devices 424. Any ocular performance measurements with the system shown in FIG. 28 can be done using any of the methods described in other parts of this document.

Further referring to FIG. 28, ocular performance can be measured using static or dynamic images projected in the display scene 96, either with the head motionless or moving. The 3-dimensional scene can comprise a solid unobtrusive background or a background resembling typical natural activity. Any of the visual targets or visual elements previously discussed can be applied to this configuration. The 3-dimensional background scene, provided by the 3D display, can be limited or fully immersive with images that extend around 360-degrees around the subject as well as above the subject in a full hemispherical or spherical configuration that surrounds the subject. viewed images.

In one embodiment, the 3D image is generated using a hologram. The user has in his visual field a holographic scene, which as an example may resemble basketball court, occupied by other players and the stands are filled with fans. The holographic scene can be varied having static or dynamic features. The user's eye movements can be measured by the remote eye sensors 2010, while visually immersed within the scene. VOR testing, pursuit tracking and other ocular parameter measurements discussed herein can be performed while seemingly involved in the play activity. This type of measurement can also be performed in other environments more familiar to the user (e.g., a football field, tennis court, military activity). Alternatively, in another similar embodiment, the user can be wearing a device comprised of an eye tracker, head tracker, forward-facing camera and laser projector, while the human ocular performance is measured. A synthetic 3D display system can be used using holographic imaging or a volumetric display. In this embodiment, a light beam projector or a laser hologram can be used to project a target of interest or visual element into the 3-dimensional display scene. This target of interest can be an image of a white dot, or other enhanced visual target upon which the user can focus. The ocular performance can be measured similar to that previously described in FIGS. 14, 15, 16, and 26. The measured visual element being viewed can be projected from the laser projector while the user is seemingly immersed in the scene of the holographic imaging or a volumetric display. A forward-facing camera can be oriented to capture visual images of the user's surroundings, or activate a photo or video feature of the synthetic 3-D scene and determine the intended focal point of the use. This determined intended focal point can be measured and correlated with the fixation accuracy of the eye tracking sensors. The user can also perform a predetermined action with the his/her eye(s) by focusing on a specific image or orienting the eye in a specific manner as an input control.

Embodiments of the invention discussed herein, when using a VR/AR/mixed (AR and VR)/holographic/synthetic 3D systems can provide more dynamic immersive methods to detect and measure concussions/traumatic brain injury, evaluate individual ocular performance and predict athletic or occupation performance before play or other occupational activities based on the measurement of ocular parameters previously discussed, experience new immersive training opportunities and to measure cognition, attentiveness and fatigue using multi-dimensional methods.

Embodiments of the invention(s) disclosed herein can utilize a faceguard, face shield, visor or accessory head-worn attached device and with forward facing camera and method to detect and manage concussions, traumatic brain injury in athletes and other subjects such as military personnel. In these embodiments, of the faceguard, face shield, visor or accessory head-worn device, head orientation measurements and ocular parameter measurements are utilized including but not limited to vestibulo-ocular reflex, pupillometry, saccades, vergence, dynamic visual acuity, eye-lid closure, focused position of the eyes, kinetic visual acuity, virtual retinal stability, retinal image stability, foveal fixation stability and nystagmus.

Embodiments of the invention can incorporate other impact mitigation elements and sensing elements/transducers for detecting any abnormal physiological or biochemical properties of the user.

In the embodiments disclosed herein, the forward-facing camera can be responsive to the eye sensors to measure the ocular performance described. It can visualize "world" objects in motion and then correlate these visual objects seen by the user with user eye movements.

Measuring the visual object, the user is focusing upon, can be used to determine a prediction component of the user eye motion based on the visual target motion (e.g., Motion Tracking with Predictive Index Factor).

Sensors

Embodiments of the invention(s) disclosed herein utilize sensors. These sensors are also referred to as sensing elements/transducers. In embodiments disclosed herein, these sensors can be used to detect and measure specific physical phenomena such as ocular performance and head orientation. There can also be sensors that measure physiologic, biochemical, and biometric values. The helmet, faceguard, face shield, or other device can incorporate sensors or sensing elements/transducers associated with the impact layers, material or padding specifically placed or positioned to measure various properties of the impact mitigation system. In one embodiment, sensing elements/transducers are located in the impact mitigation layer to adjust the rotational and linear impact mitigation system to be centered circumferentially, as seen in the horizontal plane, over the foramen magnum and pivot point at the upper spinal cord and brainstem junction to reduce rotational acceleration with tangential blows to the head. These sensing elements/transducers can keep the configuration of more padding posteriorly to keep the center of the helmet, when viewed horizontally proximate to the foramen magnum. Sensing elements (also referred to as transducers) can deploy in response to input. One example would be a pneumatic impact mitigating element (e.g., pneumatic/inflation bag, cushion, pad or device) from the external shell, other layer, an adjacent material or nearby worn padding, which can be altered, or changed in its characteristics prior to imminent impact to provide an additional air protection system to the head and or neck. The sensing elements, sensors, or transducers can exhibit artificial intelligence in response to imminent blow information detected and the measured threshold values to determine the abnormal value necessary to elicit a response in order to maintain health of the user. The sensing elements, sensors, or transducers can detect and respond to an imminent occurrence when two or more bodies come together or violent blows to head by making changes or adjustments in the impact material, by increasing the padding, altering the shape of the elastomeric properties or altering the characteristics of the impact reduction material within the helmet, to mitigate the force exerted upon the head. These sensing elements/transducers can be self-altering, self-adjust, change shape or characteristics after an impact and resume pre-blow/state. The sensing elements, sensors, or transducers can also allow observers to remotely check the status any of the sensing elements/transducers described and can change the parameters of the sensing element/transducer measurement or sensitivity if needed. Sensing elements/transducers on the external shell can record information of how many times a head receives hits before specific thresholds are reached indicating an abnormality. Artificially intelligent sensing elements/transducers can also change impact mitigation material characteristic shape and resistance, depending on the power of blow detected and the location of the blow to the head, consistent with an ideal force displacement ratio.

These sensing elements/transducers can be pressure sensitive, ultrasonic, mechanic, electrical, electromagnetic, responsive to haptic, graphene, PVDF (polyvinylidene fluoride sensing, fluid-based sensing elements/transducers, microelectromechanical systems (MEMS)-based on accelerometers, silicon-based solid-state accelerometers, binary sensing elements of plastic housing and working fluids to detect instantaneous acceleration (impact).

In another helmet embodiment, to enhance the safety of the wearer, following occurrences of violent blows to the head the measured physical aspects of the blow data can be displayed to an observer and/or provide a local, adjacent or remote response, alert or warning. This response to an abnormal blow value can be in the form of an optically perceptible response, such as photofluoresence, or can be a haptic, vibratory, or an acoustic response either to the user and/or the device of the observer. For example, the helmet or specific portion of the helmet may change colors, emit a light, display or generate another signal response when a user receives a critical blow to the head, exhibits abnormal oculomotor findings, reaches an abnormal physiological or biochemical pre-determined value. In another embodiment, adjacent clothing may change color when the abnormal values have been reached. Where desired, the sensing element/transducer data can be used to activate an associated intervention system, human or automated, to prevent injury to the user. As an example, flexible sensing elements/transducers within the helmet layers can detect a mechanical stimulus (e.g., compressions or blows) and emit mechanoluminescence or triboluminescence (e.g., light emissions) when a preset abnormally harmful impact value is reached, which can be visualized by observers. This visual response to a violent blow to the head which has exceeded a specific preset threshold value, or abnormal physiologic or biochemical value can also include other responses including but not limited to: flexible terahertz imagers with tunable multi-arrayed carbon nanotube materials or other photonic devices. This can include Internet-of-Things (e) sensing element/transducer applications, which can connect the sensing system of the device or components of the device to the internet.

In another embodiment sensing elements/transducers located on the face guard, faceshield, visor or accessory device attached to the system discussed can detect where the eyes are looking and focused, which can be correlated with a forward-facing camera and can log the data statistics on eye movements and point of fixation of the eyes and any given time. These sensing elements/transducers can measure human ocular performance include the vestibulo-ocular reflex, saccades, visual pursuit tracking, pupillometry, vergence, convergence, divergence, eye-lid closure, dynamic visual acuity, kinetic visual acuity, retinal image stability, foveal fixation stability, focused position of the eyes or visual fixation at any given moment and nystagmus. Data from helmet faceguard, faceshield or visor can be transmitted to a remote device such as smart watch or another smart device.

Embodiments of this invention can also use sensing elements/transducers on the innermost layer, adjacent to the skull to more accurately measure information regarding violent blows to the head (such as linear and rotational acceleration data).

In another embodiment of the inventions discussed herein, sensors or sensing elements/transducers, used to detect and measure physiologic or biochemical properties of the user, are anatomically positioned for the physiologic or biochemical parameter designed and placed adjacent to the skin. These sensors or sensing elements/transducers can detect abnormal physiologic measures not limited to but including: arterial pressure exerted by the blood upon the walls of the blood vessel, and varies with the muscular efficiency of the heart, blood volume, viscosity, age, health of the individual, and the state of the vascular wall, including hypotension (defined as systolic arterial pressure less than 100 mm of mercury), hypertension (defined as systolic arterial pressure 140 mm of mercury or greater); thermal changes including hypothermia (below 95 degrees) and hyperthermia or hyperpyrexia (significantly above 98.6 F), changes in cardiac activity including bradycardia (below 60 bpm), and tachycardia (above 100 bpm at rest), arrythmia (irregular rhythm), atrial fibrillation, atrial flutter, cardiac arrest, rate of inhalation and expiration as well as the ocular parameters discussed previously. As noted above, the sensing elements/transducers over the head would be positioned be over the temporalis region, just anterior and superior to the tragus and pinna to measure the superficial temporal systolic arterial pressure exerted by the blood upon the walls of the blood vessel and the abnormal changes in cardiac activity. Sensing elements/transducers for measuring abnormal thermal changes of wearer would be located over the temporal skin, as measurements are closer to true (core) body thermal value.

In another embodiment, the sensing elements/transducers can also detect and measure any abnormal changes in cranial, motor or sensory function, mental status, nervous system status, non-focal and focal neurologic changes, conscious intellectual activity, and specifically any abnormal measurement of cerebration, abnormal waveform frequency of the cerebral cortex, spike analysis, electrophysiologic measurement of cerebral activity with sensing elements/transducers in contact with the scalp or using evoked Potentials (EP) to detect and measure topographic cerebral mapping. Specifically, abnormal waveform patterns associated with concussions can be detected and measured including: a decrease in alpha and beta relative power & mean frequencies, increase in temporal lobe slowing (Delta, Theta or Alpha); significant Alpha Asymmetries; significant coherence and/or phase issues either hypo or hyper with phase lag usually being slower; temporal lobe or all frontal lobe or front/back issues; excessive Delta and Theta (associated with recent injury); more power in faster Alpha bands, 10-11 Hz (consistent with an older injury) or evidence of epilepsy. The sensing elements/transducers for measurement also requires strategic placement and accuracy is dependent on the number of sensing elements. Conventionally 21 electrodes may be used over specific scalp locations, and dense array with 32-64 miniature sensors can provide a more accurate map of scalp voltage distribution than the conventional array.

In another embodiment, the sensing elements/transducers can detect abnormal biochemical measures not limited to but including simple monosaccharides (sugar) or dextrose, metabolites, proteins, electrolyte abnormalities including detection and measurement of hypokalemia (below 3.5 mM) and hyperkalemia (above 5.5 mmol/L), hyponatremia (below 135 mmol/L), hypernatremia (above 145 mmol/L), acidosis, alkalosis, osmolality, cortisol level, and evidence of depletion of body fluids/hypohydration.

Sensing elements/transducers can detect and measure chloride, including hyperchloremia (above 110 mEq/L), hypochloremia (below 98 mEq/L), amount of oxygen bound to hemoglobin in the blood, expressed as a percentage of the maximal binding capacity, including hypoxia, hypoxemia (e.g., low partial pressure of oxygen in the arterial blood with less than 90 percent), hyperventilation/tachypnea, which can result in hypocapnia; hypoventilation, hypopnea, bradypnea; hypocapnia (less than 35 mHg for partial CO2 pressure); hypercapnia (blood CO2 level over 45 mmHg) or ventilatory failure. The sensing elements/transducers can also detect volatile organic compounds through skin sensing elements/transducers or different gases/organic molecules as a biomarker for human detection. Sensing elements/transducers require specific placement adjacent to or in contact with sweat, near arteries beneath the skin, depending on what is being measured.

Among many bodily fluids, sweat provides a significant amount of information about a person's health status and is readily accessible, making it suitable for wearable, noninvasive biosensing. Sweat contains important electrolytes, metabolites, amino acids, proteins and hormones, which allows monitoring of metabolic diseases, physiological conditions, or a person's intoxication level. Stress plays an important role in the overall health of a person, when under stress, the adrenal gland releases cortisol and adrenaline into the bloodstream. Cortisol can be detected in the sweat. Increased levels of cortisol have a detrimental effect on the regulation of physiological processes such as blood pressure glucose levels, and carbohydrate metabolism.

As noted previously, sensors or sensing elements/transducers, within the helmet, are strategically placed, based on the position of human anatomical structures and the parameter they were designed to detect and measure. As an example, when measuring the pulse rate or blood pressure the sensing elements/transducer are not positioned randomly but placed over a major artery (such as superficial temporal or occipital artery). When obtain information from bodily fluids the sensing elements/transducers are placed where there a higher concentration of eccrine sweat glands (e.g., the major sweat glands, which are sometimes called merocrine glands which open directly onto the skin surface), such as on the forehead. Eccrine glands secrete a sterile, dilute electrolyte solution with primary components of bicarbonate, potassium, and sodium chloride, glucose, pyruvate, lactate, cytokines, hormones such as cortisol and immunoglobulins. It has the same components as plasma but in a more dilute concentration.

In another embodiment, this sensing element/transducer can be specifically placed on the buccal side of a dental structure, in contact with buccal mucosa, as it is a source of bodily fluids) for: chemical/biochemical analysis (e.g., Sodium/potassium/glucose/cortisol/proteins/electrolytes/ hydration status) as well as identity information of an individual. These sensing elements/transducers can communicate with other sensors within the helmet system in such a way that if any abnormal physiologic or biochemical parameter is detected, a transdermal drug can be released to permeate across the skin to treat the abnormal condition.

Other sensing elements/transducers in the helmet system can also communicate with other sensing elements/transducers in such a way that if any abnormal physiologic or biochemical parameter is detected, a transdermal drug can be released to permeate across the skin to treat the abnormal condition.

In another embodiment, these sensing elements/transducers can be implantable for measuring physiologic, chemical or biochemical abnormalities and abnormal parameters can communicate with other worn sensor elements and data can be transmitted remotely. Any of the sensors or sensing elements/transducers listed here, or others capable of being understood by anyone skilled in the art may also provide a user with information about his or her own biometric data changes.

Eye Tracking

To measure some specific eye responses (such as VOR, DVS, DVA or other ocular performance measures), both eye tracking and head tracking measurements are required. Eye tracking is the process of measuring either the point of gaze (where one is looking) or the motion of an eye relative to the head position. An eye tracker is a device for measuring eye positions and eye movement. Eye tracking and/or measurement can be done in many ways, examples of which include:

(a) using a face guard with eye sensors and a head orientation sensor and having the user look at a projected image in a natural environment;
(b) using a face shield or visor or using an accessory device attached to a face guard, face shield/visor, or helmet and having the user look through the AR or mixed (AR and VR) device that has eye and head sensing elements/transducers are components with the device;
(c) using a VR head worn device in which the user is viewing a display while eye and head sensors measure the user's response to the displayed image;
(d) using a device such as a contact lens that is in contact with the eye;
(e) using a head worn device;
(f) using a remote system;
(g) measuring head and eye movement with sensors attached to another part of the body, such as a handheld device or a smart watch; or
(h) using a smart phone, which is hand held or mounted to the head and measuring ocular parameters (e.g., VOR, visual pursuit, pupillometry, vergence, etc.) with applications and sensors within the smart device.

The eye tracking and/or measurement can also be done:

(a) in a non-contact fashion with the use of a light source (invisible light, such as with the use of an infra-red camera or light, or visible light);
(b) by using a video camera or other sensor system designed to visually capture and record the eye movement activity;
(c) with a marker or sensor on a contact lens; and/or
(d) with a magnetic system such as one using magnetized contacts and an external detector.

If one or more video cameras are to be used for eye tracking, it is desirable to have a sampling rate at least 60 frames per second (60 Hz) and preferably at least 60-120 Hz. Many video-based eye trackers have sample rate of at least 30, 60, 120, 250, 350 or even 1000/1250 Hz. In embodiments of the present invention, eye tracking might typically use a sampling rate minimally of 60 Hz, but more typically at 120 Hz-350 Hz. These higher sampling rates may be needed in order to capture fixation of eye movements or correctly measure other saccade dynamics or capture the detail of the very rapid eye movement during reading, or during neurological evaluations, such as with concussions.

In embodiments of the present invention, the video camera in a smart phone or tablet device could be used as an eye tracker. Since the eyes are not located at the center of head rotation, any rotation of the head requires translation of the eye relative to visual targets. For targets at optical infinity, this translation does not require any compensatory movement. For near targets this translation becomes significant and compensatory eye movements are required for stable gaze and at close target distances. One must also compensate when measuring VOR and the compensation requires knowing the distance between the center of rotation and the visual target. The relative location of the center of rotation of the eye with respect to the head mounted head tracker receiver varies for each subject because of anatomical considerations.

In embodiments of the invention, a light source can be used to illuminate the eye(s) and aid in eye tracking and/or measurement. The light source can be directed toward the eye or eyes and a camera tracks the reflection of the light source and visible ocular features such as the pupil features and/or cornea surface reflection(s). The information can then be analyzed to extract eye rotation and ultimately the direction of gaze from changes in reflections. Additional information such as blink frequency and changes in pupil diameter can also be detected by the eye tracker. The aggregated data can be stored and written to a file that is compatible with eye-tracking analysis software. Graphics can be generated to visualize such findings. Beyond the analysis of visual attention, stored eye data can be examined to measure the cognitive state or other information.

A camera can be used as a sensor for detecting light in high resolution. When tracking and/or measuring the eye activity or eye movement, such as the VOR, an IR or video camera may be used and can be comprised of a single camera system or a multiple camera system. The camera can be located on the framework of the head worn device or within the lens material, or in the contacts being worn. If using a hand-held device, such as a smart phone, the video camera can be located remotely in the device being held, mounted or worn elsewhere on the body. The camera control unit can be activated by such options as: an external wireless signal, a touch unit, rapid head movement or voice activation. The control unit can also be timer actuated, triggered by an eye blink for a defined period of time, or by placing the device on the head (e.g., putting on the head-worn unit). The eye tracking system can be mounted on a head worn device, on eyeglasses framework, or partially within the lens of eyeglass or contact lens, on in a hand held mobile smart device, such as a smart phone, smart pad, or limb worn computer system.

The eye tracking and/or measuring system may include hardware such as an infrared camera and at least one infrared light source, a video tracking system and recorder. The infrared camera may be utilized by the eye tracking system to capture images of an eye of the wearer. The video images obtained by the infrared camera regarding the position of the eye of the wearer may help determine where the wearer may be looking within a field of view of the head mounted display used in the system. The infrared camera may include a visible light camera with sensing capabilities in the infrared wavelengths. Infrared light or radiation is a longer-wavelength radiation than visible light. It exists just outside of the spectrum of visible light. Heat, or thermal energy, is a common source of infrared light. An infrared camera is a device specially designed to detect and display the sources of this kind of light. A thermal infrared camera converts the heat detected into electrical signals, which are then projected in an image. Many types of night vision cameras are based on infrared light. A human body will always emit heat, and infrared cameras will detect this radiation.

The infrared light source can include one or more infrared light-emitting diodes or infrared laser diodes that may illuminate a viewing location, i.e., an eye of the wearer. Thus, one or both eyes of a wearer of the system may be illuminated by the infrared light source. The infrared light source may be positioned along an optical axis common to the infrared camera, and/or the infrared light source may be positioned elsewhere. The infrared light source may illuminate the viewing location continuously or may be turned on at discrete times.

In embodiments of the invention, the optical system can include components configured to provide images to a viewing location, i.e., an eye of the wearer. The components may include a display pane, a display light source, and optics, such as mirrors or refractive lenses. These components may be optically and/or electrically-coupled/connected to one another and may be configured to provide viewable images at a viewing location. One or two optical systems may be provided in the system. In other words, the head mounted display may allow the wearer to view images in one or both eyes, as provided by one or more optical systems. Also, the optical system(s) may include an opaque display and/or a see-through display connected to the display panel, which may allow a view of the real-world environment while providing superimposed virtual images. The infrared camera or video camera, using visible light, coupled to the eye tracking system may be integrated into the optical system with a data storage and logging recorder.

Video-based eye trackers typically use the corneal reflection (the first Purkinje image) and the center of the pupil as features to track over time. A more sensitive type of eye tracker, the Dual-Purkinje eye tracker uses reflections from the front of the cornea (first Purkinje image) and the back of the lens (fourth Purkinje image) as features to track. A still more sensitive method of tracking is to image features from inside the eye, such as the retinal blood vessels, and follow these features as the eye rotates.

Eye sensors to track reference locations on the surface of one or both eyes to determine gaze-tracking locations, utilizing multiple illumination sources and/or multiple cameras to generate and observe glint/reflections from multiple directions can be used improve the accuracy of gaze tracking. One or more of the illumination sources can be comprised of infrared, near infrared or visible light, such as a micro-LED or micro-OLED projector. Eye sensors can also obtain biometric information. Eye sensors can be used to obtain anatomic structures and features of the eye, movements of the eye and eyelids, responses and reflexes of the eyes and eyelids. Eye tracking data can also be collected using a multi-camera eye gaze tracker, which is based on one-camera gaze estimation algorithm. Using an algorithm, the 3D eyeball position can be estimated by the two corneal surface reflections (or glints) of the IR lights. Each camera can estimate the gaze independently and can allow large head movement. The accuracy of this system is less than 1 degree.

Eye tracking using binocular horizontal and vertical eye position estimates can be derived from the relative positions of multiple corneal reflections and the center of the pupil. By using two eye landmarks (corneal surface reflections and pupil center) whose relative position are invariant under translation, the angular position of the eye independently of lateral motion of the video system relative to the head is able to be estimated. The optical components can be mounted on a helmet, faceguard, face shield, visor, head-worn accessory device, eyeglasses frame or goggles.

In embodiments of the invention, the light source can be infrared, near infrared, and/or visible light, such as LED, can be directed toward one or both eyes. The camera can be used to track the reflection of the light source and visible ocular features such as the pupil features, cornea reflection features, iris registration features, limbus features or retinal data imaging. The collected data from the eye tracking system can be used to measure the movement features of the eyes or eyelids or rotation of the eye, acceleration/velocity of the eye movement, duration of the eyelid closure, rate of the eyelid closure and the direction of gaze. Additional information such as blink frequency and changes in pupil diameter can also be detected by the eye tracker. Aggregated eye tracker data can be written to a file for later analysis. Stored eye tracker data can be used to analyze the visual path across an interface such as a computer screen. In this case, each eye data observation is translated into a set of pixel coordinates. From there, the presence or absence of collected eye data points in different screen areas can be examined. This type of analysis is used to determine which features are seen, when a particular feature captures attention, how quickly the eye moves, what content is overlooked and virtually any other gaze-related data. Eye position is extracted from video images and graphics are often generated to visualize such findings. Search based on an electro-oculogram may be used. When using a video-based eye tracker, the camera can be focused on one or both eyes and used to record eye movement as a viewer looks at some kind of stimulus.

A thin prism can be used between the eye and a camera system, which acts as a light-guide altering the imaging path between the camera and the eye. The use of a thin prism can also provide on-axis illumination. This arrangement can enable an eyeglass like eye tracking device, which captures a frontal (i.e., on-axis) or near frontal image of the eye to have a visually appealing form factor.

In other embodiment multiple prisms can be used which can use a corrective optical element to eliminate any deviation or aberrations in the see-though viewing path, such that a user of the device can comfortably see through the eye-tracker normally. For example, in one of its aspects, the invention may include a wedge prism having only planar surfaces. This prism acts as a light guide to supply illumination light to the eye, as well as providing imaging light to the camera from the illuminated eye. In this embodiment a complementary prism can be arranged with respect to the thin prism such that the two prisms appear to the eye as a plane-parallel plate, or as a weakly powered optic.

In an alternative embodiment, an eye-tracker can use a free-form prism between the eye and a sensor. The freeform prism includes one or more surfaces with optical power, which are used both for imaging of the eye onto the sensor, and for optical aberration control. In certain embodiments, the freeform prism is used in conjunction with, or exclusive of, additional focusing optics such as a camera outside of the prism.

The eye-imaging camera can be mounted within the faceshield or visor material (either in the center of the visual field or off axis of the center of the visual field), on the framework around the faceshield or visor or viewed lens, or attached to the faceshield, visor or viewed lens and can capture the image of the eye through reflection off of the lens. In order to properly capture the eye image through reflection off of lens, there must be sufficient clearance between the user's face and the lens surface to avoid the obstruction of the eye image by user's face or the imaging optics.

Alternatively, the camera can be mounted on the helmet or faceguard and positioned anywhere around the eye (e.g., under, above, or to the sides) or directly positioned in front of the eye, and directly in the visual field.

A beam splitter in a face shield, visor or accessory device can be used, of which an eye is imaged by a camera positioned out of a user's line of sight. A beam splitter is an optical device that separates a beam of light into two or more different beams of light. Beam splitters are available in various forms. These include cubes, pipes and plates. What happens with a beam splitter is that it accepts the input beam and then proceeds to divide the light depending on the specified requirements. The input beam could be polarized or non-polarized light. The most commonly used is the cube beam splitter although the plate beam splitter is typically used to produce lower cost non-polarized beam splitters. These typically provide a 50-50% split ratio. The reflected and transmitted light emerging from the beam splitters are at various angles, which often necessitates external mirrors to redirect the light. Embodiments of the present invention are directed to single prism beam splitters and compound beam splitters formed from combining one or more of the single prism beam splitters. The beam splitters can be configured to produce one or more split beams of light that emerge from the prism at angles other than 90° to one another. The prisms can be configured so that the light propagating through the prisms encounters one or more intermediate planar surfaces at various angles with respect to the path of the light. A certain number of the intermediate planar surfaces can be angled so that the light transmitted along a particular path undergoes total internal reflection (TIR) at these intermediate planar surfaces. A number of other intermediate planar surfaces can be positioned or angled so that the light transmitted along a particular path does not undergo TIR. As a result, one or more beams of light propagating through the prism can be selectively split off to emerge from the prism by selectively disposing fully reflective and partial mirrors on the intermediate planar surfaces where TIR does not take place. The coating layer of a beam splitter can be made in such a way that a percentage of the light entering the beam splitter through one side can be reflected while another percentage is transmitted.

In other embodiments of the present invention, two or more of the single prism beam splitters can be combined to form compound beam splitters that split a single beam of light into three or more different beams of light. A beam splitter can have an optical multi-layer thin film, formed by laminating numerous layers in sequence. The numerous laminated layers can each be comprised of having a different refractive index.

In another embodiment, the eye tracking system can include a camera attached to or incorporated in the faceshield or visor that is positioned in front of the eye of a user. In another embodiment, an array of optical detection elements can be placed directly onto the surface, or within the faceshield, visor or eyeglass-like lens located in front of an eye.

When using an eye-tracking camera, two general types of eye tracking techniques can be used: Bright Pupil and Dark Pupil. The difference between these eye-tracking techniques is based on the location of the illumination source with respect to the optics. If the illumination is coaxial with the optical path, then the eye acts as a retro-reflector as the light reflects off the retina creating a bright pupil effect similar to red eye. If the illumination source is offset from the optical path, then the pupil appears dark because the retro-reflection from the retina is directed away from the camera. Bright Pupil tracking creates greater iris/pupil contrast allowing for more robust eye tracking with all iris pigmentation and greatly reduces interference caused by eyelashes and other obscuring features. It also allows for tracking in lighting conditions ranging from total darkness to very bright. But bright pupil techniques are not effective for tracking outdoors as extraneous IR sources interfere with monitoring.

Embodiments of the eye tracking system can track on the cornea or further in the eye, based on using light reflected by the eye. Whether using an external source or ambient light, some of the techniques for tracking the eye include: limbus tracking, pupil tracking, Purkinje image tracking, corneal and pupil reflection relationship, corneal reflection and eye image using an artificial neural network.

Regarding limbus tracking, the limbus is the boundary between the white sclera and the dark iris of the eye. Because the sclera is (normally) white and the iris is darker, this boundary can easily be optically detected and tracked. The limbus tracking technique is based on the position and shape of the limbus relative to the head. This means that either the head must be held still, or the apparatus must be fixed to the user's head. Due to the occasional covering of the top and bottom of the limbus by the eyelids, it is more helpful for precise horizontal tracking only.

Regarding pupil tracking, this technique is similar to limbus tracking. The difference is that in pupil tracking the smaller boundary between the pupil and the iris is used instead of the boundary between the white sclera and the dark iris. Once again, the apparatus must be held completely still in relation to the head. The advantages of this technique over limbus tracking is that the pupil is far less covered by the eyelids than the limbus, and thus vertical tracking can be accomplished in more cases. Also, the border of the pupil is often sharper than that of the limbus, which yields a higher resolution. The disadvantage pupil tracking is that the difference in contrast is lower between the pupil and iris than between the iris and sclera, thus making border detection more difficult.

Regarding Purkinje image tracking, when light (such as infrared) is shone into the user's eye, several reflections occur on the boundaries of the lens and cornea and sensed by a video camera or eye sensor. These reflections are called Purkinje images. The information is then analyzed to extract eye rotation from changes in reflections. One type of video based eye tracker uses the corneal reflection, also called the glint (the first Purkinje image) and the center of the pupil as features to track over time. A more sensitive type of eye tracker, the dual-Purkinje eye tracker, uses reflections from the front of the cornea (first Purkinje image) and the back of the lens (fourth Purkinje image) as features to track. A more sensitive method of tracking is to image features from the retina, such as retinal blood vessels and follow these retinal features as the eyes move.

Regarding pupil and pupil reflection relationship tracking, eye trackers can combine a camera with an infra-red light source that illuminates the eye with bursts of invisible infra-red light. Some of this infra-red light disappears into the pupil (the dark opening in the center of the iris), and some of it bounces back off the iris (the colored part of the eye), the cornea (the clear part at the front of the eye), the eyelid or the surrounding skin. All these different areas reflect different amounts of infra-red light, which is picked up by the camera. By analyzing the reflections using "a lot of very fancy matrix math" it is then possible to work out where the eye is pointing. Because eyes move in tandem, this only needs to be done for one eye. The technique is able to cope with blinking, head movements, dim light, glasses and contact lenses.

Regarding the use of artificial neural networks (ANNs) for computation, this is of the more recently developed techniques. The raw material for eye-gaze tracking is still a digitized video image of the user, but this technique is based on a more wide-angled image of the user, so that the entire head is in the field of view of the camera. A stationary light is placed in front of the user, and the system starts by finding the right eye of the user by searching the video image for the reflection of this light-the glint, distinguished by being a small, very bright point surrounded by a darker region. It then extracts a smaller, rectangular part of the video image (typically only 40 by 15 pixels) centered at the glint, and feeds this to an ANN. The output of the ANN is a set of display coordinates. The ANN requires more than the simple calibration that is required by the other techniques; it must be trained by gathering images of the user's eye and head for at least three minutes while the user visually tracks a moving cursor on the display. This is followed by an automatic training session that uses the stored images lasting approximately 30 minutes using the current technology, but then the system should not require re-calibration on the next encounter. To improve the accuracy of an ANN-based system, the corneal/pupil-based calculations can be augmented with a calculation based on the position of the glint in the eye socket. The great advantage of ANN-based techniques is that due to the wide angle of the base image, user head mobility is increased.

Eye movement information from the eye tracker can be typically divided into fixations and saccades, when the eye gaze pauses in a certain position, and when it moves to another position, respectively. The resulting series of fixations and saccades can be called a called a scan path. Most information from the eye can be made available during a fixation, but not during a saccade. The central one or two degrees of the visual angle (the fovea) can provide the bulk of visual information; the input from larger eccentricities (the periphery) is typically less informative and analysis algorithms can be structured accordingly. Hence, the locations of fixations along a scan path show what information loci on the stimulus are processed during an eye tracking session.

Scan paths are useful for analyzing cognitive intent, interest, and salience. Other biological factors (some as simple as gender) may affect the scan path as well. As a participant looks at a page on the internet, the eye-tracking device can focus on the pupil of the participant's eye and determine the direction and concentration of the participant's gaze. Heat maps represent where the visitor concentrated their gaze and how long they gazed at a given point. Generally, a color scale moving from blue to red indicates the duration of focus. Thus, a red spot over an area of your page might indicate that a participant, or group of participants, focused on this part of a page for a longer time. Saccade pathways trace the eye's movement between areas of focus. The movement is not unlike watching a hummingbird move between flowers—there are periods of attention and then rapid movement. A red circle may indicate the area of focus, while a red line indicates the flight.

Another capability of the eye tracking technology is eye movement analysis, which can provide valuable insight into users' overt visual behavior and attention. The most common method for determining the location of a user's observable visual attention is by identifying the fixations and saccades that best indicate where they are focusing on the stimulus in front of them.

A linear filter may be used when processing eye-tracking data to approximate eye movement signals, at least well enough to recognize a pattern. The salient eye movements that are typically identified by eye movement analysis are fixations, saccades (overt and covert), and smooth pursuits. Fixations are a result of one's desire to maintain gaze on a specific, stationary object. Smooth pursuits are similar except for the object of interest is in motion. Saccades represent a voluntary shift of focus from one fixation point to another.

Saccades can be detected and measured by two means as well: the position variance method and the velocity detection method. The position variance method identifies saccades as those moments in the signal in which the position of the eye changes rapidly. The velocity detection method uses an empirically determined velocity threshold. If the velocity of the signal is calculated as higher than the threshold, it is a saccade. Similarly, if it is below the threshold (as discussed above) it is a fixation. For both fixations and saccades, the velocity method is becoming more widely used because it is more suitable for real-time applications.

Beyond the analysis of visual attention, eye data can be examined to measure fatigue, the cognitive state and workload of a person. Some techniques have been validated in multiple contexts as a reliable indicator of mental effort. Driving a car, reading a magazine, surfing the internet, searching the aisles of a grocery store, playing a video game, watching a movie or looking at pictures on your mobile device are such applications of eye tracking. With very few exceptions, anything with a visual component can be eye tracked.

In another embodiment, the use of sensors on a contact lens can also be used for eye tracking eye responses and specifically VOP measurement. Employing multiple sensors on a contact lens can be used for detecting eye movement and contact lens orientation. The contact lenses may also employ the use of markers or the lenses could be magnetized. A multi-sensor contact lens can be placed in one or both eyes of a user and can actively determine movement activities of the eye. These sensors can be located on the surface of the lens or within the lens material. In another embodiment, an eye blink for a defined time can trigger the measurement of eye movement or turn on the device to begin the calibration for measurement. It is to be appreciated that both eyes of a human user generally blink at the same time, and thus in various embodiments only one multi-sensor contact lens is needed to generate a command to a remote device. Components on or within a contact lens can be of a shape, size, opacity, and/or positioned so as not to obstruct vision through an opening of a pupil of an eye when worn. Control features of multi-sensor contact lens can include issuing commands, adjusting content presentation, activating or deactivating options or components, or any other suitable functions. The multi-sensor contact lens can include either on or within its substrate a control circuit that can be coupled wirelessly to the multiple sensors.

In another embodiment, the multi-sensor contact lens can also communicate via a wireless network to a remote device. The remote portable smart device can include a wearable device, such as a head worn device or smart watch, or a non-wearable device, such as a remote mobile computer device, like that of a mobile smart phone, smart pad, pc and the like. The multi-sensor contact lens can use various kinds of sensors and they can be integrated in various combinations. The power component can include any suitable power source that can manage, receive, generate, store, and/or distribute necessary electrical power for the operation of various components of multi-sensor contact lenses. For example, the power component can include but is not limited to a battery, a capacitor, a solar power source, radio frequency power source, electrochemical power source, temperature power source, or mechanically derived power source (e.g., MEMS system). In another example, the power component receives or generates power from one or more of the sensors. A transceiver can transmit and receive information to and from, or within multi-sensor contact lens. In some embodiments, the transceiver can include an RF (radio frequency) antenna. In further embodiments, the video eye camera/eye tracker can be controlled remotely and/or alternatively with eye movements or voice activation or haptically. A remote device can also be used to control visual image(s) and the test procedures in embodiments of the invention. The remote device could also be used to process the data from head orientation sensors and eye tracking sensors and convert this information into the desired visual data for review.

In embodiments of the present invention, saccades can be tested by positioning two widely spaced targets in front of the person and asking the person to look back and forth between the targets. The technology used in faceguard can be used to calculate corrective saccades. It can also be used in the faceshield/visor or with an accessory device using an AR or mixed system (AR/VR) to calculate the corrective saccades (overt and covert). This system for the person is configured to collect eye images of the person in excess of 60 Hz and configured to resolve eye movements smaller than at least 3 degrees of motion. Eye movement data can include at least one fixation target presented to the subject in a defined position and configured to yield a voluntary saccadic eye response from at least one eye of the person. The latency, amplitude, accuracy and velocity of each respective corrective saccade and latency totals and accuracy is calculated. This platform can calculate, and display secondary, and higher, corrective saccades. Calculating corrective saccade measurements from the eye data can include:

(a) the total number of corrective saccades associated with the subject's eye movement to each fixation;
(b) first corrective saccade latency;
(c) first corrective saccade amplitude;
(d) first corrective saccade accuracy;
(e) first corrective saccade velocity;
(f) ratio of first corrective saccade amplitude to main saccade amplitude associated with the subject's eye movement to each fixation target; and
(g) ratio of total of corrective saccade amplitudes to main saccade amplitude associated with the subject's eye movement to each fixation target presented to the subject.

The corrective saccade measurements can include measurements for a first corrective saccade and at least a second corrective saccade. The corrective saccade measurements for each corrective saccade can include the latency, amplitude, accuracy and velocity of each respective corrective saccade. During the initiation of a saccade, a high frame rate may be required to anticipate the landing zone of a saccade. This can be used, for example, to activate grammatical elements rapidly (i.e., without the need to even perceive the target element) and/or remove a target element from the display eliminate corrective saccades and/or allow a new target to be chosen more rapidly using the so-called "gap effect."

Virtually, dynamic visual acuity (DVA), and retinal image stability (RIS), and foveal visual stability (FVS) testing can be used to determine the condition of a person's vestibulo-ocular reflex function. A DVA assessment can also include identifying a series of images or optotypes but with the addition of a head movement along an axis at a minimum rotational rate, engaging the vestibular system. The displayed images may also be dynamically moving in any direction, and can be random in position, appearance and presentation. Specifically, the image or visual element to be identified can be seen coming from any direction, randomly or with a specified pattern of motion, and may have different shapes, features, colors, sizes, orientation, patterns, or identifying characteristics, in a specific plane of axis or in variable plane, which the person must identify while the head in motion or rotating. The person can then provide feedback regarding what they see via an on-screen gesture, keyboard, smart device (e.g., defined as an electronic device, generally connected to other devices or networks via different wireless protocols such as Bluetooth, NFC, Wi-Fi, 3G/4G/5G cellular, etc., that can operate to some extent interactively and autonomously), eye or other physical response or by voice response. The comparison of the smallest image, visual image or optotypes correctly identified or the comparison of the correct numbers of images, visual elements or optotypes in both the DVA and SVA tests can determine if the person has a defect in his or her vestibulo-ocular reflex functions.

In embodiments of the present invention, AR or Mixed (AR and VR) platform systems, used with the face shield, visor or attached accessory device can have the unique advantage of measuring smooth pursuit (e.g., pursuit tracking during visual pursuit) in any plane, at various frequencies and in a variety of scan paths. As an example, eye tracking and visual or smooth pursuit can be done by visually observing a moving image traditionally in a horizontal or vertical plane or alternatively in a saw-tooth, sinusoidal, square-wave, snake-like, torsional, looped or other non-fixed plane of motion, which is more natural to what the normal person experiences in everyday life. Convergence movements can be evaluated by having the person fixate on an object as it is moved slowly towards a point right between the person's eyes. Vergence is an oculomotor function, described as disconjugate movement of the eyes to track images varying in depth over the binocular visual field and is commonly affected following concussions and mTBI. Embodiments of the present invention can measure this by presenting a visual object to the subject and detecting and measuring the position of the eyes and pupil area parameter. The visual object can move linearly or in sinusoid or another scan path toward and away from the subject at 0.1-2 Hz. The responses from both eyes are analyzed and compared to determine the coordination. In addition, the eyes can be observed and measured at rest to see if there are any abnormalities such as spontaneous nystagmus, disconjugate gaze (eyes not both fixated on the same point) or skew deviation (eyes move upward (hypertropia), but in opposite directions, all resulting in diplopia (double vision). All of these evaluations can be measured with VR or AR platforms. Similarly, these measurements can be made with the faceguard without the AR visual display.

In embodiments of the present invention, pupillometry tests can easily be observed with the technology attached to the faceguard, in the faceshield or visor or with a VR platform. Pupil measurements can be calculated independently for each eye when visualizing an image stimulus and the responses can be compared. Pupil measurements can include: pupil diameter with visual stimulus and after stimulus, average pupil constriction velocity, average constriction latency, average pupil dilation velocity, maximum pupil constriction and dilation velocity, pupil constriction acceleration, and pupil dilation acceleration. The faceshield allows the use of the testing using an AR and/or mixed reality system (AR and VR), as the pupil can be measured on each side with variation of the levels of light. Both eye movement and peripheral vision testing can easily be measured in AR, VR or mixed (AR and VR) systems. Eye movement testing can also be called extra-ocular muscle function testing is an examination of the function of the eye muscles. These tests observe the movement of the eyes in six specific directions. Peripheral vision testing is also called visual field testing. Testing the visual fields consists of confrontation field testing, in which each eye is tested separately to assess the extent of the peripheral field. Target detail within the peripheral field-of-view can be altered without attracting attention. In a process known as "change blindness," it is also difficult to discern visual changes (that attract attention) if the changes are introduced slowly or at times when an observer is not looking.

In embodiments of the present invention, the technology in the faceguard or the face shield or visor or accessory head worn device using the AR or mixed (AR and VR) system or the VR head-worn device can be configured to:
(a) collect eye images in excess of 60 Hz;
(b) resolve eye movements smaller than at least 3 degrees of motion;
(c) measure when a stimulus is presented to only one eye of the subject or both eyes;
(d) yield a pupil eye response from at least one eye of the person;
(e) measure pupils in each eye independently for the person's left and right eyes; and
(f) compare pupillometry measurements for the left and right eyes.

Another embodiment involves dynamic control of the frame rate (i.e., number of images acquired per unit of time) of the one or more cameras that view regions of one or both eyes. Camera frame rate is a major determinant of the ability to determine and measure rates and directions of movement (i.e., velocities) of objects within images of an eye. The muscles within the eye are capable of movements that are the most rapid of all muscles within the human body. Thus, increased camera frame rate can be critical in some cases to more accurately and robustly measure dynamic movements of an eye and/or its components.

Modern cameras are capable of operating over a wide range of frame rates. Instantaneous frame rates can also be adjusted (i.e., governed by so-called "clock" circuitry) as frequently as on an image-by-image basis. Closely aligned with camera frame rate is the acquisition time required to collect each image. The maximum time a camera can take to acquire an image is the inverse of the frame rate (i.e., the total time of a frame=1/frame rate). However, modern-day digital cameras also have the ability to limit the time over which they detect photons during the image acquisition process. Limiting the time to acquire photons is known in the art as "electronic shuttering." Shuttering light (including infrared) collection times to very brief intervals (typically in the order of microseconds to milliseconds) "freezes" images, allowing a clearer view of moving objects since object edges are spread over fewer pixels. On the other hand, longer acquisition times allow the detection of more photons during each image, increasing the amplitude (i.e., intensity within each pixel) of camera images and generally increasing signal-to-noise ratios. Although micro-movements can be useful to infer some aspects of a user's state (see below), they can interfere with directional and distance measurements of smooth pursuit and voluntary saccades. Higher frame rates allow algorithmic approaches to compensate for micro-movements by removing oscillations/movements at such frequencies or other mathematical approaches such as averaging results. Brief acquisition times can also be used to reduce image blur associated with micro-movements. The key to accurately determining initial saccadic direction and speed is the acquisition of camera images at high frame rates (typically hundreds of frames per second). Several techniques are available to acquire a rapid sequence of images immediately following a saccadic launch: 1) Once a saccadic launch is detected when sampling at a lower frame rate, the camera is immediately switched to a higher frame rate. 2) Camera circuitry (only) can be constantly run at a high frame rate, storing images within a circular buffer. Not all images are transferred out of the camera buffer and processed during normal operations. When a saccade is detected, rapidly sampled images that had been stored in the camera buffer can be retrieved for processing. 3) Frame rate can be adjusted based on the "context" of eye signal control. High frame rates can be maintained throughout these sequences.

Using an AR or VR display, one or more alphanumeric characters, halos, cursors, arrows, or other symbols may be superimposed within the display onto or adjacent to a particular object. These superimposed images or visual elements may indicate a particular meaning to the device user and this meaning may be assigned to the object so that it can be included in the eye signal language (in the same general manner as virtual icons). As examples, a halo can be placed around a physical light switch such that it can be the object of an action (e.g., turn on) or the name of a person can be displayed adjacent to the person's (real) face, allowing text or mail to be sent to that person using the eye signal language. Target or visual element fixation and image gaze data may be used within a gaze-based user interface enabled by an interaction model used with augmented reality or virtual reality. Such a user interface may also be multimodal incorporating head movement, hand movement, voice, and other physical or measurable brain-generated signals.

In further embodiments, any one of the tests, images, or visual elements described can also be visualized in a wearable display that includes a substrate guided optical device, known as the light-guide optical element system. Such a display can be a three-dimensional display. The display can be made up of an array of many small curved mirrors. Light could be delivered to that array via optical fiber. Each of the tiny mirrors could reflect some of that light to create the light field for a particular point in 3-D space, as a waveguide reflector array projector. The array could be semi-transparent to allow a person to see the real world at the same time. Multiple layers of such tiny mirrors would allow the display to produce the illusion of virtual objects at different distances. Planar wave guides or layers can be stacked to create a multifocal display in which each 2D planar wave guide, layer, column or set provides optical paths independently of other 2D planar wave guides, layers, columns or sets, allowing each to provide a respective focal or depth plane in a 3D image. This can include a series of linear or rectangular cylindrical wave guides arranged in vertical (xy) columns to create a planar 2D wave guide. This can include multiple 2D planar wave guides, columns, layers or sets, each corresponding to a different virtual depth plane. In such an embodiment using a partially transparent wave guide reflector array projector apparatus, a multiple depth plane three dimensional (3D) display system can visually provide multiple virtual depth planes at respective radial focal distances to simulate a 4D light beam field. The array of curved micro-reflectors can be oriented and positioned to project virtual images or visual elements at specified radial distances. The curved micro-reflectors typically partially reflect and partially pass electromagnetic energy, for instance optical wavelengths of light. The micro-reflectors can have one or more surface curvatures, and the surface curvatures may vary in each wave guide layer and the array can convert an input light beam from beam splitters into a stack of two-dimensional projections of virtual depth planes that recreates a three-dimensional volume on a display.

Embodiments of the invention can use miniature video cameras. The image of the eye can be tracked and allow the person's horizontal, vertical, and/or torsional (rotary) vestibulo-ocular responses to be measured. A moving visual target or visual element can provide a method for tracking, for optokinetic (OPK) testing, for saccade detection and measurement, for gaze fixation testing, for DVA measurement and for VOR testing. In the Active Head Rotation (AHR) horizontal test, the subject moves their head left and right randomly to the auditory signal and visual presentation. The speed of the signals increases through 1 Hz up to a maximum of at least 5-6 Hz. The person will attempt to keep moving the head back and forth at the speed of the beeps. For AHR Vertical, this test is conducted in the same manner as the horizontal test above, except that the head motion is up and down rather than left and right In further embodiments, the VR/AR system can include a head mounted system with at least one, and typically two, digital camera(s) trained on the person's eyes and which the cameral can have auto-tracking. Each camera can be connected to and/or powered by a computer, such as through a "firewire" type connection. The computer may be a laptop portable computer or other digital device. The digital cameras may allow for digital centering of the person's pupil at least in one direction through concentrating on the region of interest, and can be in multiple directions. The use of digital centering eliminates the need for a mechanical adjustment mechanism in the given direction.

In another embodiment, the eye sensor can be further configured to capture a 3D image of the iris. In another embodiment, the eye sensor can be comprised of an array of transparent light detectors based on graphene. In another embodiment, the system can include an illuminator that is configured to provide illumination in a visible, LED or infrared light spectral band for the eye sensor to capture the 3D image of the iris. In further embodiments, the eye sensor can be a microlens array light field camera (LFC) or plenoptic camera. Holograms can be used to blend the digital world with the real world in the AR systems (to aid in the testing and measurement of the eye movement, acquire more immersive ways to be engaged in activity desired, and provide ways to teach, train, learn, explore, collaborate and create). This can enable a more immersive see-through multi-dimensional method for all of the visual or oculomotor tests described in this disclosure.

Embodiments of the present invention can comprise existing wearable display devices such as: (a) the VR devices manufactured by Sony, Samsung, Oculus, Carl Zeiss and (b) AR devices such as those manufactured by Microsoft, Vuzix, Google, Magic Leap, and DigiLens. Eye tracking sensors, such as digital video cameras, can be used to view such displays and to determine eye position information. Head tracking accelerometers are already commonly embedded within wearable devices of the type described herein. Acceleration and orientation relative to the earth's gravitational field based on the output of a head-mounted multi-axial accelerometer can provide information about relative head movements. When coupled with eye gaze direction and the tracking of vestibulo-ocular eye movements, absolute head position and movements referenced to viewed objects can be discerned. Within a wearable display system object position, direction, distance, speed and acceleration can be plotted. These display devices, with eye and head tracking sensors, provide a method to integrate head gestures with eye-signal control.

In embodiments of the present invention, eye movements, responses or reflexes and head movements can be detected and measured in a manner using VR and/or AR platforms, that are novel and unique compared to what has been done traditionally in the clinical laboratory. These embodiments enable a higher level of testing and measurement for these eye responses, particularly for the VOR and DVA. Embodiments of the present invention also provide unique methods to rehabilitate persons with vestibular system disorders, particularly those with peripheral vestibular disorders and especially those persons with vestibulo-ocular reflex abnormalities and/or abnormalities of the dynamic visual acuity.

In another embodiment, the images or visual elements presented for VOP tests (which can include DVA or other oculomotor measurements) can correspond to a plurality of depth planes provided to a viewer in the VR or AR display. The target image or visualized element may be different for each depth plane, which can provide a slightly different presentation of a scene or object. The target or visual element may be separately focused by each of the viewer's eyes, to provide depth cues based on the accommodation of the eye required to bring into focus different image features for the scene located on different depth plane and/or based on observing different image features on different depth planes being out of focus. These depth cues can provide credible perceptions of depth and add complexity to the testing and measurement.

Image Projection

Eye tracking, video recording, and specifically VOP measurement can be performed using a virtual retinal display or holograph imaging in another embodiment. A virtual retinal display (VRD), also known as a retinal scan display (RSD) or retinal projector (RP), is a display technology that draws a raster display, or bitmap, directly onto the retina of the eye. The user sees what appears to be a conventional display floating in space in front of them. However, the portion of the visual area where imagery appears must still intersect with optical elements of the display system. It is not possible to display an image over a solid angle from a point source unless the projection system can bypass the lenses within the eye. In a conventional display a real image is produced. The real image is either viewed directly or, as in the case with most head-mounted displays, projected through an optical system and the resulting virtual image or visual element is viewed. The projection moves the virtual image or visual element to a distance that allows the eye to focus comfortably. No real image is ever produced with the VRD. Rather, an image is formed directly on the retina of the user's eye. Eye movement and head inertial tracking can be measured while being connected to a virtual display system. The measurements can also be triggered with an external "micro-controller". Not only can VOR testing and DVA measurement be done with the virtual display, but it can also be used for other "immersive testing", sport training, military training, commercial medical education or teaching.

Therefore, in an alternate embodiment, the camera can track the eye movement and measure the VOR using synthetic 3D displays such as holographs or augmented reality display imaging.

Although the VRD is an output device, the technology lends itself to augmentation with eye tracking or eye gaze systems for input. The VRD system scanning light into only one eye allows images to be laid over one's view of real objects. The VRD system also can show an image in each eye with an enough angle difference to simulate three-dimensional scenes with high fidelity. The eye tracking can enable the fovea on the retina to always maintain good focus ability and as the pupil changes position, eye tracking with movement of the eye follows. As the eyes move, the foveation point can also change to achieve better tracking. Using a refractive lens can be used to prevent distortion of eye tracking. The fovea centralis, also generally known as the fovea is a part of the eye, located in the center of the macula region of the retina. The fovea is responsible for sharp central vision (also called foveal vision), which is necessary in humans for activities where visual detail is of primary importance.

In another embodiment low-persistence-of-vision display can enable a user to see images at only 24 frames per second. Even though the images flash by repeatedly, the mind fills in the blanks and the user will see (relatively) smooth motion. By reducing the amount of information the user sees, the brain can smooth out virtual reality. A head attached tracker (also known as an orientation sensor), with an adjustable sample rate, but minimally 20 Hz, and with tracker latency can be used to enhance virtual reality's realism on response time. Using a combination of 3-axis gyros, accelerometers, and magnetometers, can make it capable of absolute (relative to earth) head orientation tracking without drift. Each display to the eye can be adjusted with interchangeable lenses that allow for dioptric correction and adjustments for inter-pupillary distance requirements can be done. The mounted head tracker, when used with the eye worn virtual display can move the images to match the user's head movements, and create a greater sense of being inside a high definition LCD, LED or 1080p OLED 3D (3 dimensional) images being displayed. A wireless interface can be used for sending the collected tracking data to a remote device. Hand held micro-controllers can also be used to manipulate the displayed images and obtain more of an immersive testing, training or rehabilitation experience.

In another embodiment, a different medium platform can be used to project the visual data for measurement of VOP, using a 3D (3 dimensional) virtual retinal display. In this embodiment, the virtual projection imaging device has no screen but can project images directly to the user's eyes. This screen-less display with the image displayed directly to the retina can also use a multiple micro-mirror design and low power light source. The image display quality can display a separate WXGA resolution (1,280×768) image directly onto the retina of each eye. The displayed images can be generated with reflected rather than emitted light. While LCD and OLED panels are emissive light, this display can project reflective light directly into the eye and mimicking more natural vision. The resolution and frame rate (minimally 240 frames/sec) can be high. Each eye can be focused independently focus and adjustments can be made to acquire a single image when wearing the device. Head inertial tracking and eye tracking can be incorporated in the head worn device. Two discrete images can be projected directly onto the retinas of the user and the optical elements can be individually adjusted.

To create an image with the VRD a photon source (or three sources in the case of a color display) can also be used to generate a coherent beam of light. The use of a coherent source (such as a laser diode) can allow the system to draw a diffraction-limited spot on the retina. The light beam can be intensity modulated to match the intensity of the image being rendered. The modulation can be accomplished after the beam is generated. If the source has enough modulation bandwidth, as in the case of a laser diode, the source can be modulated directly.

The resulting modulated beam is then scanned to place each image point, or pixel, at the proper position on the retina. Varieties of scan patterns are possible. The scanner could be used in a calligraphic (vector) mode, in which the lines that form the image are drawn directly, or in a raster mode, much like standard computer monitors or television. Use of the raster method of image scanning allows the VRD to be driven by standard video sources. To draw the raster, a horizontal scanner moves the beam to draw a row of pixels. The vertical scanner then moves the beam to the next line where another row of pixels is drawn.

After scanning, the optical beam must be properly projected into the eye. The goal is for the exit pupil of the VRD to be coplanar with the entrance pupil of the eye. The lens and cornea of the eye will then focus the beam on the retina, forming a spot. The position on the retina where the eye focuses the spot is determined by the angle at which light enters the eye. This angle is determined by the scanners and is continually varying in a raster pattern. The brightness of the focused spot is determined by the intensity modulation of the light beam. The intensity modulated moving spot, focused through the eye, draws an image on the retina. The eye's persistence allows the image to appear continuous and stable. Finally, the drive electronics synchronize the scanners and intensity modulator with the incoming video signal in such a manner that a stable image is formed.

Liquid crystal displays (LCDs) currently are often used in display devices for the presentation of information. LCDs with a display resolution of 1080p HD or greater can provide the image quality that is best for VR or AR systems. An image that is generated electronically is viewed with the optical system of the eye. The image seen is subject not only to the quality of the optical system of the eye, but also to the quality of the display and the environment in which the display is located.

With a VRD, defects in the eye's optical system, such as damaged cornea and lens and reduced retinal sensitivity could be bypassed, as well as the problems of the display environment, such as ambient brightness, angle-of-view and display brightness. Additionally, the seen image could be augmented with other information and brightness of the system does not affect the image formed on the retina. It is believed that VRD based Laser or LED displays are not harmful to the human eye, as they are of a far lower intensity than those that are deemed hazardous to vision, the beam is spread over a greater surface area, and does not rest on a single point for an extended time. Optical damage caused by lasers comes from its tendency to concentrate its power in a very narrow area. This problem is overcome in VRD systems as they are scanned, constantly shifting from point to point with the beams focus. If the laser stops scanning, beam stays focused on one spot can cause permanent damage to the eye. This can be prevented by an emergency safety system to detect the situation and shut it off. Apart from the advantages mentioned before, the VRD system scanning light into only one eye allows images to be laid over one's view of real objects. For example, it could project an animated, X-ray-like image of a car's engine or the human body.

VRD system also can show an image in each eye with an enough angle difference to simulate three-dimensional scenes with high fidelity. VRD can refocus dynamically to simulate near and distant objects with a far superior level of realism. VRD also supports proximity sensing. This means it can provide the illusion of being able to actually be more closely involved with the projected images.

In another embodiment a virtual image projector can also be comprised of a laser configured to form a narrow beam, multiple other optics, and a controller. The multiple optics each have a diffraction grating. One optic can be arranged to receive the narrow laser beam and to project a one-dimensionally dilated beam into the second optic. The second dilation optic can be arranged to receive the one-dimensionally dilated beam and to project a two-dimensionally dilated beam, which the can provide a virtual image. The first and second redirection optics are each operatively coupled to a transducer. The video-display eyewear can resemble eyeglasses and can include a pair of projectors that project virtual display images for view by a wearer. The virtual display images are projected directly in front of the wearer's eyes. The device can include a wearable mount configured to position the projectors a short distance in front of the wearer's eyes. The device can also include controller, which controls the internal componentry of the projectors in order to form the virtual display. Projectors may project virtual display images of infinitely distant objects, where the lens of the human eye adjusts to an infinite or near-infinite focal length to focus on such objects. The projectors may be at least partly transparent, so that the wearer can see external objects as well as the virtual display images or visual elements. The glasses include lenses arranged in front of the projectors and they can be arranged in front of the projectors. The lenses may be configured to correct the focus and/or brightness of the external objects for the comfort and vision needs of the wearer. This arrangement may allow the wearer to shift his or her focus between the external objects, a finite distance away, and virtual display images an infinite distance away.

In an alternative embodiment, the controller can cause projectors to project the same virtual display image concurrently, so that the wearer's right and left eyes receive the same image at the same time. In another embodiment, the projectors may project slightly different images concurrently, so that the wearer perceives a 3 D stereoscopic image.

In another embodiment, eye movement is measured without a camera system and utilizes electrodes placed on the surface of the skin around the eye(s). It is based on the principal where the eye acts like a battery: the cornea is the positive pole and the retina is the negative pole. Electrodes located in specific peri-orbital areas (e.g., around the eye) pick up the corneal-retinal electrical potential variation caused by eye movements, which are then amplified and sent to a recording device. Two (2) or three (3) channel recording devices can be used to record all eye movements. An active electrode is placed next to the external corner of each eye and the third electrode is placed on the frontal midline in such a way that the three recording channels are configured as an isosceles triangle. Three bipolar derivations are set from the active electrodes, thereby making it possible to identify horizontal, vertical and oblique eye movements. Measuring the slow component velocity of nystagmus takes into account the directional influence of responses according to the vector projection of eye movements.

Head Tracking

Head tracking on a head-worn unit can be performed by using an inertial measurement unit (also called an IMU or 'tracker'). An IMU is an electronic device that measures one or more DOF (such as position, velocity, orientation, and/or gravitational force, as was described previously in this disclosure) by using one or more sensors. Sensors used in IMUs can include one or more accelerometers, gyroscopes, and magnetometers. A MEMS (micro electro mechanical system) gyroscope, a MEMS accelerometer, and a MEMS magnetometer can be used as complementary and/or redundant sensors to accurately support a full range of motion in a three-dimensional space. Accelerometers work well for measuring five DOF: linear movements in three axes; and absolute tilt about the two axes perpendicular to gravity (i.e., pitch and roll). Accelerometers cannot easily measure rotation about an axis aligned with gravity (i.e., yaw). Magnetometers work well for measuring absolute yaw providing a sixth DOF. Gyroscopes provide a stable way to measure changes the three rotational DOF (pitch, roll, and yaw). Devices that measure these three displacements and measure each of the three rotations in two different ways are typically called nine DOF IMUs. The input signals from the accelerometer(s), magnetometer(s), and gyroscope(s) in these nine DOF IMUs are often processed using a Kalman or a Madgwick filter located in a sensor pre-processing unit to provide output signals that have been optimized for accuracy, stability, and response rate.

The head tracking inertial system can be mounted to the head in numerous configurations. Examples include: within a face guard, face shield, visor; with helmets, caps, straps or other head worn covering; in the center of eyeglasses; at the nose piece; in the side of the eyeglasses; in the ear or attached to the ear; and/or attached to the teeth with mouth guards, prosthetic attachments, or fixation with other oral appliances. In other embodiments, the head tracking can be done from sensors in a hand-held smart phone, smart pad, from another sensor system attached to a body part, or from a remote device viewed by the user. When used in VR and AR platforms, the head tracking technology can normally refresh on-screen images 125-1250 frames per second (or Hz). Higher frame rates reduce movement lag. For specific applications, the refresh rate may be lower than 125 frames per second (fps) or higher than 250 (fps), depending upon the platform used, the application, and type of measurement or testing being performed. For performing some tests, such as the head impulse test a sample rate or refresh rate of 250 Hz or higher might be necessary to capture the subtle eye movements, such as overt and/or covert saccades. Reducing the lag between head movement and the headset response will mitigate symptoms of motion sickness or visually induced motion sickness. The resolution use can be variable depending on the application or platform used, but may be chosen as 1080×1200 or 2160×1200-2560×1440 or higher and the latency between images should be short (20 milliseconds or less). In further embodiments, the head tracker can be controlled remotely and/or alternatively with eye movements, or voice activation or haptically.

Fourier Analysis

A Fourier transform can be used to convert the relationship between an input (such as head motion) and an output (such as eye movement) in the time domain to a relationship in the frequency domain. By doing this, VOP can be measured for natural motion in a non-clinical environment. As described previously, one of the traditional ways of measuring VOR has been to oscillate a subject's head at a fixed frequency and then to measure how quickly the eyes respond. For this kind of testing, a frequency of 0.5 Hertz would correspond to one cycle every 2 seconds. A cycle corresponds to the combination of one movement to the right and one movement to the left. These movements are typically in the form of a sine wave. The gain at this frequency would be the amount of compensation that the eyes make to the movement of the head. A gain of −1 (also often written as a gain of 1) is perfect because the eyes have rotated exactly the same angle as the head, but in the opposite direction. A gain of −0.75 (often written as 0.75) means that the eyes only compensated for 75% of the head rotation. The phase or phase lag describes how much later the eyes moved than the head. A phase or phase lag of 0 would mean the eyes followed exactly. A phase or phase lag of 45 degrees at a frequency of 0.5 Hertz means that the eyes were delayed by $\frac{1}{8}^{th}$ of 2 seconds (or 250 milliseconds) because 45 degrees corresponds to $\frac{1}{8}^{th}$ of a full 360-degree cycle. To determine gain and phase at a variety of frequencies using the traditional approach of oscillating the head in a clinical environment one would repeat the above test at a variety of frequencies and record the results. This method requires control over each input frequency and measuring the gain and phase of the eye response separately for each frequency, which will not work in a non-clinical setting having natural motion.

Any time-varying signal (such as the natural motion of an object in one dimension) can be converted to a series of sine waves. This conversion from a time-varying signal to a series of sine waves is called a Fourier transform. Fourier transforms can be discrete or continuous. A continuous Fourier transform is one in which the time-varying signal is converted to an entire range of frequencies with no gaps between the frequencies. A discrete Fourier transform is one in which the time-varying signal is converted to a specific set of frequencies, such as the series 0.125 Hz, 0.25 Hz, 0.5 Hz, 1.0 Hz, and 2.0 Hz. Discrete Fourier transforms are easier to calculate using digital electronics. By converting the observed natural yaw of the head as a function of time using a Fourier transform, one can generate a graph showing the amplitude of the input signal that the eyes would need to compensate for in order to follow a stationary image or visual element. By converting the sensed horizontal movement of the eyes at this same time using a Fourier transform, one can generate a second graph showing the amplitude of the eye signal that compensates for the head movement. By comparing these two graphs mathematically, it is possible to determine gain at various frequencies directly from the natural head yaw movement. Similar mathematical calculations can be made to determine phase. The same method can be used to determine gain and phase in other dimensions such as pitch of the head versus the sensed vertical movement of the eyes, etc. Discrete Fourier transform calculations of this type can be performed by a microprocessor that receives the time-varying orientation signals from a head orientation sensor and the time-varying signals from an eye orientation sensor using mathematical calculations capable of being understood by anyone skilled in the art.

It should be noted that embodiments of the present invention can be implemented using dynamic analysis tools other than or in addition to Fourier Transform analysis, examples of which can include regression analysis, multi-variable regression, band pass filters, time domain analysis, Bode plots, Nyquist plots, waterfall diagrams, Campbell diagrams, resonance analysis, power spectral density analysis, frequency response function, coherence analysis, correlation analysis, cross power spectrum analysis, impulse response analysis, octave analysis, order analysis, waveform analysis, and/or any other dynamic system analysis tool capable of being understood by those skilled in the art.

Other Potential System Elements

An example of a portable and wearable computing and head mounted display system can include an eye tracking and measuring system, a connected head mounted display tracking and measuring system, an optical system, peripherals, a power supply, a microprocessor, a memory, and a user interface. Components of the system may be configured to work in an interconnected fashion with each other and/or with other components coupled to respective systems. For example, the power supply may provide power to all the components of the system. The processor may receive information from and control the eye tracking system; the head mounted tracking system, the optical system, and peripherals. The processor may be configured to execute program instructions stored in the memory unit and to generate a display of images on the user interface. The display to the user can be presented as a 2D or 3D (3 dimensional) virtual display.

The system may include or be coupled to peripherals, such as a wireless communication interface, a touchpad, an integrated microphone, a high definition (HD) camera, and a speaker. A wireless communication interface may use 3G cellular communications, such as CDMA, EVDO, GSM/GPRS, or 4G cellular communications, such as WiMAX or LTE. Alternatively, wireless communication interface may communicate with a wireless local area network (WLAN), for example, using Wi-Fi. In some examples, wireless communication interface may communicate directly with a device, for example, using an infrared link, Bluetooth, near field communication, or ZigBee. In addition, other wireless interface communication can be used with "off-the-grid" networks (such are FireChat) where there is not cellular phone service or no internet connection.

The power supply may provide power to various components in the system and may include, for example, a rechargeable lithium-ion battery, solar power, mechanical power or various other power supply materials and types known in the art.

The processor may execute instructions stored in a non-transitory computer readable medium, such as the memory, to control functions of the system. Thus, the processor in combination with instructions stored in the memory may function as a controller of the system. For example, the processor may control the wireless communication interface and various other components of the system. In other examples, the processor may include a plurality of computing devices that may serve to control individual components or subsystems of the system. The processor, in conjunction with the memory unit, may perform analysis of the images obtained by the infrared camera.

In addition, the memory unit may store data that may include a set of calibrated wearer eye pupil positions and a collection of past eye pupil positions. Thus, the memory may function as a database of information related to gaze direction. Calibrated wearer eye pupil positions may include, for instance, information regarding extents or range of an eye pupil movement (right/left and upwards/downwards), and relative position of eyes of the wearer with respect to the HMD. For example, a relative position of a center and corners of an HMD screen with respect to a gaze direction or a gaze angle of the eye pupil of the wearer may be stored. Also, locations or coordinates of starting and ending points, or waypoints, of a path of a moving object displayed on the HMD, or of a static path (e.g., semicircle, Z-shape etc.) may be stored on the memory unit.

The system may include the user interface for providing information to the wearer or receiving input from the wearer. The user interface may be associated with displayed images, a touchpad, a keypad, multiple cameras, buttons, a microphone, a haptic device, and/or other peripheral input devices. The processor may control functions of the system based on input received through the user interface. The system and/or testing function controls and input connections can be in a head-worn device and/or in a remote device. The system can be activated or controlled using an electronic keypad, voice, haptic, eyelid movement, ocular orientation, and/or any body movement. The computing system could be a distributed computing system. The computing system could comprise cloud computing.

One or more of the described functions or components of the system may be divided up into additional functional or physical components, or combined into fewer functional or physical components. For example, the infrared camera may be mounted on the wearer separate from the system. Thus, the system may be part of a portable/wearable computing device in the form of separate devices that can be worn on or carried by the wearer. Separate components that make up the wearable computing device may be communicatively coupled in either a wired or a wireless fashion. In some further examples, additional functional and/or physical components may be added.

The system may be configured as, for example, face guard, face shield, visor, eyeglasses, goggles, a helmet, a hat, a visor, a headband, or in some other form that can be supported on or from a head or parts of the head of the wearer. The system may be further configured to display images or visual elements to both eyes of the wearer. Alternatively, the system may display images or elements to only one eye, either a left eye or a right eye.

If used as part of a head mounted display (HMD), the system may include a gyroscope, a global positioning system (GPS), magnetometer, and an accelerometer. The head mounted display tracking system may be configured to provide information associated with a position and an orientation of the HMD to the processor. The gyroscope may include a microelectromechanical system (MEMS) gyroscope or a fiber optic gyroscope as examples. The gyroscope may be configured to provide orientation information to the processor. The GPS unit can include a receiver that obtains clock and other signals from GPS satellites. The GPS unit can be configured to provide real-time location information to the processor. The HMD-tracking system may further include an accelerometer configured to provide motion input data to the processor.

Additional Embodiments

In one embodiment, the device or method uses utilizes eyewear with an eye-tracking and measuring sensor, a head motion sensor and compares the gain and phase of each (e.g., an electronic circuit generates a comparison of the three axes from the head orientation sensing element with eye movement signals from the eye sensor to calculate a gain and phase of the eye movement response to head rotation, in the opposite direction). The eye orientation sensor senses vertical movement and horizontal movement of at least one eye. A visual target is provided in the eye worn lens, which can be otherwise transparent, translucent or opaque. The device or method can present this visual target to one eye (monocular) or both eyes (binocular). The device or method is sufficiently comfortable, secure to the head and light-weight to allow the user to have active head movements while wearing the device. Wearing such a mobile or portable, head worn or eye worn device requires a power source. If the power source is in the head-worn device of the eye tracker or head tracker it can be rechargeable by a wireless interface.

The device can measure the relationship between motion of the head in this environment and VOP. The data acquired can be uploaded to a remote position from the user for display and interpretation or transmitted wirelessly to a smart phone, wearable display device or other hand-held device or other computer source. The eye tracker latency delay can be in the range 1 ms-10 ms and can have options to set the latency. The device can be charged with a wireless interface. The head orientation sensor does not use an external pulsed magnetic field and senses pitch and yaw of the person's head in a range of frequencies that comprises at least one frequency greater than 0.01 Hertz and less than 15 Hertz. The head orientation sensor can comprise an IMU. The head orientation sensor can comprise one or more accelerometer(s), magnetometer(s), and/or gyroscopes.

In one embodiment, a single camera system is used for the eye tracking. In another embodiment, a multi-camera system is used and the cameras can be located in the lens, framework or eye or head worn device or located remotely. The camera control unit could be activated by touch, head movement, voice, a timer, an external wireless signal, or by placing the device on the head (e.g., putting on the head-worn unit). An eye blink, for a defined time, could also trigger the camera. An algorithm measuring blinking time and duration to discriminate between voluntary and involuntary eye blinks could be used to issue a command to a controller to operate the camera system. The controller could communicate with other parts of the system to support the commands. The camera could have a resolution of at least five megapixels and could be capable of recording at 720p or 1080p resolutions. The camera could have a microphone for voice commands, and at least 12 GB of usable storage. The camera could support Bluetooth and/or Wi-Fi. The camera could be part of, or work with an Android or iOS smartphone. The camera could have at least a 25° field of view. The camera system could also comprise an onboard OMAP (Open Multimedia Applications Platform) processor running the Android or iOS operating system. The entire system could be a smartphone that includes an embedded eye camera sensor with a head motion sensor. Providing direct image overlay over the wearer's main line-of-sight, coupled with the motion sensors and camera, it can enable true augmented reality capability. A smartphone or similar device (such as a tablet computer) could also be used to provide wireless remote control.

In one embodiment, the eye-tracker uses the center of the pupil and infrared and/or near-infrared non-collimated light to create corneal reflections (CR). The vector between the pupil center and the corneal reflections can be used to compute the point of regard on surface or the gaze direction.

In an alternative embodiment of a binocular system, two mirror-image optical systems are mounted on each side of the eyeglasses frame. The corneal reflections are generated by illumination with two infrared LED's mounted to the glasses frame. These LED's also serve to illuminate the pupil. The use of infrared (IR) light allows for invisible illumination of the eye. The use of multiple corneal reflections extends the linear range of the system by ensuring that one corneal reflection is always visible on the spherical surface of the cornea even with eccentric gaze. The images of the pupil and corneal reflections are reflected off of an IR mirror positioned in front of the subject's eye and directed to the cameras. This mirror is transparent to visible light and thus does not interfere with normal vision. The video image is sampled by a custom charge-coupled device (CCD) array that allows images to be sampled minimally at 20 Hz. Images from the CCD camera are processed in real time to obtain estimates of the corneal reflection and pupil center locations. Calibration of the eye tracker can be performed using a light source, such as a laser pointer, and calibration procedure looking at multiple objects or points (usually 5).

Another embodiment may use an OLED-based eyewear display which enables the eye tracking of a person with the use of an embedded IR display and camera in the see-through-lens of a head mounted/eye worn device. This can be worn as a monocular or binocular device with a transparent OLED display inside, which overlays digital information on top of the reflected light that strikes the eye. A bi-directional micro-display can be used in the head worn system for additional gaze triggered augmented-reality (AR) applications. The display contains both an active OLED matrix and integrated photodetectors that can track eye movement activity with front brightness up to 2000 cd/m$^2$.

Another embodiment can use a Liquid Crystal on Silicon (LCoS), field-sequential color, LED illuminated display. The display's LED illumination can be polarized and then shines through the in-coupling polarizing beam splitter (PBS) to the LCoS panel. The panel reflects the light and alters it to S-polarization at active pixel sites. The in-coupling PBS then reflects the S-polarized areas of light through the out-coupling beam splitter to a collimating reflector at the other end. Finally, the out-coupling beam reflects the collimated light into the wearer's eye.

In another embodiment, a low persistence OLED (Organic Light Emitting Diode) 1080p HD 3D (3 dimensional) virtual display can be utilized for VOP measurement. The OLED display may not be as bright as an LCD display, but it has a major advantage in delivering crisp, rapid movement without any smearing or ghosting of objects. Multiple separate cameras or a single large screen, which is split in half, can be used to provide two view points for each half of the screen. The two views can then be seen separately to either eye to with lenses in the head worn device, to provide a wider field of view. Orientation and movement can be tracked with the stereo 3D (3-dimensional) head tracker with 360 degrees. The user when being tested with the 3D (3-dimensional) virtual display has a sense of being "intimately around the points of visual focal interest". An additional embodiment of using a hand-held controller can also be used to sense motion anteriorly and posteriorly, with a 3D (3-dimensional) hand held mobile controller. Testing of the VOR can also be tested with pitch and roll of the head tilt. Predictive tracking (e.g., algorithm which can predict the next head position and orientation can help computing and updating) can be used to prevent latency issues and lessen motion disturbances while being tested. A bone conducting sensor incorporated in the framework can provide auditory/acoustic signals to the user. This data can then be stored, logged, interpreted and uploaded to a remote location.

The eye tracking system can be used with or without a light source. Therefore, another embodiment of eye gaze tracking can be provided with magnetized contact lenses tracked by magnetic sensors mounted on the user's eyewear and/or reflectors or markers on the contact lenses tracked by video-based sensors, also mounted on the user's eyewear. Tracking information of contact lenses from magnetic sensors and video-based sensors may be used to improve eye tracking and/or combined with other sensor data to improve accuracy of eye tracking. Contact lenses may be tracked by one or more mounted head worn cameras and/or magnetic sensors in order to resolve tracking information, such as position of the objects, the distance between the objects and a camera, and the like. Furthermore, reflective contact lenses improve blink detection while eye gaze tracking is otherwise unimpeded by magnetized contact lenses. Additionally, contact lenses may be adapted for viewing 3D (3-dimensional) information. Alternatively, another method could be to place four evenly spaced sensors on the inside of the contact lens, so they cover every angle of the eye movement. The sensors could even be embedded in the lens itself.

In further embodiments, magnetic sensors and video-based sensors may be used in combination to track a magnetized contact lens with one or more reflective patterns, provide blink detection, and eye movement. Other video-based sensors may be used to locate the head position of a user and prune noise from other magnetic or other light sources. Additionally, tracking information from contact lenses of both eyes may be used to improve accuracy.

Magnetized and reflective contact lenses may be utilized to browse menus of computer applications, control virtual characters of video games, select-drag-manipulate objects, and perform other trained or learned actions responsive to a user's eye movement or eye gaze. In further aspects, magnetized and reflective contact lenses can be used in any application that can benefit from eye and/or gaze tracking.

In one embodiment, magnetic sensors may be placed on a video game console or near the head of a user of a video game console to track the location and polarization of magnetized contact lenses. In another embodiment, video-based sensors may be used to track the location of reflective contact lenses transparent to normal light and reflecting one or more portions of the electromagnetic spectrum.

Contact lenses in embodiments can be passive (e.g., utilizing color or polarity for 3D viewing) or active, for example, using a liquid crystal layer that is normally transparent but darkens when a voltage is applied.

One of the advantages of using contact lenses for eye tracking and viewing 3D (3 dimensional) information is that they are more practical (i.e., smaller, light weight and easy to carry around) compared to some peripherals used for eye gaze tracking or for 3D information viewing. For example, glasses typically used for 3D information viewing or head-mounts typically used for eye gaze tracking can be complex and cumbersome.

In addition, contact lenses can offer highly accurate eye tracking information at low cost. For example, when contact lenses are used for eye gaze tracking, the performance can be better than the one that can be achieved with a camera-based eye tracking solution. Also, compared to camera-based solutions which require expensive high-resolution cameras, contact lenses can offer low cost solutions which make them more suitable for consumer products.

Accordingly, in various embodiments, a combination of marker-based and marker-less eye tracking techniques using contact lenses provide interacting with or controlling objects or menus of a video game, a projected visual user interface, an augmented virtual reality user interface, or the like.

In another embodiment contact lenses with embedded electronics inside such as LEDs, LCDs. or new nano-electronic materials can also be used for eye tracking. Applications of electronic contact lenses may be even more promising.

Trackers can constantly ping the sensors in the IMU to get information from them. The rate at which this happens is expressed as [samples] Hz (per second). The wearer of a head tracker may perform a gesture to indicate an attempt to unlock the head mounted camera display. For example, a gyroscope coupled to the head mounted display may detect a head tilt, for example, and indicate that the wearer may be attempting to unlock the head mounted display screen.

In one embodiment the head tracker comprises an IMU, an RGB (Red Green Blue) LED, an 800-925 nm infrared LED, a battery and wireless interface charger, a wireless interfaced micro-controller, and a transceiver. The gyroscope in the IMU can be capable of sampling rates up to 760 Hz, and the transmitter link can have the throughput to transmit that fully under 1 ms latency to the remote station. Full positional updates (fused information from all the sensors) from the IMU can be sent at a rate of at least 500 Hz. The IMU comprises sensors that can sense roll, pitch, and yaw, as well as inertia when the IMU is moved forward/back, left/right, and up/down. The IMU could be a nine DOF IMU.

Another embodiment can use eyewear that has elements within the transparent, opaque or semi-transparent lens comprised of: calibration points, light source and video camera for recording any eye movement. In this embodiment, no mirrors are utilized. The framework provides the power source, data logging capacity, software for measurement and can include: alarm signal for movement of the head, sensors to transmit collected data to remote source and data interpretation. This can be done with passive head movements or active head movements and an alarm in the device can trigger the timing event of head movement, rather than having another person move the user's head for more of an "active head movement test". Specifically, the electronic circuit can be triggered or turned on by verbal command (auditory input), by visual means (such as prolonged eyelid closure or other specific eyelid movement), mechanically (such as by the attachment of the head worn device to the head), with timer software programming, and remotely. Additionally, this worn device can provide software to detect a value or abnormality for eye response or eye reflex, where eye response (or reflex) might be VOR, DVA, DVS, or RIS. This eye response (or reflex) output could be reported as a binary (normal or abnormal) value or it could be reported as a score on a continuous scale, such as the way in which other physiologic parameters (such as height, weight, blood pressure, temperature, and many more parameters) are reported. If a score is reported, it could be a score for a single parameter at a single frequency, such as gain or phase at 0.5 Hertz, or it could be a multi-frequency composite score (such as gain or phase or a combination of gain and phase at a range of frequencies from 0.1 Hertz to 1 Hertz). The score could be for one eye or both eyes. The score could include measurement of asymmetry. An eye response (or reflex) score on a continuous scale or on a continuous composite scale (or a simple reporting of abnormalities), could benefit from a rehabilitative VOR eye-tracking program. This can then enable the person to develop normal VOP again or enhanced eye fixation and specifically RIS on a target of interest with head rotation or head movement, or improve other ocular response or reflex capabilities while performing occupational activities.

If the device does not need to be completely portable and self-contained, one can perform inertial head position and/or orientation tracking by transmitting external signals such as pulsed magnetic fields, optical signals, or audio signals to a transducer located on the head-mounted (eye-tracker) system. The transducer can be mounted on the eyewear/head for azimuth rotation. For example, a fixed transmitting device can radiate a pulsed magnetic field into which the head mounted receiver is immersed. The field is sensed by the receiver and processed by a microprocessor to provide three-dimensional position information as well as head elevation, azimuth and roll angles. The head tracker provides absolute angular and translational position measurements and does not require calibration for each person. The head tracker can operate with multiple receivers allowing for measurement of other important parameters such as hand position in hand-eye coordination studies. Other embodiments that use external signals can include the use of external infrared and ultrasonic signals to detect the position and orientation of the head or other part of the human anatomy.

The mounted head tracker sensor in the head worn/eye worn device can include an IMU of any type cable of being understood by anyone skilled in the art. The mounting of the head tracker can be in the center of the head worn device, or in the nosepiece with eyeglass device or on the sides of the eyeglasses. The head tracker can also be mounted to a removable in-the-mouth appliance, which is fixed to the tooth. It can also be incorporated into a mouth guard or retainer device. The mouth worn device can also generate a sound signal to produce imperceptible sound vibrations that are conducted via the teeth, through bone, to the cochlea and providing the user with signals to move the head.

Another alternative embodiment of the invention is an inertial angular orientation tracking apparatus mounted to the head worn device. Drift sensitive sensors, such as angular rate sensors, produce a signal that is integrated to give a signal that represents angular position. The angular position signal may drift, due to integration of a bias or noise in the output of the rate sensors. To correct this drift, compensating sensors, such as gravimetric tilt sensors and geomagnetic heading sensor(s) can periodically measure the angular position, and this directly measured position signal is used to correct the drift of the integrated position signal. The direct angular position sensors cannot be used alone for dynamic applications because the gravitational sensors are also affected by non-gravitational accelerations, and therefore only accurately reflect angular position when under the influence of no non-gravitational accelerations. Typically, the drift sensitive sensors are angular rate sensors, (these include: rate gyroscopes and vibrating piezoelectric, magneto-hydrodynamic, optical and micro-machined silicon devices) the outputs from which are integrated once. However, other suitable drift sensitive sensors include linear accelerometers used to sense angular rate, gyroscopic angular position sensors and angular accelerometers. Typically, the compensating sensors are inclinometers, accelerometers and compasses.

In another embodiment a head orientation and/or inertial tracking device can be used that is essentially "source-less", in that it can be used anywhere with no set-up of a source, yet it enables a wider range of virtual environment-style navigation and interaction techniques than does a simple head-orientation tracker, including manual interaction with virtual objects. This device can feature a source-less orientation tracker including an inertial sensor, a tilt-sensor, or a magnetic compass sensor.

In another embodiment, the device can include a position tracker such as an acoustic position tracker, a system that tracks LEDs, optical sensors or reflective marks, a video machine-vision device, a magnetic tracker with a hand-held magnetic source and sensors integrated in the headset or vice versa, or a radio frequency position locating device.

In an alternative embodiment, the present invention not only measures VOP (as the VOR or RIS with head movement), but also rehabilitates/retrains the user when an abnormality is present, to enhance the VOR and RIS or retinal visual accuracy with specific visual stimulation and head movements. This rehabilitation can be done for specific vestibulo-ocular pathologic findings. Specifically, when there is an abnormal VOR in the horizontal plane, specific algorithms of eye fixation on a target object, while the head is moving horizontally can be used to rehabilitate the abnormality. When the abnormal VOR is seen in the vertical plane, specific algorithms of eye fixation on a target object, while the head is moving in a vertical manner can be used to rehabilitate the abnormality. As the VOR is enhanced or improved, the DVA or RIS will be enhanced.

In one embodiment, the device or method could provide a sound signal and/or visual signal to alert or trigger the user to respond by moving the eye or head. Remote sensing, see through capability with the head/eye worn device, and the rendering of a visible target in broad daylight are all features that can be incorporated in embodiments of the present technology. The head/eye worn device or method could also collect the data, which could then be uploaded to a medical doctor, trainer, coach or other person at a remote location. This remote location could then provide verbal or visual feedback to the user and this feedback could be integrated with other information provided to the user.

In one embodiment the device or method disclosed here can also be used to help a person improve his or her VOR and DVS and accuracy used during activities in daily living, routine exercise, and high level athletic/vocational activities. This can be used to help a person improve his or her balance by challenging, exercising, enhancing, and/or retraining the VOR (fixation/re-fixation) used during activities in daily living, routine exercise, and high level athletic/vocational activities and therefore improving the retinal visual stability and accuracy of the fovea to remain fixed on the visual element. Thus, embodiments of the present invention can incorporate head movements in one or a number of planes as part of a systematic program for enhancing the VOR and DVA. Using the devices and methods described here it is possible for rehabilitation programs to incorporate head movement with stable image identification and image identification movement with the head remaining stable. The data obtained from the devices and methods described here can be used for wireless communications. The data can be embedded GIS or geographic information system of the eyes or a digital map of where the eyes are located relative to the head movement.

In an embodiment of the present invention, the main functions (head orientation sensing, eye tracking, and the display of an image or images can be performed by a general-purpose portable, battery operated, hand held device, such as a smartphone, computer pad, or other wearable computer device. For example, vestibulo-ocular performance could be measured in a virtual environment that was created by attaching a smartphone to a person's head, using the smartphone screen to display stereoscopic images, using the orientation sensors in the smartphone as a head tracker, and using the user-facing video camera to view and track the user's eyes. If the light from the display is insufficient, additional light could be provided by another source that could be operated using infrared (IR) or visible light. Eye tracking could also be enhanced by having the subject wear a contact lens or lenses that have markers on them that would be visible to the smartphone camera. Examples of configurations that could be adapted in this way include Google Cardboard and the Samsung Gear VR. Data on the smartphone could be stored, logged, interpreted, displayed, and/or transmitted to other devices. Transmission of data could use any of the communications technologies available on a typical smartphone including, but not limited to Bluetooth, WiFi, a cellphone signal, or a wired signal. The smart phone-based system could also use auditory signals for instructions, audio cues during the test, and/or alarms. This system could be used for passive head movement testing or active head movement testing. Additionally, this portable hand-held device or limb worn device can provide a software rehabilitative eye tracking program, if an abnormality is present. This can then enable the person to develop normal or enhanced eye or foveal fixation stability on a target of interest with head rotation or head movement, while performing their occupational activities. Additionally, fiduciary markers can be applied on the head to facilitate inertial head tracking. It would also be possible for the smartphone to be handheld instead of head-mounted and provide the head orientation sensing, eye tracking, and display functions.

In one embodiment, the device can be calibrated before it is used. When used in the laboratory setting, calibration can be performed by focusing on a distant target, such as a light bar or laser light which is projected to the wall. The image or visual element moves horizontally, vertically and then is center located. Typically, several trials are performed to establish reproducible results. During this test, the person is instructed to rotate the head from side to side horizontally or vertically to an auditory cue at frequencies ranging from 2 to 6 Hz. Eye movements are recorded including: direction, amplitude, and velocity of eye movements. Head inertial movements are recorded by the velocity rate sensor attached to the head. Tracking eye movement from spot to spot in this way is called "active tracking". When used in a non-laboratory or a non-clinical setting, similar testing can be performed if there are objects available to serve the same purpose as the distant target in the laboratory setting. Testing of this type allows gain, phase, and asymmetry to be measured separately at each frequency. A more sophisticated approach would be to ask the subject to follow an object that is not necessarily moving at one specific frequency, but at a combination of frequencies and then using a Fourier transform to convolve the gain, phase, and asymmetry at various frequencies directly from the complex waveform that was being followed by the subject.

As described in the previous paragraph, in some embodiments of the present invention, the head movement tracked and measured can be active. Another approach is to use and measure natural movement that normally occurs during normal activities or activities associated with a person's work and to compare that to the eye movement that occurs at the same time using a Fourier transform. This approach can be called "natural tracking" A third approach is to attach the head to something that then forces the head to move in a specific pattern—which is called "passive tracking."

In embodiments of the present invention, head movement testing can sense horizontal, vertical or torsional movements at various linear velocities, angular velocities, linear accelerations, angular accelerations, or frequencies. Natural test method testing in the horizontal plane could utilize focusing on a target moving across the horizontal visual field. Watching a moving object ascend and descend in the air can serve as a natural vertical test.

Any combination of the discussed embodiments of head inertial trackers and eye tracking systems can be used to measure the ocular response (e.g., VOR) with head movement. If active tracking is used, the user visualizes a target of interest while moving the head. The target the user is focused on can be seen through a see-through lens (e.g., with the face shield or visor) or, if wearing other semi-transparent or non-transparent head worn applications (such as a pair of goggles for VR display), the target may be displayed as a 3D image, hologram or some other light source image. Video camera eye orientation tracking, using invisible or visible light, simultaneously can be used with head tracking. As the head moves, the ocular responses can be tracked and measured by a variety of modalities. A Fourier transform can be used to compares the inertial head movement and eye movement response at various frequencies in a complex waveform and software can analyze the data. The stored data can be displayed remotely and abnormalities of the related ocular response to the head movement can then predict the performance of the user when performing an occupational activity.

In the prior art, clinicians have looked at the VOR response and made a binary judgment (e.g., the VOR was abnormal or normal). This normal/abnormal criterion would then be used to determine whether vestibular rehabilitation was needed. A better method for evaluating the VOR response would be to measure vestibulo-ocular performance on a continuous scale, just like we measure the speed of an athlete. By doing this, one can get a subject's human performance measurement. Specifically, there can be a VOR response score that more clearly establishes the vestibulo-ocular response measurement and expresses this response measurement in language that can more appropriately be applied to human performance measurement and improvement. Establishing such a scoring system will enable people to more accurately predict human performance with specific activities. It may also help in the development of activities that improve the human performance in fields where above average VOP is of benefit. The same use of scoring on a continuous scale and multi-frequency composite scoring can apply to DVA, DVS and RIS.

Areas of Application

Embodiments of the systems and methods described herein could be used in a variety of areas, including but not limited to the military, sports, medical, and commercial businesses. In the tests described herein, all oculomotor responses can be measured in a VR/AR/mixed (AR and VR)/holographic/synthetic 3D system. Eye, eyelid, and head movement can be tracked. Eye movement, eye position, visual acuity, pupil function, peripheral and central vision testing can all be easily performed with this technology in these platform systems. These eye activities can be correlated with movement of the extremities to assess hand eye coordination. Embodiments described herein can be used with a protective sport helmet including those designed for football, lacrosse, hockey, multi-sport, horse-back riding, cycling, motor-cross, whitewater, climbing, and baseball helmets. Various embodiments can also be used for safety helmets, such as construction or industrial helmets, and helmets used by security and/or military forces.

Sports.

Embodiments of the present invention, using ocular performance measurements, can be used in sports/athletic environments where ocular parameter measurement can help predict player performance, player fatigue and early detection of abnormalities such as concussions and traumatic brain injury. For example, if a player has an abnormal VOR/DVA in the horizontal plane, that person may not be able to catch a ball when competing in athletic activities that require the head to rotate in a horizontal plane. Similarly, if a player has a vertical VOR/DVA abnormality and is running downfield while looking upwards over the shoulder, the ball will not be in focus. Specifically, the retinal visual stability and accuracy would be diminished. In this instance, there would a higher likelihood of dropping the ball compared to another athlete who has normal VOR responses with normal DVA. If a VOR abnormality was determined to be present prior to play, which could result in difficulty with foveal fixation, and athlete could undergo VOR retraining to rectify the abnormality and therefore improve play performance. Alternatively, the coaching staff could select another athlete who did not have this abnormality. For example, on game day if a football player had an abnormal VOR, with resultant decline in the DVA, in the vertical plane (e.g., lack of visual fixation on an object of interest with upwards and downwards movement of the head), then it can be predicted that the athlete is predictable not likely to catch a ball while running downfield and looking upwards over the shoulder (e.g., you cannot catch, what you cannot accurately see). This would offer some value to the coaching staff in selecting plays for the player or players for the necessary play to be performed. Additionally, if an athlete had such an abnormality and could be given some rehabilitation methods prior to play, this could correct the abnormality and increase performance in that activity. Athletes who have had concussions or TBI can have a VOP abnormality, with resultant decrements in the VOR, DVA, or MS. Embodiments of the present invention can be an accurate method to determine when the athlete is ready to return to play activities, based on improvement of the VOR or DVA. It therefore can be utilized in TBI/concussion evaluation/assessment and management for return to play. It is also intended for athletes who wish to enhance their training and athletic/vocational performance. It can be used in fitness centers, sports training centers, athletic performance centers, and vocational performance centers.

Some ocular performance measurements, including VOR, can also be adversely affected by alcohol and drug use. Potential use of this testing can also provide a drug screen for those individuals suspected of having suboptimal performance. Playing at higher performance levels demands excellent eye fixation on the visual target of interest while they are in motion. If athletes wanted to perform at a higher level, it could change the culture of adverse behavior activities, knowing that these activities would have a negative effect on their performance by having poor visual fixation while doing the activity they enjoy.

Military personnel functioning in a high-level environment and requiring target fixation of their eyes, while performing other activities such as with head or body movement, require a normal VOR and normal DVA. If the VOR/DVA is abnormal, the individual will not demonstrate peak human performance. Embodiments of the present invention can be used by the military in places such as the pilot selection process or special operations community to aid in the selection of individuals without a VOR/DVA abnormality. VOP measurement could enable other individuals, who had normal foveal fixation ability to be chosen for a particular task that has better predictable performance for a particular duty of the day. Like that discussed above with athletes, ocular performance measurements, including visual pursuit tracking and VOR, can be adversely affected by alcohol and drug use. This testing can provide evidence of military personnel suspected of having potential of suboptimal performance before performing specific duties requiring high performance with eye fixation.

Medical.

Similarly, any person with a motion sensitivity disorder (such as motion sickness, vection induced motion sickness, or visually induced motion sickness) or a balance problem, either of a central or peripheral origin, will have a VOR/DVA abnormality. Individuals with such an abnormality will express symptoms of dizziness, disorientation, difficulty with focusing, nausea, fuzziness, and such other complaints as not being clear headed. Embodiments of the present invention can be useful to people who have experienced a vestibular insult, vestibular dysfunction or labyrinthine dysfunction such as those caused by infection, concussive injury, traumatic brain injury, vascular disease, ototoxic or vestibulotoxic medication use, surgical complications, Meniere's disease, people experiencing chronic imbalance, such as, but not limited to, stroke victims, people with systemic illnesses, the elderly and other people who have experienced head injuries, especially those who have experienced cerebral or labyrinthine (inner ear) concussions. It also can be utilized other centers which perform vestibular rehabilitation and athletic/vocational enhancement environments. This ocular performance measurement method using a faceguard, faceshield, visor, VR device or other attached display system discussed above, can be used as an objective tool for assisting in the diagnosis of traumatic brain injury (TBI), concussion and other degenerative cerebellar disorders that cause highly abnormal results.

Commercial.

Embodiments can also be used in other industries where individuals are expected to perform in high activity levels, or provocative environments.

Vestibular Rehabilitation.

VOR scoring can also be beneficial in determining who is likely to benefit with vestibular rehabilitation therapy. VOR scoring can also be used more objectively in determining the benefit or improvement with such therapy. The system can include improvement information that can be used by the user, a coach, a medical practitioner, or any other advisor to help interpret the scoring and provide advice and/or exercises to improve ocular reflex. Although vestibular rehabilitation therapy can improve the ocular responses, this scoring can accurately quantify the improvement and more ably predict who is able to return to their normal activity without loss of human performance. Having a VOP score can also provide feedback that helps to control abnormal VOR responses. When an ocular response is abnormal with head rotation (a VOR abnormality, for example), such a finding can also determine a need for improvement with rehabilitation. Repetitive head movement in the abnormal plane of rotation, while the eye remains fixed on a target of interest, can provide a means for improving or enhancing the VOR or other eye responses. Specifically, if a VOR abnormality is found to exist in the horizontal plane, VOR enhancement rehabilitation therapy is given in the same plane. In this instance, the user focuses on a target of interest and the user rotates the head horizontally, while continuing to look at the target. If a VOR abnormality is found to exist in the vertical plane, VOR enhancement rehabilitation therapy is also given in the similar plane of the abnormality. In this instance, the user focuses on a target of interest and the user rotates the head vertically, while continuing to look at the target. The head speed can be varied and the target, which the user is focused, can be changed. The process can be repeated as often as necessary until the VOR abnormality is corrected. This therapy can be performed in any plane where such an abnormality exists. The same use of scoring on a continuous scale and multi-frequency composite scoring can apply to DVA, DVS and RIS.

Embodiments of the inventions described herein can provide supernormal enhancement of these same systems where no balance disorder exists, as in the case for enhancement of athletic and vocational abilities. Embodiments can enable individuals to reach a higher level of performance in their occupation, enable them to have increased ocular performance functions when participating in their usual occupational or play activities as well as enabling cognitive training and rehabilitation. Such an enhancement methodology can be used in athletic/vocational enhancement or training and other training environments such as virtual reality training and the like.

Although the invention herein has been described with reference to particular embodiments, it is to be understood that these embodiments are merely illustrative of the principles and applications of the present invention. For example, the present invention may be used to protect workers in an industrial setting, at a construction site, etc. In order to accomplish this, the device of the present invention may, for example, be included in construction helmets. It is therefore to be understood that numerous modifications may be made to the illustrative embodiments and that other arrangements may be devised without departing from the spirit and scope of the present invention as defined by the appended claims.

A number of variations and modifications of the disclosed embodiments can also be used. The principles described here can also be used for applications other than sports. While the principles of the disclosure have been described above in connection with specific apparatuses and methods, it is to be clearly understood that this description is made only by way of example and not as limitation on the scope of the disclosure.

What is claimed is:

1. A human ocular performance measuring device wherein:
   the device is configured for measuring an ocular performance characteristic selected from the group of:
      vestibulo-ocular reflex;
      ocular saccades;
      pupillometry;
      pursuit tracking during visual pursuit;
      vergence;
      eye closure;
      focused position of the eyes;
      dynamic visual acuity;
      kinetic visual acuity;
      virtual retinal stability;
      retinal image stability;
      foveal fixation stability; and
      nystagmus; and
   the device comprises:
      an eye sensor wherein:
         the eye sensor comprises a video camera; and
         the eye sensor senses eye information selected from the group of:
            horizontal eye movement;
            vertical eye movement;
            pupil size; and
            eyelid movement;
      a head orientation sensor wherein:
         the head orientation sensor senses a head movement selected from the group of pitch and yaw of a person's head wherein pitch represents a rotation about a first axis representing up and down movement of the person's face when the rear of the person's head moves in the opposite direction and yaw represents horizontal movement of the face when looked at from the front about a second axis substantially aligned with the spine and perpendicular to the first axis; and
         the head orientation sensor senses the head movement in a range of frequencies between 0.01 Hertz and 15 Hertz;
         the head orientation sensor comprises a micro-electro-mechanical system integrated circuit comprising a module selected from the group consisting of an accelerometer, a magnetometer, and a gyroscope;
      an electronic circuit wherein:
         the electronic circuit comprises a central processing unit, and a memory unit;
         the electronic circuit is responsive to the eye movement information received from the eye sensor; and
         the electronic circuit is responsive to head movement information received from the head orientation sensor; and
   a helmet, comprising an inner frame having an interior surface and one or more shock absorption elements attached between the inner frame and a spherical shell, wherein:
      the one or more shock absorption elements couple the spherical shell to the inner frame;
      the spherical shell is external to the inner frame;
      the spherical shell has a circular geometry that when viewed horizontally at its horizontal midplane, includes a center point that is the rotational center of the spherical shell;
      the one or more shock absorption elements are sized to provide greater spacing between the inner frame and the spherical shell at the sides and the rear of the spherical shell than at the front of the spherical shell;
      the one or more shock absorption elements are sized to configure the alignment of the rotational center of the spherical shell with a proximate rotational center of a wearer's head; and
      the alignment between the rotational center of the spherical shell and the proximate rotational center of a wearer's head directly affects the effect of a tangential force caused by an impact on the spherical shell.

2. The device of claim 1 wherein:
the device measures vestibulo-ocular reflex.

3. The device of claim 1 wherein:
the device measures ocular saccades.

4. The device of claim 1 wherein:
the device measures pupillometry.

5. The device of claim 1 wherein:
the device measures pursuit tracking during visual pursuit.

6. The device of claim 1 wherein:
the device measures vergence.

7. The device of claim 1 wherein:
the device measures eye closure.

8. The device of claim 1 wherein:
the device measures focused position of the eyes.

9. The device of claim 1 wherein:
the device further measures an ocular performance characteristic selected from the group of dynamic visual acuity and kinetic visual acuity.

10. The device of claim 1 wherein:
the device further measures an ocular performance characteristic selected from the group of virtual retinal stability and retinal image stability.

11. The device of claim 1 wherein:
the device further measures an ocular performance characteristic selected from the group of foveal fixation stability and nystagmus.

12. The device of claim 1 wherein:
the device further comprises a display wherein the display is configured for presenting information selected from the group of:
   virtual reality information;
   augmented reality information; and
   synthetic computer-generated 3-dimensional information; and
the display is selected from the group of:
   a volumetric display;
   a hologram; and
   a lenticular display.

13. The device of claim 1 wherein:
the eye sensor senses eye movement information selected from the group of horizontal eye movement and vertical eye movement.

14. The device of claim 1 wherein:
the head orientation sensor senses pitch of the person's head and yaw of the person's head
the eye sensor senses eye horizontal eye movement and vertical eye movement;
the electronic circuit uses a Fourier transform to generate a vertical gain signal and a vertical phase signal in response to the vertical eye movement information and the pitch information; and
the electronic circuit uses a Fourier transform to generate a horizontal gain signal and a horizontal phase signal in response to the horizontal eye movement information and the yaw information.

15. The device of claim 1 wherein:
the eye sensor further senses the position of at least one eye;
the device further comprises a forward-facing camera; and
the forward-facing camera is responsive to the eye sensor.

16. A human ocular performance measuring system wherein:
the system is configured for measuring an ocular performance characteristic selected from the group of:
vestibulo-ocular reflex;
ocular saccades;
pupillometry;
pursuit tracking during visual pursuit;
vergence;
eye closure;
focused position of the eyes;
dynamic visual acuity;
kinetic visual acuity;
virtual retinal stability;
retinal image stability;
foveal fixation stability; and
nystagmus; and
the system comprises:
an eye sensor wherein:
the eye sensor comprises a video camera; and
the eye sensor senses eye movement information selected from the group of:
horizontal eye movement;
vertical eye movement;
pupillometry; and
eyelid movement;
a head orientation sensor wherein:
the head orientation sensor senses a head movement selected from the group of pitch and yaw of a person's head wherein pitch represents a rotation about a first axis representing up and down movement of the person's face when the rear of the person's head moves in the opposite direction and yaw represents horizontal movement of the face when looked at from the front about a second axis substantially aligned with the spine and perpendicular to the first axis; and
the head orientation sensor senses the head movement in a range of frequencies between 0.01 Hertz and 15 Hertz;
an electronic circuit wherein:
the electronic circuit comprises a central processing unit, and a memory unit;
the electronic circuit is responsive to the eye movement information received from the eye sensor; and
the electronic circuit is responsive to head movement information received from the head orientation sensor; and
a helmet, comprising an inner frame having an interior surface and one or more shock absorption elements attached between the inner frame and a spherical shell, wherein:
the one or more shock absorption elements couple the spherical shell to the inner frame;
the spherical shell is external to the inner frame;
the spherical shell has a circular geometry that when viewed horizontally at its horizontal midplane, includes a center point that is the rotational center of the spherical shell;
the one or more shock absorption elements are sized to provide greater spacing between the inner frame and the spherical shell at the sides and the rear of the spherical shell than at the front of the spherical shell;
the one or more shock absorption elements are sized to configure the alignment of the rotational center of the spherical shell with a proximate rotational center of a wearer's head; and
the alignment between the rotational center of the spherical shell and the proximate rotational center of a wearer's head directly affects the effect of a tangential force caused by an impact on the spherical shell.

17. The system of claim 16 wherein:
the head orientation sensor comprises a head-worn micro-electro-mechanical system integrated circuit comprising a module selected from the group consisting of an accelerometer, a magnetometer, and a gyroscope.

18. The system of claim 16 wherein:
the head orientation sensor comprises a video camera; and
the system further comprises a display wherein the display is configured for presenting information selected from the group of:
virtual reality information;
augmented reality information; and
synthetic computer-generated 3-dimensional information; and
the display is selected from the group of:
a volumetric display;
a hologram; and
a lenticular display.

19. The system of claim 16 wherein:
the head orientation sensor comprises the same video camera as the eye sensor.

20. A method for measuring human ocular performance comprising the steps of:
establishing a device that comprises:
an eye sensor comprising a video camera configured for sensing
eye movement information selected from the group of:
horizontal eye movement;
vertical eye movement;
pupillometry; and
eyelid movement;
a head orientation sensor configured for sensing a head movement selected from the group of pitch and yaw of a person's head wherein pitch represents a rotation about a first axis representing up and down movement of the person's face when the rear of the person's head moves in the opposite direction and yaw represents horizontal movement of the face when looked at from the front about a second axis substantially aligned with the spine and perpendicular to the first axis;

an electronic circuit; and a helmet, comprising an inner frame having an interior surface and one or more shock absorption elements attached between the inner frame and a spherical shell, wherein:

the one or more shock absorption elements couple the spherical shell to the inner frame;

the spherical shell is external to the inner frame;

the spherical shell has a circular geometry that when viewed horizontally at its horizontal midplane, includes a center point that is the rotational center of the spherical shell;

the one or more shock absorption elements are sized to provide greater spacing between the inner frame and the spherical shell at the sides and the rear of the spherical shell than at the front of the spherical shell;

the one or more shock absorption elements are sized to configure the alignment of the rotational center of the spherical shell with a proximate rotational center of a wearer's head; and the alignment between the rotational center of the spherical shell and the proximate rotational center of a wearer's head directly affects the effect of a tangential force caused by an impact on the spherical shell; and using the electronic circuit to:

receive eye movement information from the eye sensor;

receive head movement information from the head orientation sensor; and generate a gain signal and a phase signal using the eye movement information, and the head movement information; and measure an ocular performance characteristic selected from the group of:

vestibulo-ocular reflex;
ocular saccades;
pupillometry;
pursuit tracking during visual pursuit;
vergence;
eye closure;
focused position of the eyes;
dynamic visual acuity;
kinetic visual acuity;
virtual retinal stability;
retinal image stability;
foveal fixation stability; and
nystagmus.

\* \* \* \* \*